US007190832B2

(12) United States Patent
Frost et al.

(10) Patent No.: US 7,190,832 B2
(45) Date of Patent: Mar. 13, 2007

(54) COMPUTATIONAL METHODS FOR THE SEGMENTATION OF IMAGES OF OBJECTS FROM BACKGROUND IN A FLOW IMAGING INSTRUMENT

(75) Inventors: Keith L. Frost, Seattle, WA (US); James K. Riley, Redmond, WA (US)

(73) Assignee: Amnis Corporation, Seattle, WA (US)

( * ) Notice: Subject to any disclaimer, the term of this patent is extended or adjusted under 35 U.S.C. 154(b) by 725 days.

(21) Appl. No.: 10/200,018

(22) Filed: Jul. 17, 2002

(65) Prior Publication Data

US 2003/0086608 A1  May 8, 2003

Related U.S. Application Data

(63) Continuation-in-part of application No. 09/939,292, filed on Aug. 24, 2001, now Pat. No. 6,532,061, and a continuation-in-part of application No. 09/939,049, filed on Aug. 24, 2001, now Pat. No. 6,507,391, and a continuation-in-part of application No. 10/132,059, filed on Apr. 24, 2002, now Pat. No. 6,763,149.

(60) Provisional application No. 60/306,126, filed on Jul. 17, 2001.

(51) Int. Cl.
*G06K 9/34* (2006.01)
*G06K 9/00* (2006.01)

(52) U.S. Cl. ...................... 382/173; 382/103
(58) Field of Classification Search ................ 382/103, 382/173, 164, 291
See application file for complete search history.

(56) References Cited

U.S. PATENT DOCUMENTS

| 3,922,069 A | 11/1975 | Kishikawa et al. ......... 359/633 |
| 4,635,293 A | 1/1987 | Watanabe .................... 382/130 |
| 4,677,680 A | 6/1987 | Harima et al. .............. 382/112 |

(Continued)

FOREIGN PATENT DOCUMENTS

WO   WO 00/42412   7/2000

OTHER PUBLICATIONS

Kubota, Fumio et al. 1995. "Flow Cytometer and Imaging Device Used in Combination." *Cytometry*: 21:129-132.

(Continued)

*Primary Examiner*—Vikkram Bali
*Assistant Examiner*—Colin LaRose
(74) *Attorney, Agent, or Firm*—Ronald M. Anderson

(57) ABSTRACT

In automated computation-based interpretation of images, the accuracy and reliability of the detection and delineation of objects, known as "object segmentation," is implemented so as to provide efficient performance. In a multi-step process, objects are first detected and captured into regions of interest (ROIs). Sets of pixels belonging to respective objects are then identified. Preferably object detection is achieved using both a two-dimensional (2D) low pass filter and a 2D edge enhancement filter. Two different gradient based edge enhancement filters are disclosed. One embodiment of the invention defines a (ROI) by first determining the center of objects by executing a plurality of decimations on the filtered image data, and then establishing object boundaries. In a second embodiment the ROI is defined by generating an amplitude histogram of the filtered image data, and for histograms exceeding a threshold determining by pixel which rows are to be included in the ROI.

49 Claims, 36 Drawing Sheets

U.S. PATENT DOCUMENTS

| | | | | |
|---|---|---|---|---|
| 4,770,992 | A | | 9/1988 | Van den Engh et al. ......... 435/6 |
| 4,786,165 | A | | 11/1988 | Yamamoto et al. ........... 356/23 |
| 4,905,296 | A | * | 2/1990 | Nishihara ................... 382/203 |
| 5,096,807 | A | | 3/1992 | Leaback ....................... 435/6 |
| 5,119,444 | A | * | 6/1992 | Nishihara ................... 382/263 |
| 5,141,609 | A | | 8/1992 | Sweedler et al. ........... 356/344 |
| 5,142,592 | A | * | 8/1992 | Moler ....................... 382/200 |
| 5,153,916 | A | | 10/1992 | Inagaki et al. .............. 382/151 |
| 5,159,397 | A | | 10/1992 | Kosaka et al. ................ 356/73 |
| 5,159,398 | A | | 10/1992 | Maekawa et al. ............. 356/73 |
| 5,159,642 | A | | 10/1992 | Kosaka ........................... 382/6 |
| 5,247,339 | A | | 9/1993 | Ogino .......................... 356/73 |
| 5,272,354 | A | | 12/1993 | Kosaka ....................... 250/574 |
| 5,351,311 | A | | 9/1994 | Rogers ......................... 382/156 |
| 5,422,712 | A | | 6/1995 | Ogino .......................... 356/73 |
| 5,444,527 | A | | 8/1995 | Kosaka ........................ 356/73 |
| 5,471,294 | A | | 11/1995 | Ogino .......................... 356/73 |
| 5,548,395 | A | | 8/1996 | Kosaka ........................ 356/73 |
| 5,596,401 | A | | 1/1997 | Kusuzawa ................... 356/23 |
| 5,633,503 | A | | 5/1997 | Kosaka ..................... 250/458.1 |
| 5,644,388 | A | | 7/1997 | Maekawa et al. ............. 356/73 |
| 5,674,743 | A | | 10/1997 | Ulmer ..................... 435/287.2 |
| 5,695,934 | A | | 12/1997 | Brenner ......................... 435/6 |
| 5,754,291 | A | | 5/1998 | Kain .......................... 356/344 |
| 5,760,899 | A | | 6/1998 | Eismann ..................... 356/326 |
| RE35,868 | E | | 8/1998 | Kosaka ....................... 250/574 |
| 5,825,910 | A | * | 10/1998 | Vafai .......................... 382/132 |
| 5,831,723 | A | | 11/1998 | Kubota et al. ................. 356/73 |
| 5,848,123 | A | | 12/1998 | Strommer ................. 378/98.8 |
| 5,855,753 | A | | 1/1999 | Trau et al. .................. 204/484 |
| 5,929,986 | A | | 7/1999 | Slater et al. ................ 356/326 |
| 5,959,953 | A | | 9/1999 | Alon ........................ 369/44.41 |
| 5,982,915 | A | | 11/1999 | Doi et al. ................... 382/130 |
| 5,988,862 | A | | 11/1999 | Kacyra et al. .............. 364/578 |
| 6,007,994 | A | | 12/1999 | Ward et al. ..................... 435/6 |
| 6,014,468 | A | | 1/2000 | McCarthy et al. .......... 382/254 |
| 6,066,459 | A | | 5/2000 | Garini et al. ................... 435/6 |
| 6,116,739 | A | | 9/2000 | Ishihara et al. ............... 353/31 |
| 6,156,465 | A | | 12/2000 | Cao et al. ..................... 430/30 |
| 6,167,146 | A | * | 12/2000 | Rogers et al. .............. 382/132 |
| 6,210,973 | B1 | | 4/2001 | Pettit .......................... 436/172 |
| 6,211,955 | B1 | | 4/2001 | Basiji et al. ................. 356/326 |
| 6,249,341 | B1 | | 6/2001 | Basiji et al. .................. 356/73 |
| 6,256,096 | B1 | | 7/2001 | Johnson ...................... 356/335 |
| 6,330,081 | B1 | | 12/2001 | Scholten ..................... 358/463 |
| 6,330,361 | B1 | | 12/2001 | Mitchell et al. ............ 382/211 |
| 6,363,163 | B1 | | 3/2002 | Xu et al. ..................... 382/130 |
| 6,381,363 | B1 | | 4/2002 | Murching et al. .......... 382/164 |
| 6,522,781 | B1 | | 2/2003 | Norikane et al. ........... 382/203 |
| 6,535,632 | B1 | * | 3/2003 | Park et al. ................... 382/164 |
| 6,549,664 | B1 | | 4/2003 | Daiber et al. ............... 382/232 |
| 6,707,940 | B1 | * | 3/2004 | Qian .......................... 382/173 |
| 6,763,149 | B2 | | 7/2004 | Riley et al. ................. 382/294 |
| 6,766,064 | B1 | * | 7/2004 | Langan et al. .............. 382/274 |
| 7,006,710 | B2 | | 2/2006 | Riley et al. ................. 382/294 |
| 2001/0006416 | A1 | | 7/2001 | Johnson ....................... 356/73 |
| 2002/0126275 | A1 | | 9/2002 | Johnson ..................... 356/317 |

OTHER PUBLICATIONS

Kubota, F. 2003. "Analysis of red cell and platelet morphology using an imaging-combined flow cytometer." *Clin. Lab. Haem.*: 25:71-76.

Ong, S.H. and P.M. Nickolls. 1991. "Optical Design in a Flow System For Imagina Cells." *Sciences in Medicine*:14:2:74-80.

Ong, S.H. and P.M. Nickolls. 1994. "Analysis of MTF Degradation in the Imaging of Cells in a Flow System." *International Journal of Imaging Systems & Technology*: 5:243-250.

Satoh, Kaneo et al. 2002. "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry*: 48:194-201.

Wang, Fu-sheng and Fumio Kubota. 2002. "A Novel Apoptosis Research Method With Imaging-Combined Flow Cytometer and HITC OR IR-125 Staining." *Cytometry*: 50:267-274.

Wietzorrek, Joachim et al. 1999. "A New Multiparameter Flow Cytometer: Optical and Electrical Cell Analysis in Combination With Video Microscopy in Flow." *Cytometry*: 35:291-301.

Ong, S.-H.; Horne, D.; Yeung, C.-K.; Nickolls, P.; Cole, T. "Development of an Image Flow Cytometer." Analytical and Quantitative Cytology and Histology. XIVth International Conference on Medical and Biological Engineering and the VIIth International Conference on Medical Physics, Espoo, Finland. Aug. 11-15, 1985. pp. 375-382.

Ong, Sim Heng. "Development of a System for Imaging and Classifying Biological Cells in a Flow Cytometer." Doctor of Philosophy Thesis. University of Sydney, School of Electrical Engineering. Aug. 1985.

* cited by examiner

FIG. 7

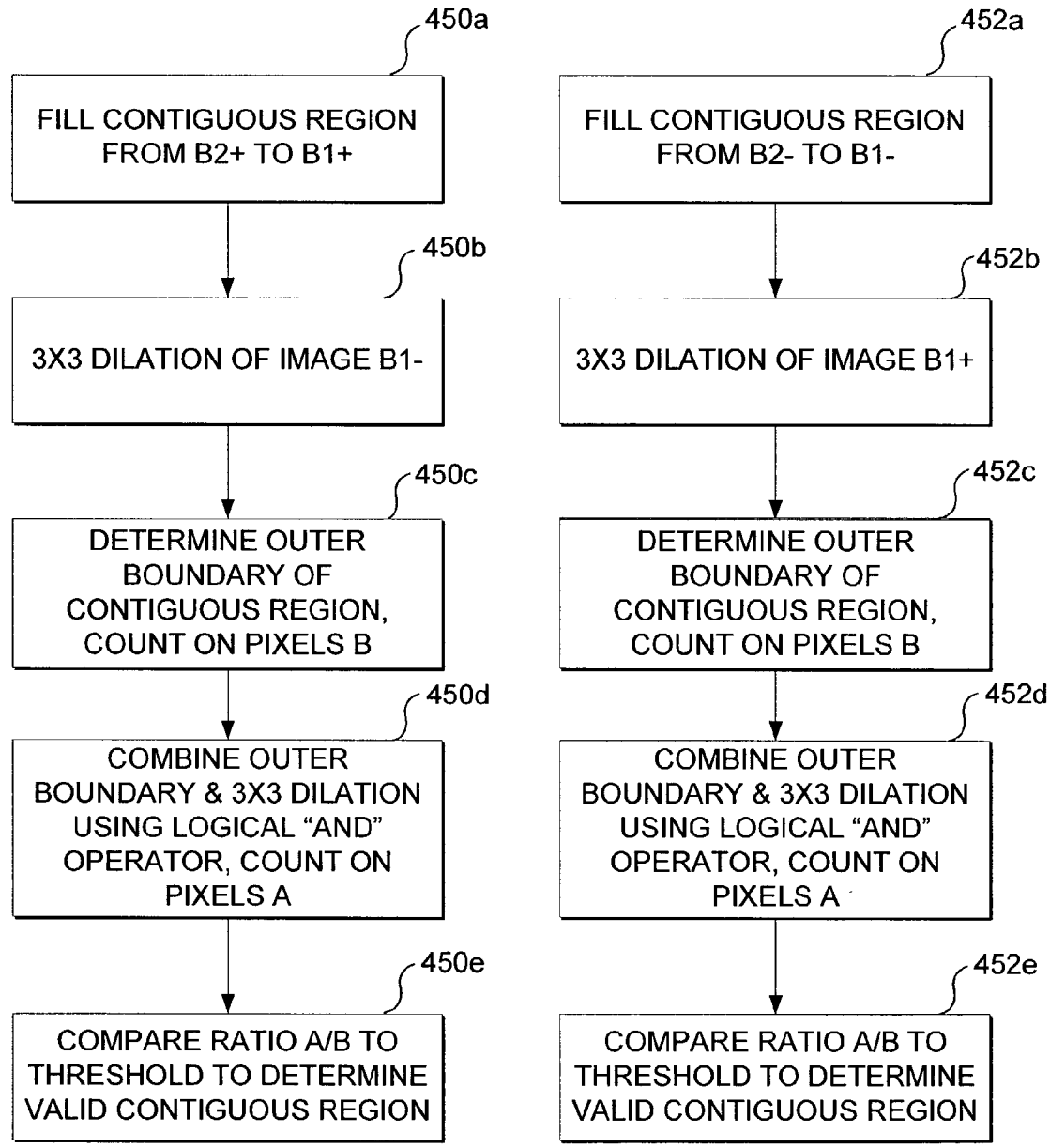
*FIG. 29B*     *FIG. 29C*

COMPUTATIONAL METHODS FOR THE SEGMENTATION OF IMAGES OF OBJECTS FROM BACKGROUND IN A FLOW IMAGING INSTRUMENT

RELATED APPLICATIONS

This application is based on prior copending provisional application Ser. No. 60/306,126, filed Jul. 17, 2001, the benefits of the filing date of which is hereby claimed under 35 U.S.C. § 119(e) and is a continuation-in-part application of prior copending patent applications, Ser. No. 10/132,059, which was filed on Apr. 24, 2002 now U.S. Pat. No. 6,763,149, Ser. No. 09/939,049, which was filed on Aug. 24, 2001 now U.S. Pat. No. 6,507,391, and Ser. No. 09/939,292, which was filed on Aug. 24, 2001 now U.S. Pat. No. 6,532,061, the benefits of the filing dates of which are hereby claimed under 35 U.S.C. § 120.

FIELD OF THE INVENTION

The present invention generally relates to processing image data, and more specifically to processing images data in a flow imaging instrument so as to segment pixels corresponding to an object of interest in a flow from pixels corresponding to a background.

BACKGROUND OF THE INVENTION

The electronic capture and storage of digitized images has enabled the application of machine vision algorithms to the automation of image analysis operations to improve productivity and accuracy beyond levels that can reasonably be achieved by human observers. For example, robotic machine vision systems now perform routine inspections of mechanical components in applications too tedious or demanding to be carried out manually. Similarly, in diagnostic medicine and life science research, computer analysis is beneficially applied to images captured by robotic microscopes to expand the extent, thoroughness, and accuracy of searches for indications of pathology or for the quantification of the signals from probes for identifying important molecular components of cells.

SUMMARY OF THE INVENTION

The present invention is a method for processing a signal generated by an imaging system, where such a signal corresponds to image data. The signal processing of the present invention segments the image data into a region of interest (ROI) that includes an object of interest, and background portion. Image data corresponding to the background portion of the image can be discarded, while image data corresponding to the ROI is further processed to define the boundaries of the object of interest, generating processed image data. The processed image data is made available for analysis. It is anticipated that one such analysis will be determining one or more characteristics of the object of interest.

The image data can be obtained by many different types of imaging systems. A preferred imaging system is a multichannel imaging system including a dispersing element that separates light from an object into a plurality of different light beams. An image is produced from each such light beam, and directed to a pixelated detector, which in turn produces a multichannel signal, in which each channel corresponds to image data from a different image. Preferably a TDI detector is employed.

An object in the image data is detected by filtering the image data. If no object is detected, that image data can be discarded. Once image data containing an object is identified (i.e. an object is detected via the filtering operations), a ROI is defined that encompasses the object found, and preferably is smaller in size than the original image data. Once the ROI is identified, a binary mask is generated to define the boundaries of the object of interest identified in the ROI. Preferably the binary mask is generated by executing binomial blurring operations on the filtered image data in the ROI to generate an approximation of a Laplacian of Gaussian (LOG) image. A plurality of binary images are produced based on using predetermined threshold values selected to ensure that the LOG image lies within the range of the predetermined threshold values. A series of morphological operations are executed on the binary images, to generate the binary mask used to define the boundaries of the object of interest identified in the ROI.

The LOG image is preferably generated by performing a small binomial blur operation on the filtered image data in the ROI, producing an approximation of Gaussian blurred image data. Then shifted image data is generated by shifting the filtered image data in bitwise fashion. The shifted image data is subtracted from the Gaussian blurred image data to generate difference image data. Another binomial blur operation is performed on the difference image data to generate data that approximates a LOG image.

Preferably the filtering operations employed for object detection include a low pass filtering operation. A boxcar filter, particularly a 3×3 boxcar filter, can be beneficially employed for this purpose. A preferred object detector combines such a low pass filter with a high pass or edge enhancement filter. Gradient operators are preferably employed in such high pass or edge enhancement filters. Such filters increase the amplitude magnitude of a specific pixel based on amplitude characteristics of adjacent pixels. In one embodiment, a plurality of axes defined by adjacent pixels are manipulated to determine an axis of least inclination. The axis of least inclination can then be further manipulated to define the magnitude by which the amplitude of specific pixel should be increased. In another embodiment, an equation is defined in terms of the specific pixel and four adjacent pixels, and the magnitude by which the amplitude of specific pixel should be increased is obtained by solving the equation.

Once an object has been detected, a ROI is defined for that object. In one embodiment a series of decimations are performed on the filtered image data, and a peak is located for the most heavily decimated filtered image data. Preferably, the filtered image data is decimated until all of the filtered image data is reduced to a single pixel value. A peak of that single pixel value is obtained. That peak is utilized to extrapolate peak locations for each other decimation, as well as the filtered image data, enabling the largest peak of the undecimated filtered image data to be determined. The largest peak in the undecimated filtered image data corresponds to the center of the object. Once the center of the object is determined, pattern analysis techniques can be employed to determine the boundaries of a ROI that encompasses the object.

In another embodiment, filtered image data is used to generate an amplitude histogram. The mean of the amplitude histogram is compared to a threshold. If the mean is greater than the threshold, each pixel represented in the filtered image data is compared to the threshold, and each pixel having an amplitude magnitude greater than the threshold is included in the ROI. Preferably, any time one pixel in a row is included in the ROI, all other pixels in that row are also included in the ROI, and no other pixels in that row need to be compared to the threshold. This results in a ROI that includes the same number of columns as the image, but fewer rows. The process can be repeated on the ROI to eliminate columns that do not contain a pixel having an amplitude magnitude greater than the threshold. Preferably, a few additional rows and columns are included in the ROI, even if no pixels in such rows or columns are greater in magnitude than the threshold, to ensure the object is fully encompassed by the ROI.

In addition to the aforementioned embodiments relating to the method, the present invention is also directed to a system having elements that carry out functions generally consistent with the steps of the method described above. One system embodiment includes a memory in which a plurality of machine instructions defining a signal conditioning software program are stored, and a processor that is coupled to the memory to access the machine instructions. Execution of the machine instructions by the processor causes it to detect objects by filtering image data, to define a ROI encompassing the detected object, and to determine boundaries of the detected object. It is contemplated that the memory, the machine instructions, and the processor might comprise either a programmed computer, an application specific integrated circuit (ASIC), or an oscilloscope.

While the signal processing techniques of the present invention can be applied to image data collected from many different types of imaging systems, it should be understood that the present invention is particularly well suited to process image signal data in real time. The processing steps have been selected and devised with the goal of achieving a computationally efficient signal processing algorithm. It is anticipated that the signal processing techniques of the present invention will be beneficially employed for real time processing of image signal data obtained in conjunction with an imaging system that collects image data in flow. Such an application requires that the signal processing applied to a first image be completed in real time, i.e. rapidly enough that processing capacity is available to be utilized to apply the same signal processing to the next image.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 7:
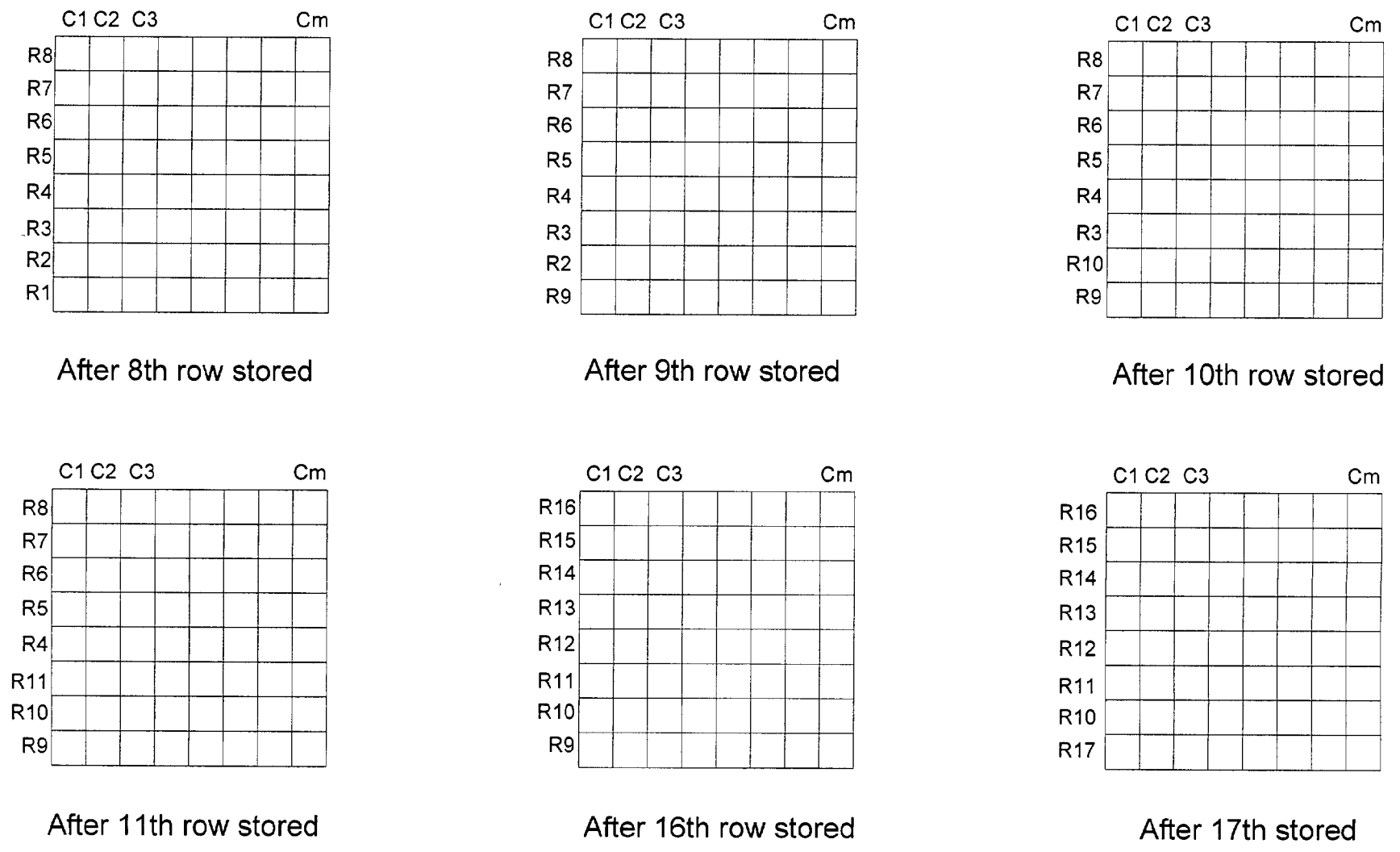
Figure 8:
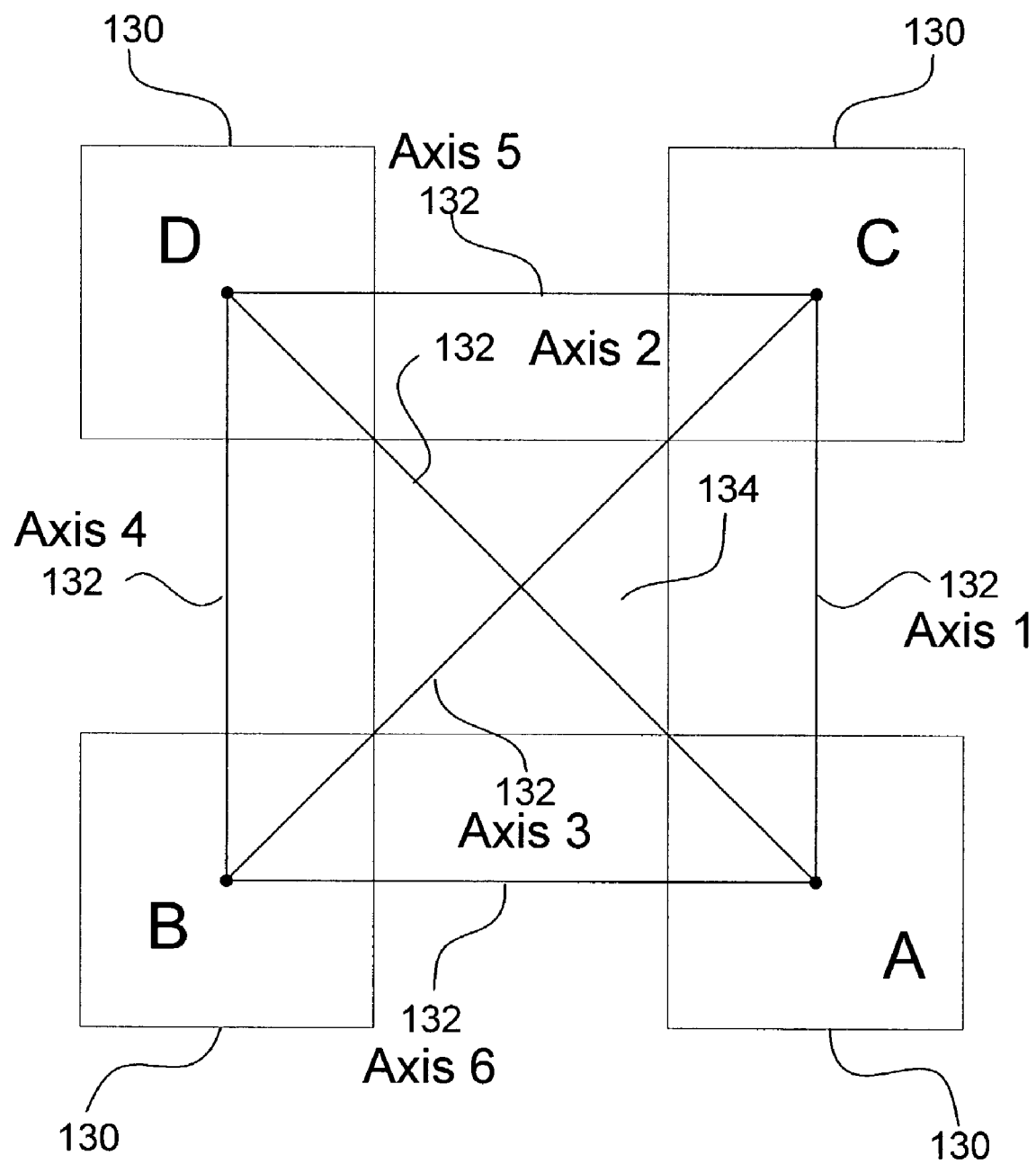
Figure 9:
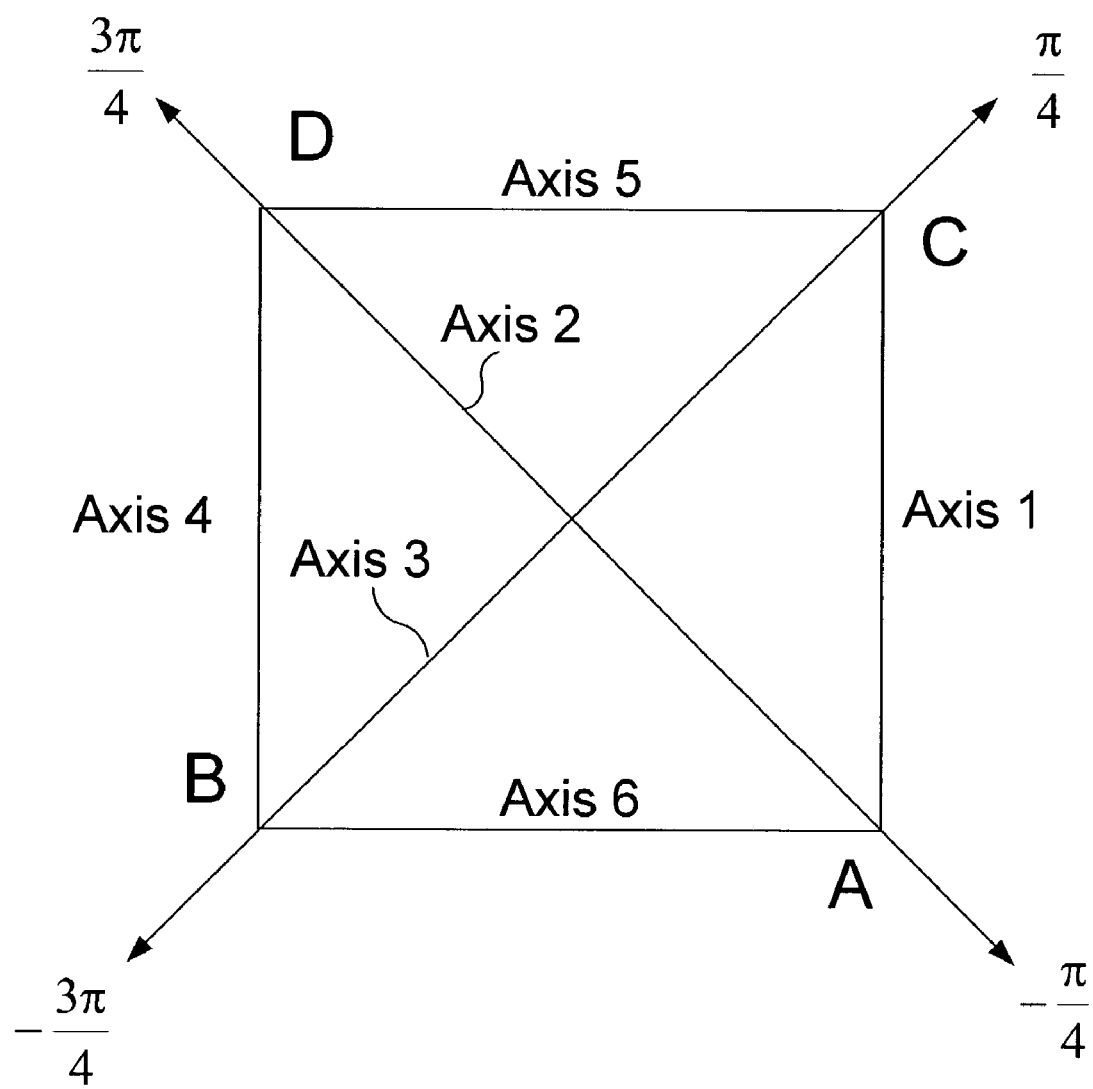
Figure 10:
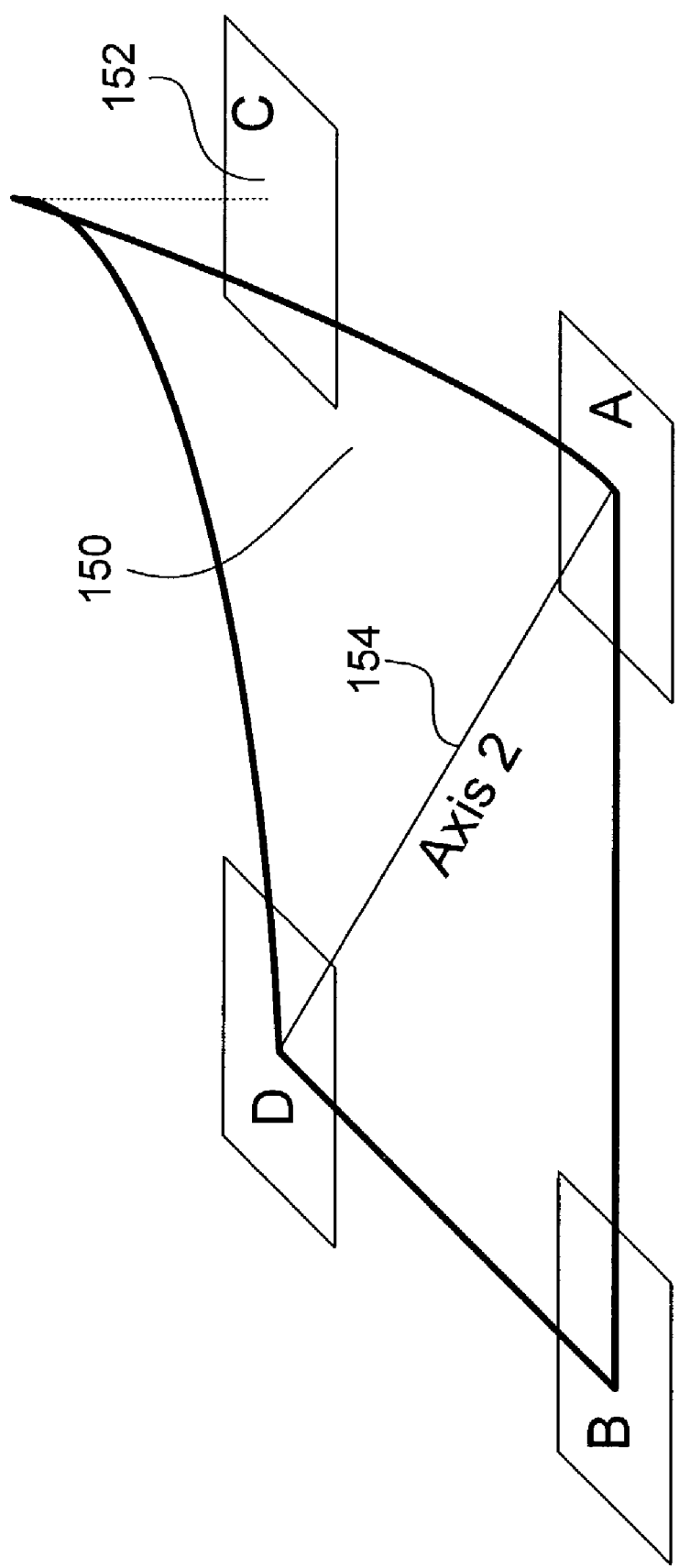
Figure 11:
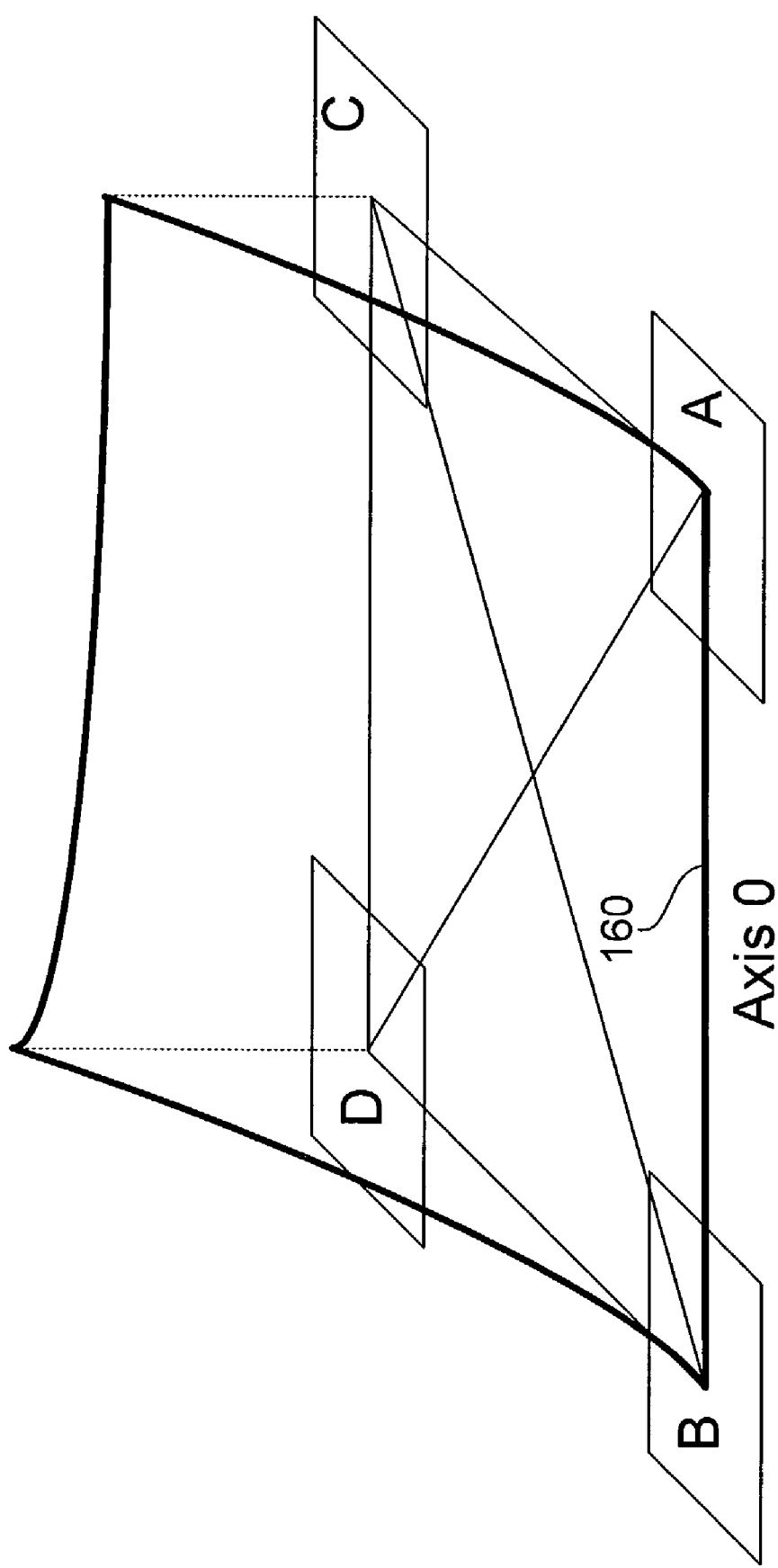
Figure 12:
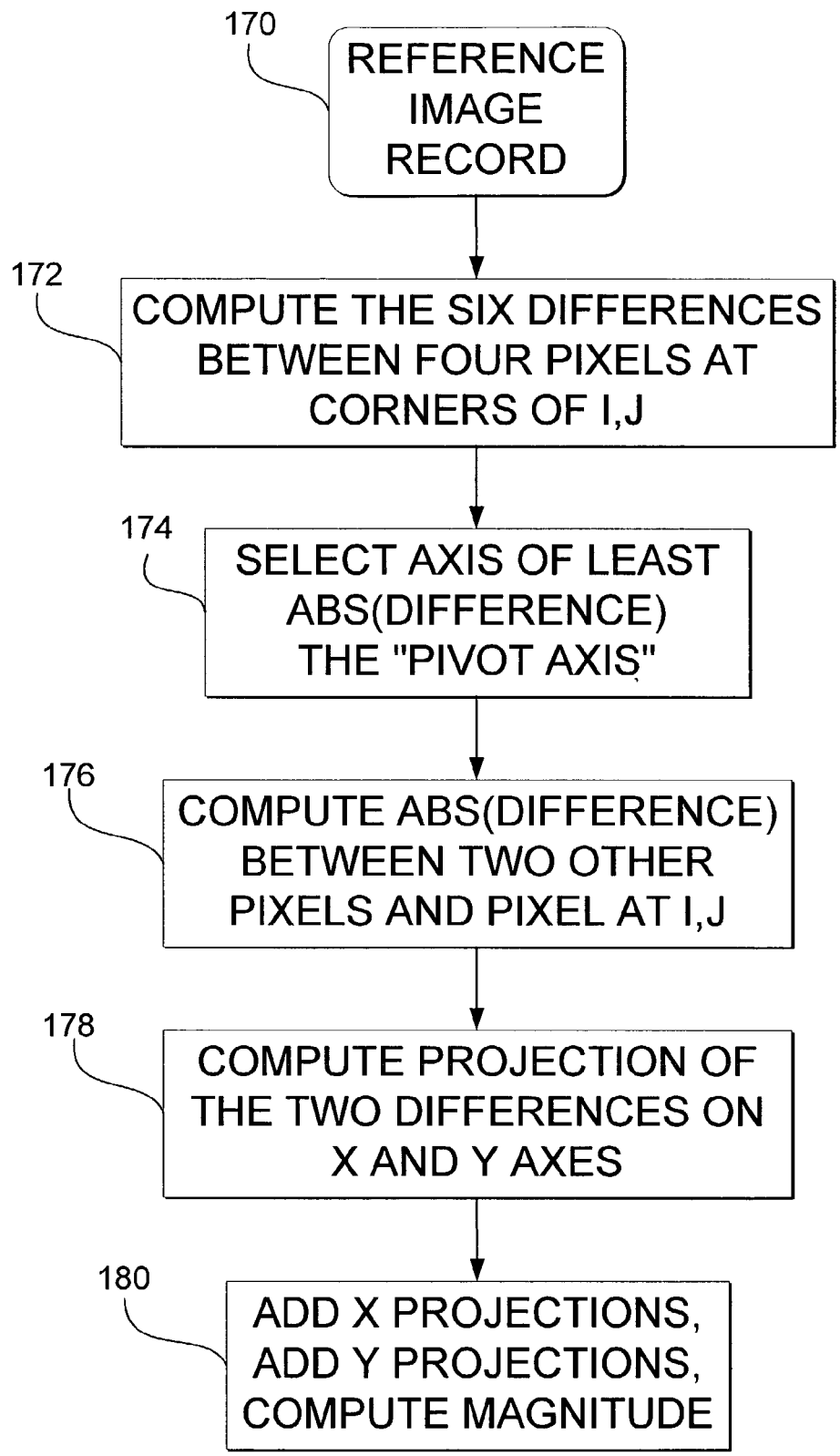
Figure 13:
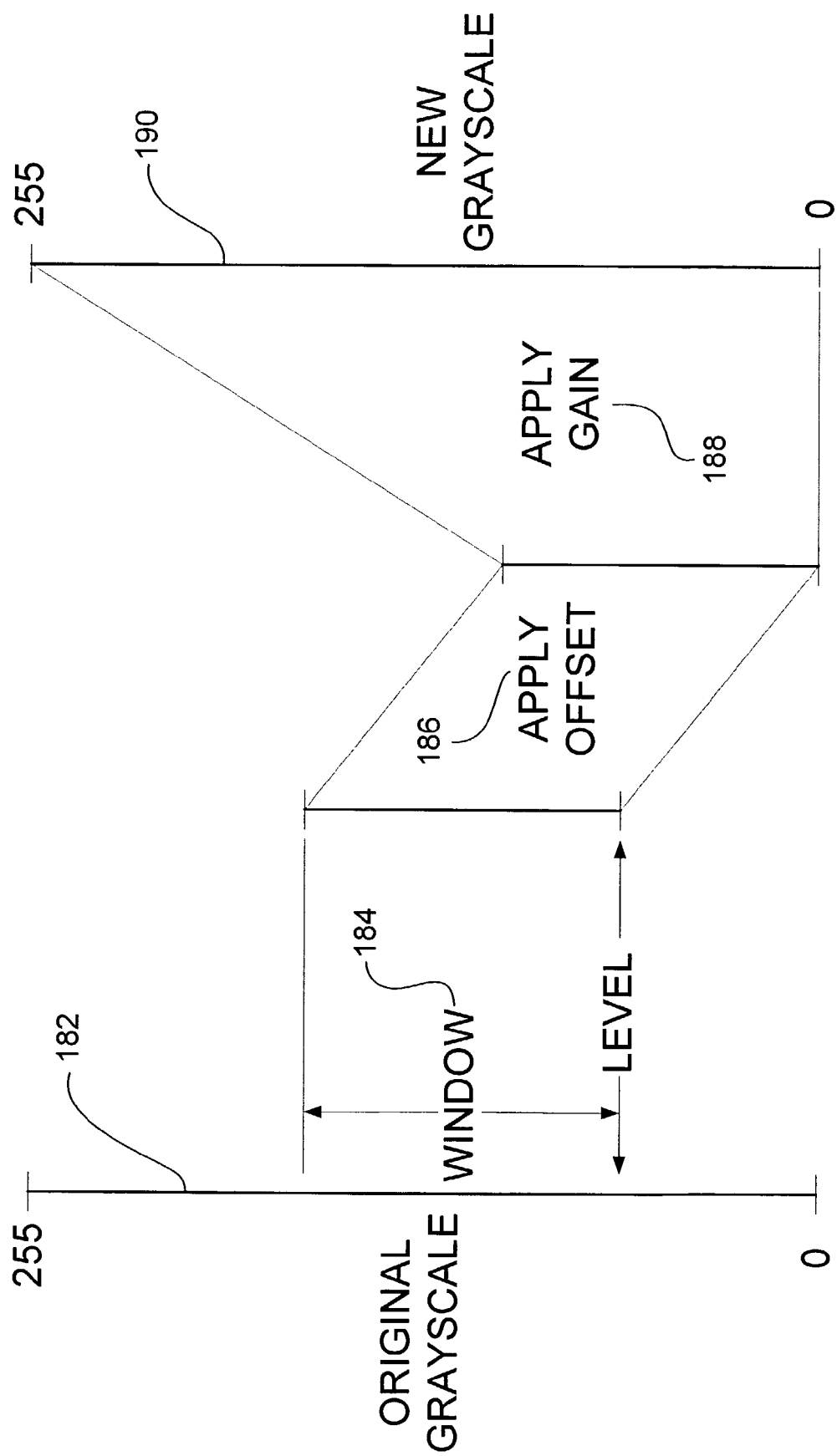
Figure 14:
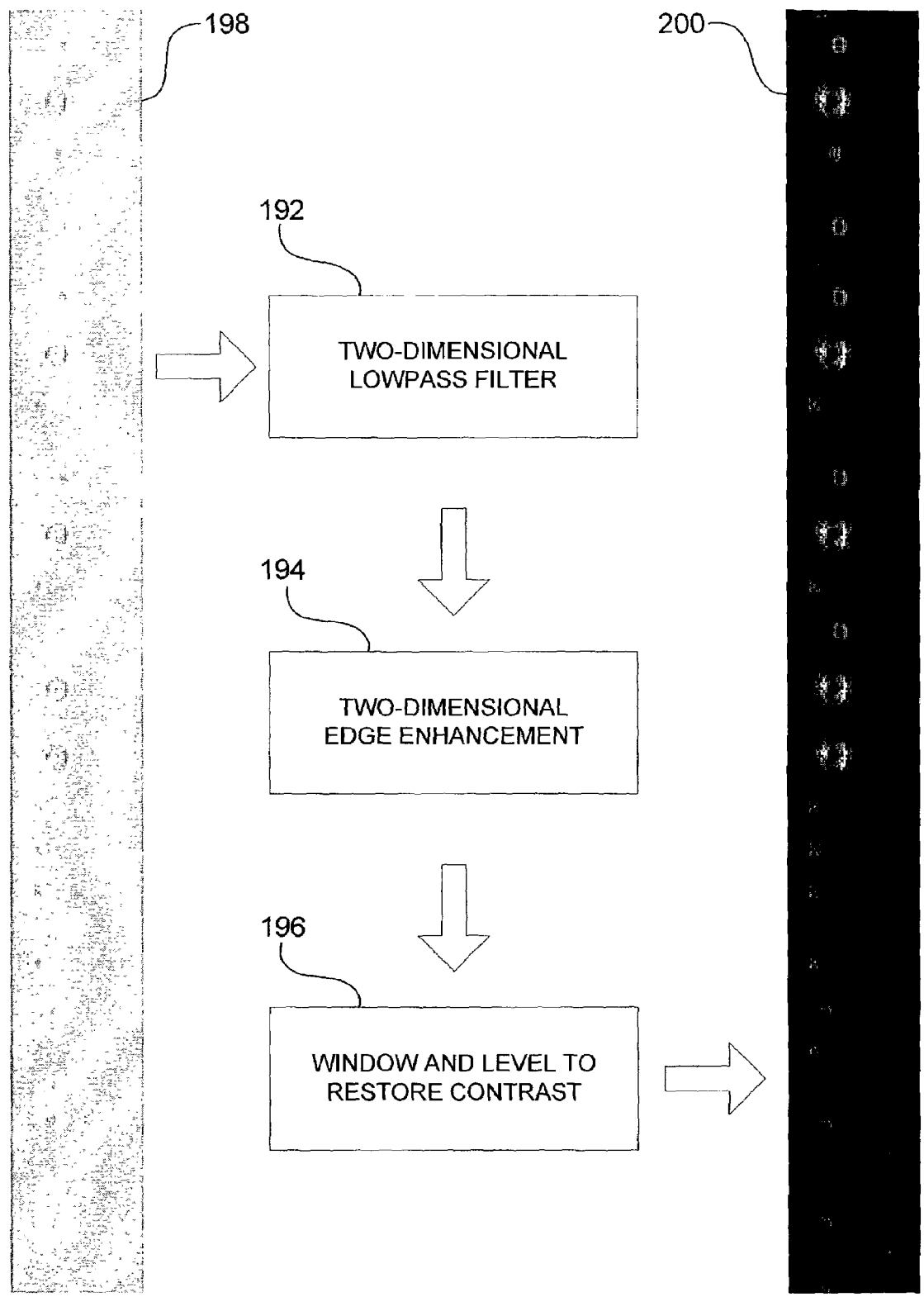
Figure 15:
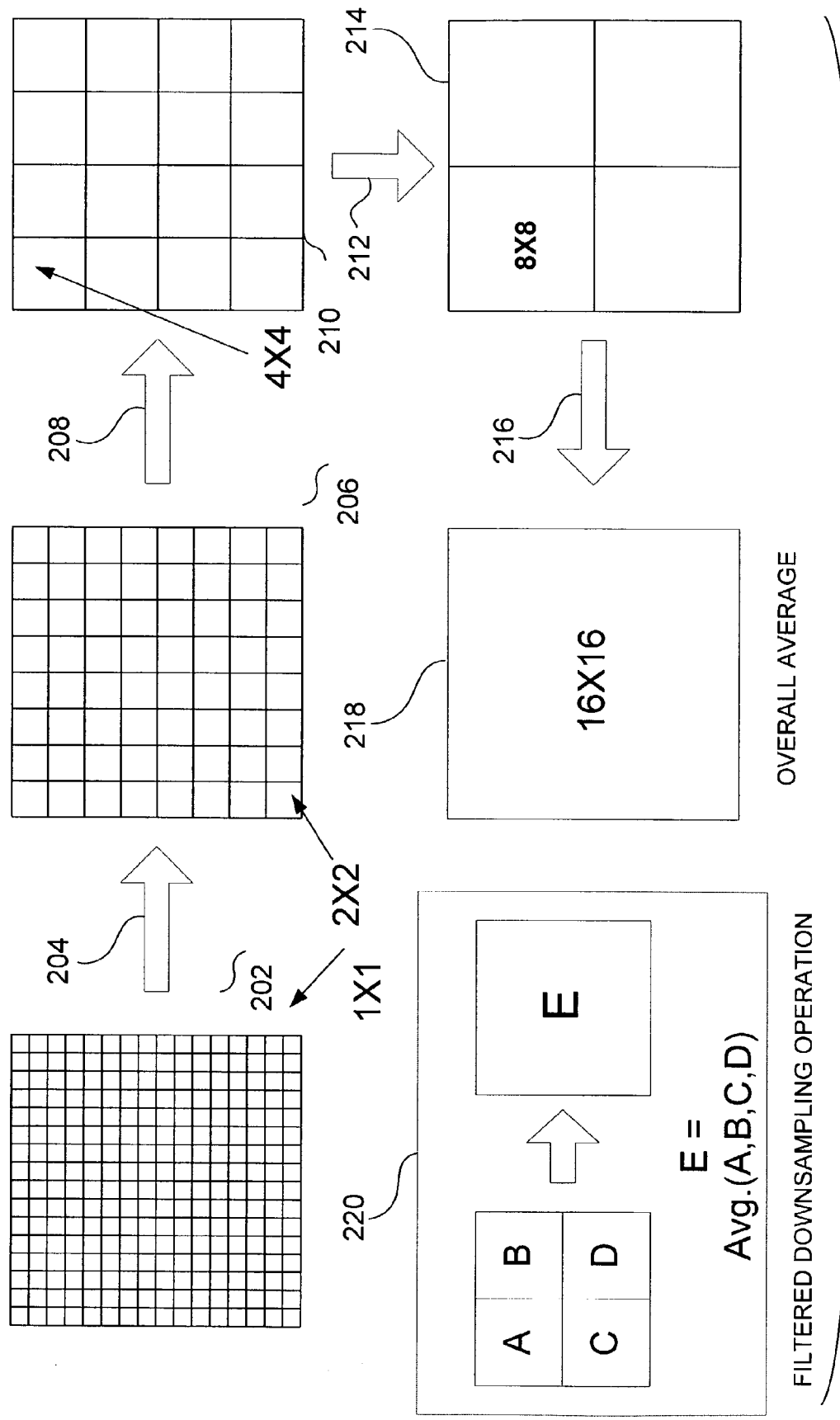
Figure 16:
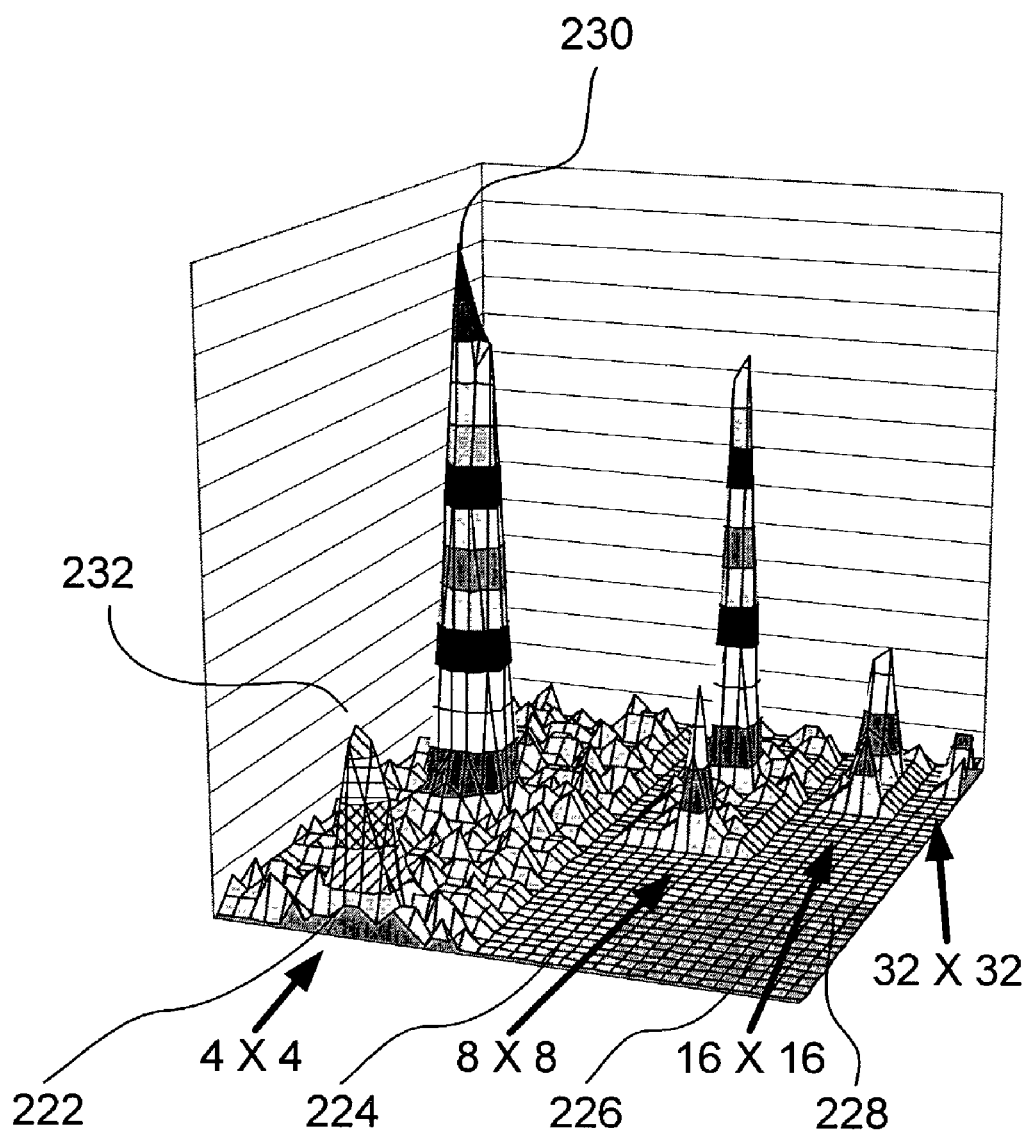
Figure 17:
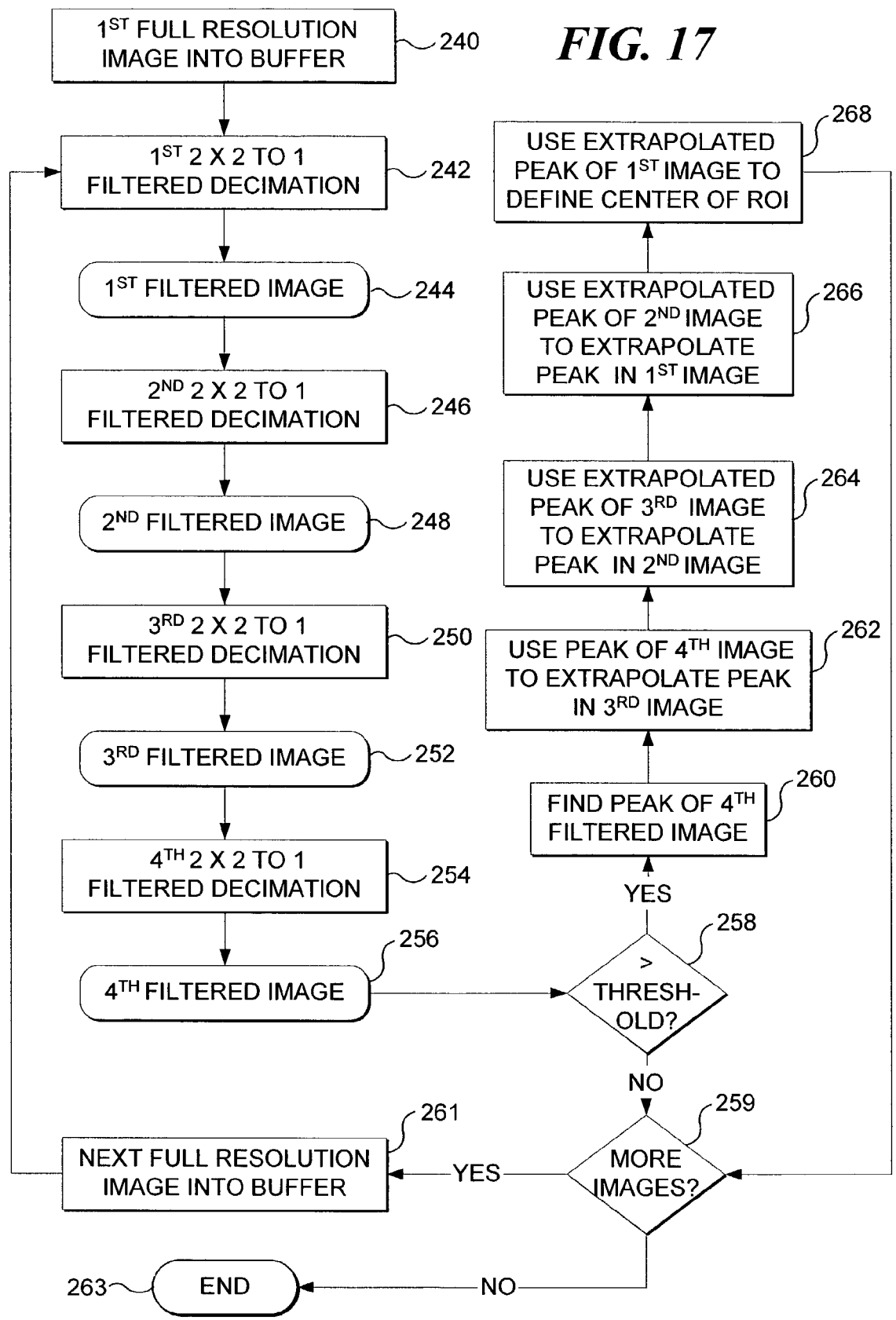
Figure 18:
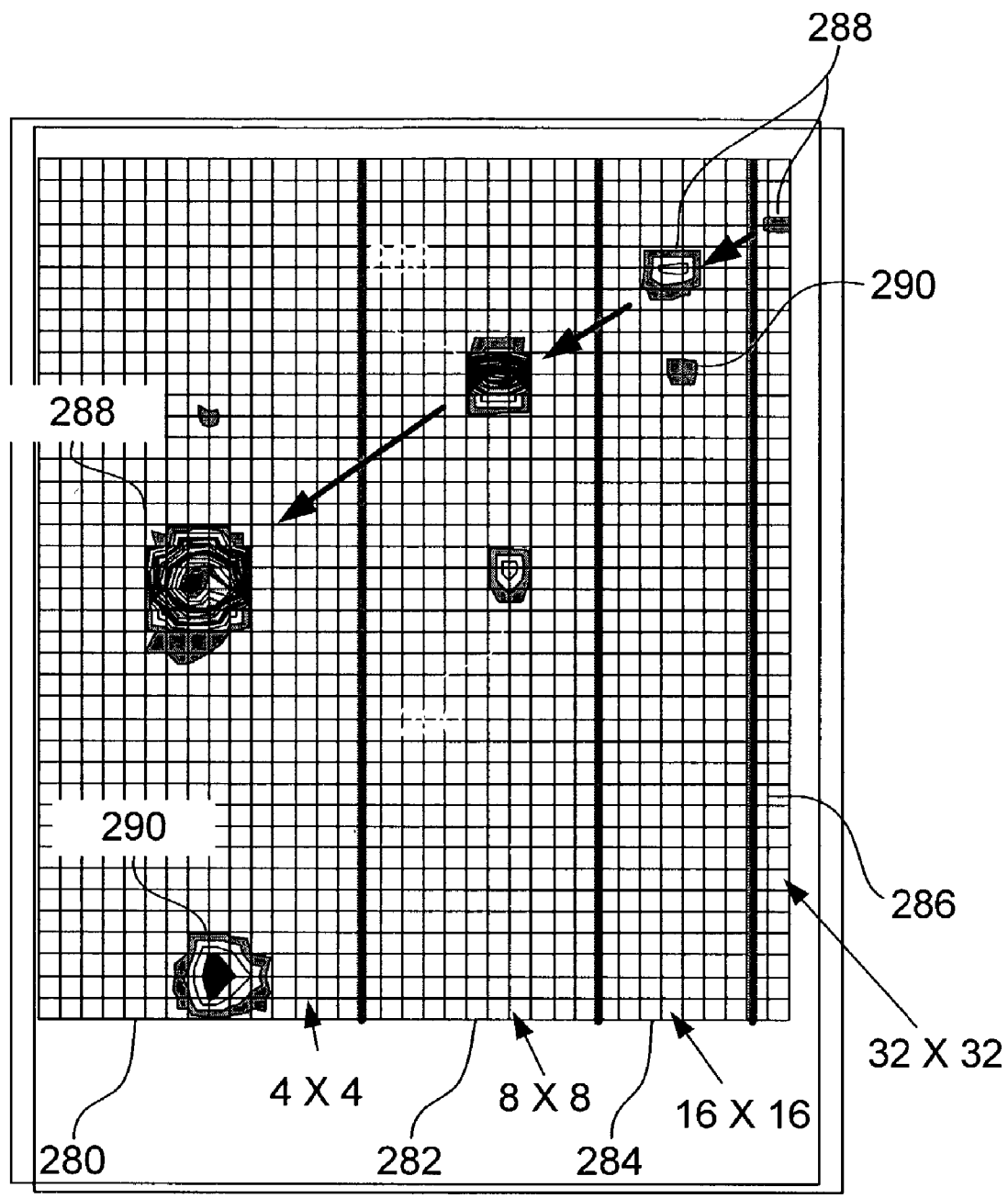
Figure 19:
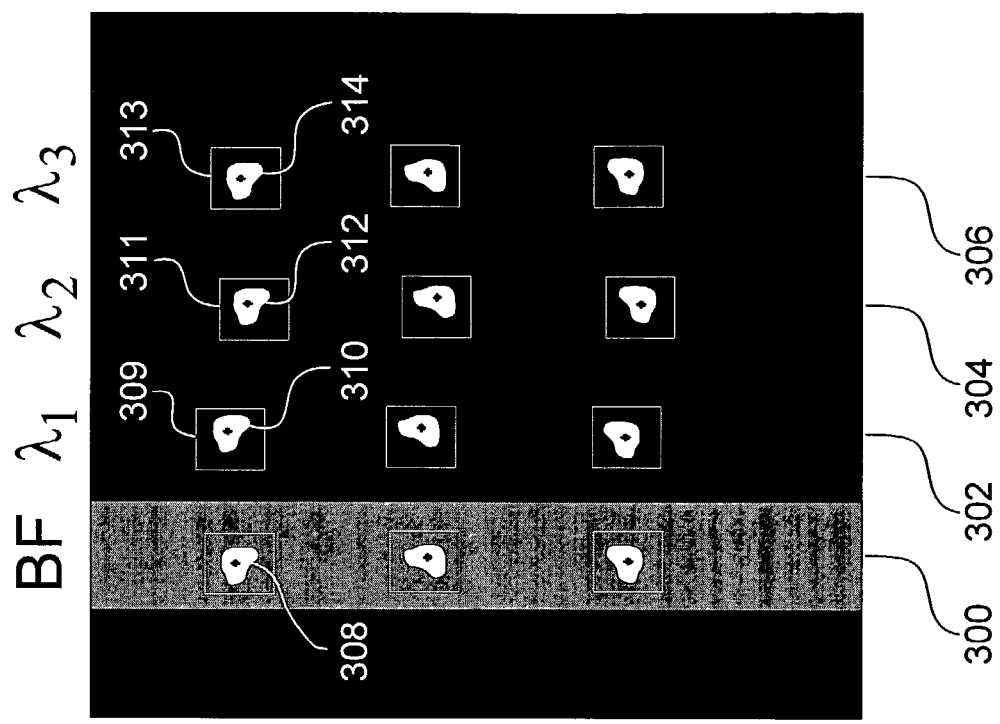
Figure 19:
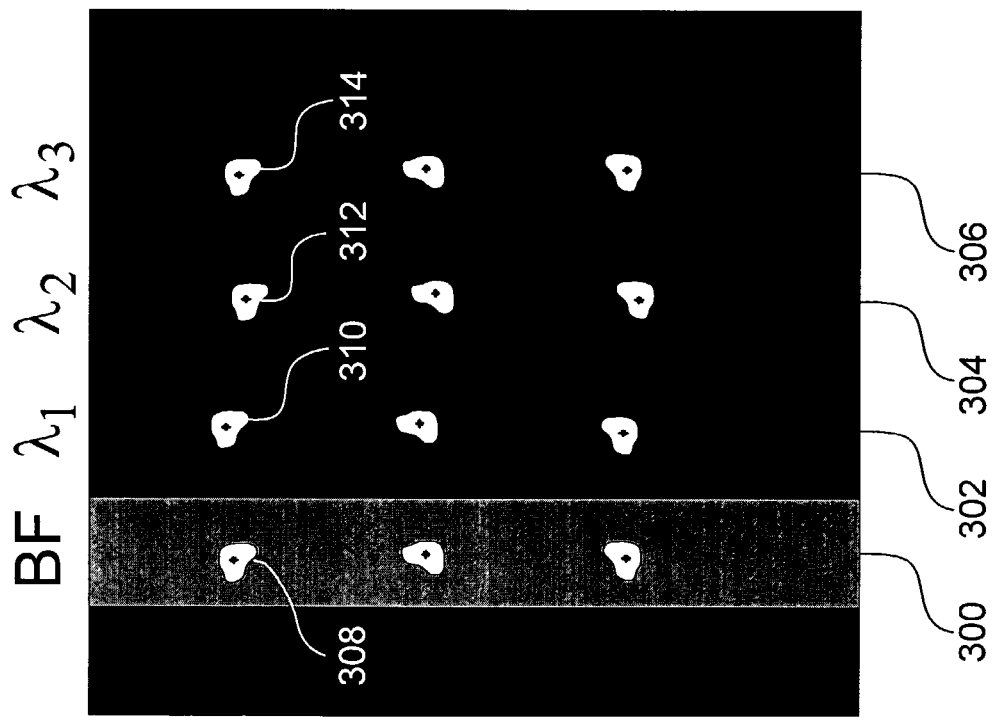
Figure 20:
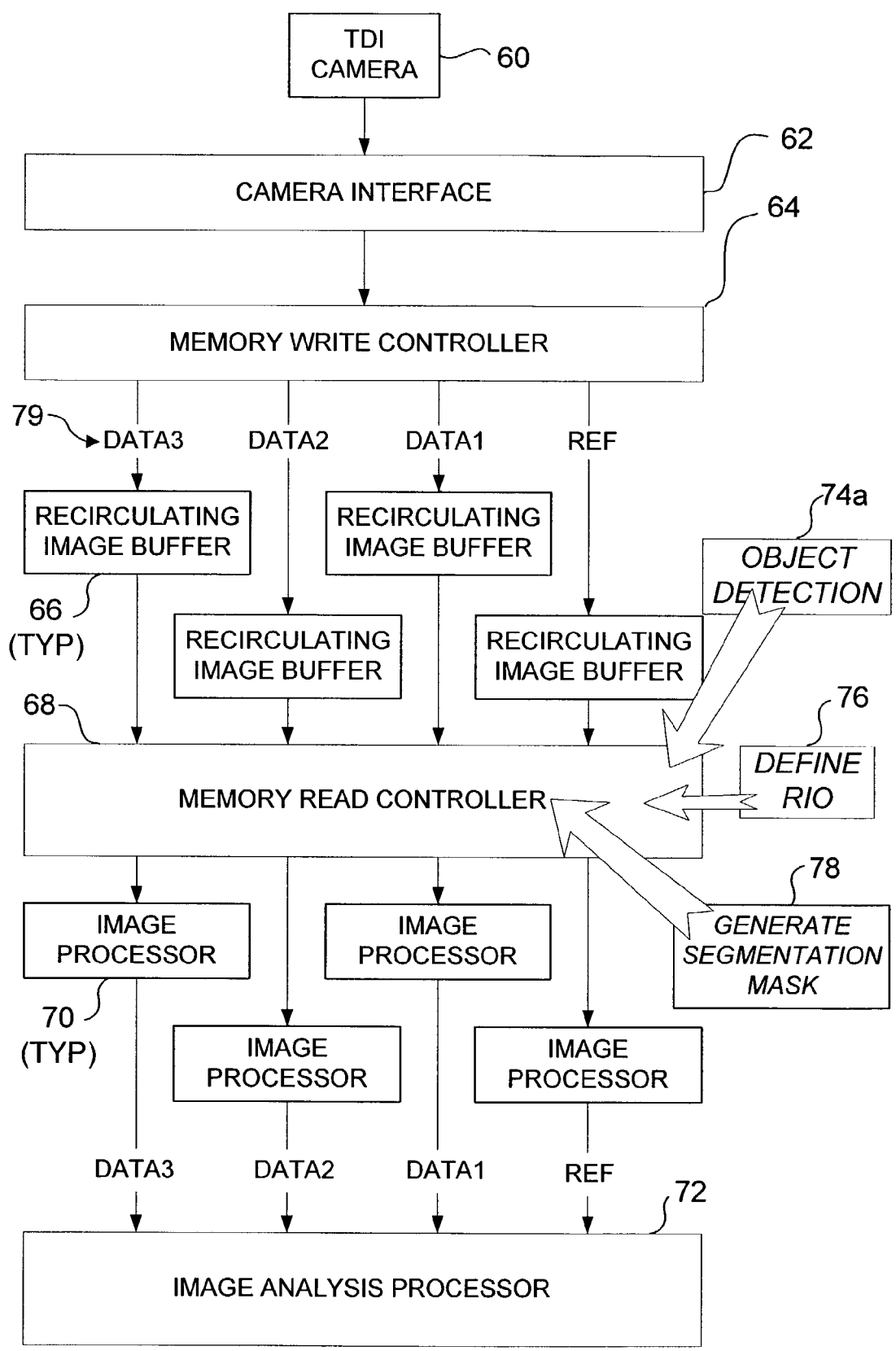
Figure 21:
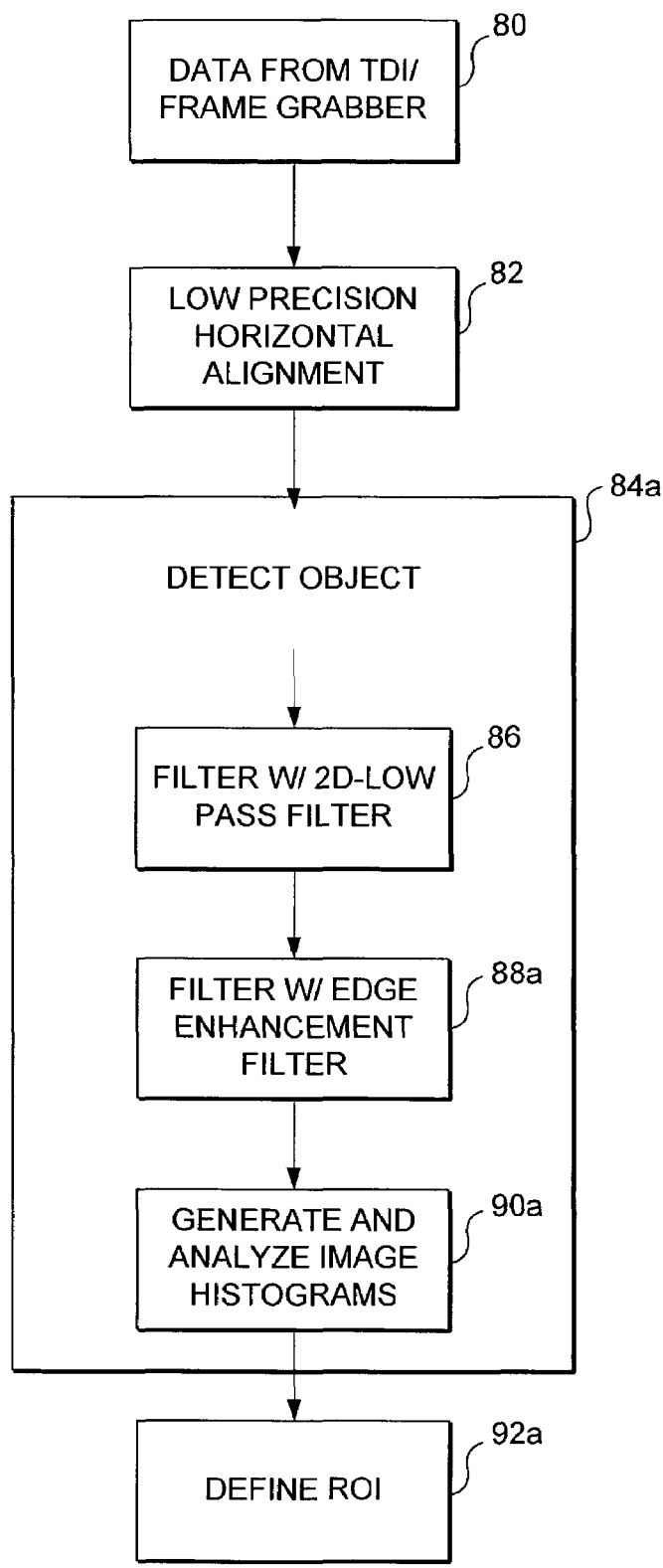
Figure 22:
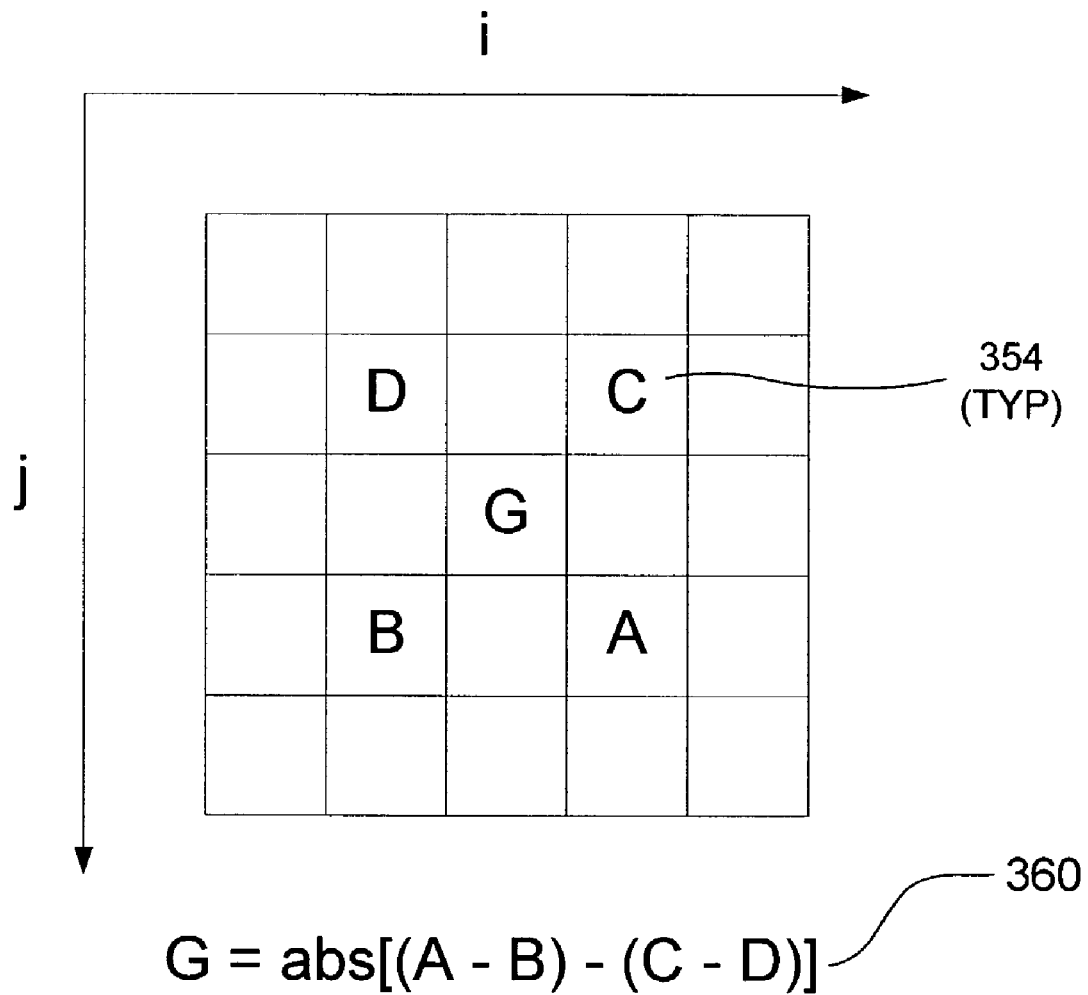
Figure 23:
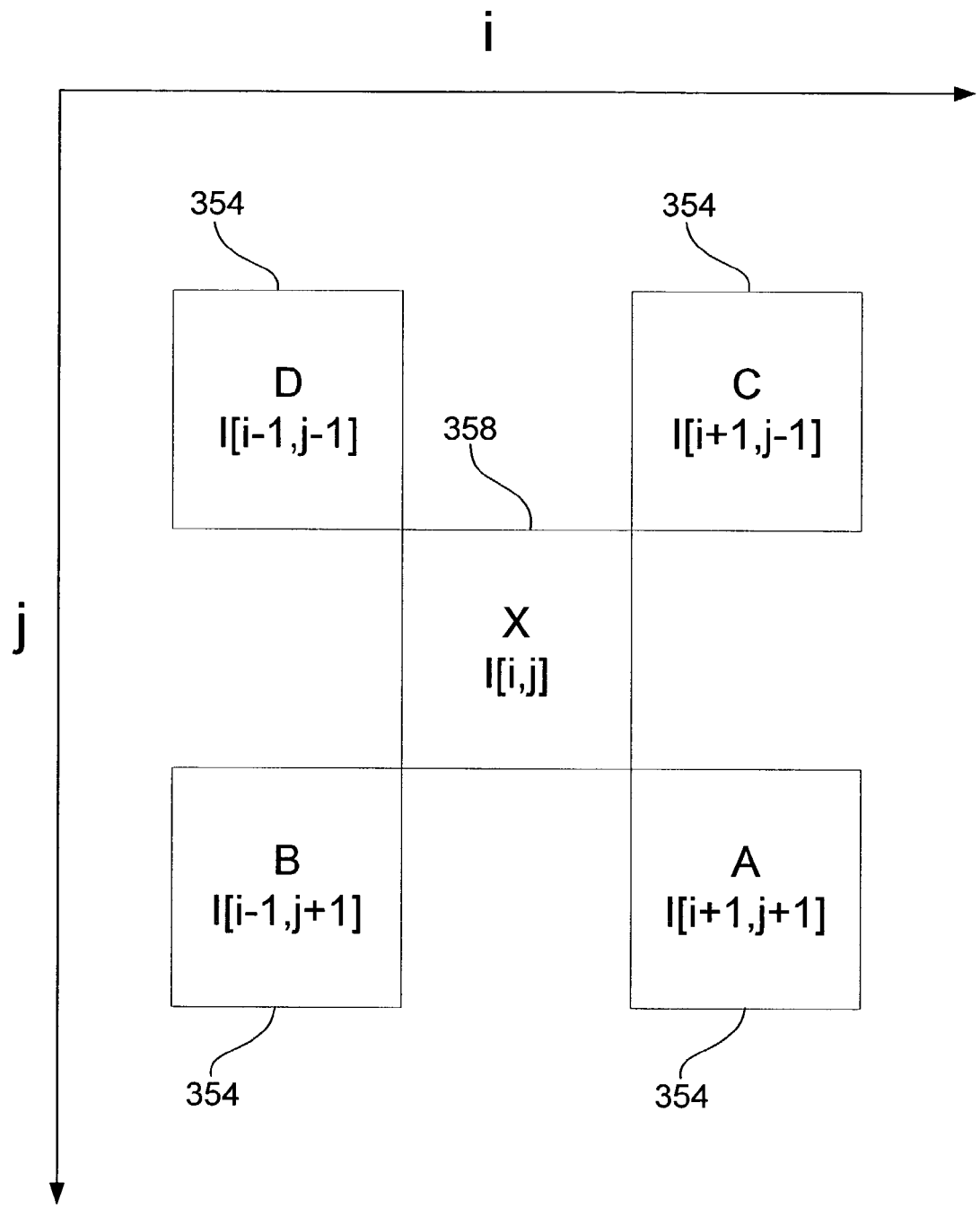
Figure 24:
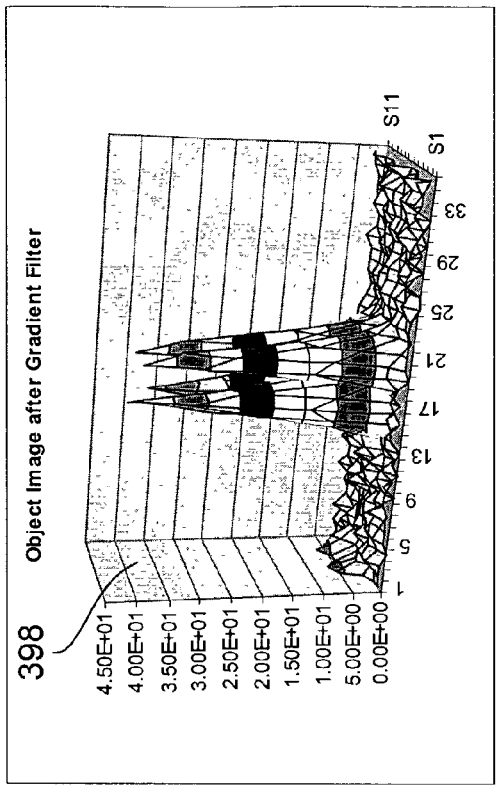
Figure 24:
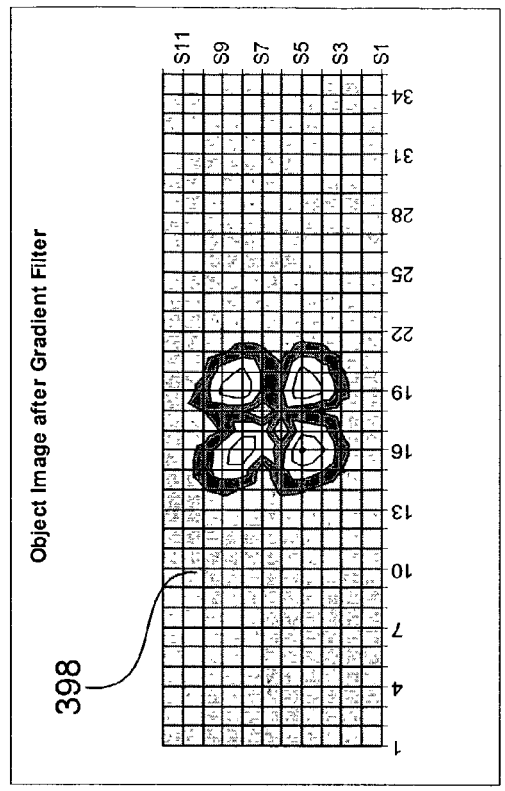
Figure 24:
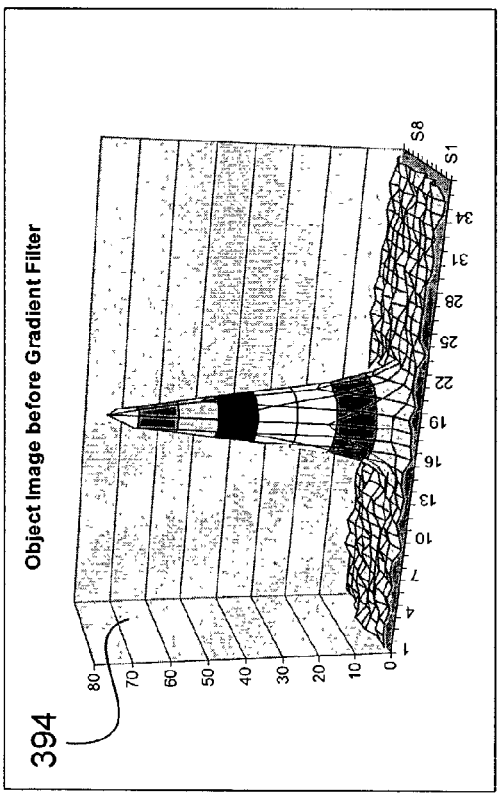
Figure 24:
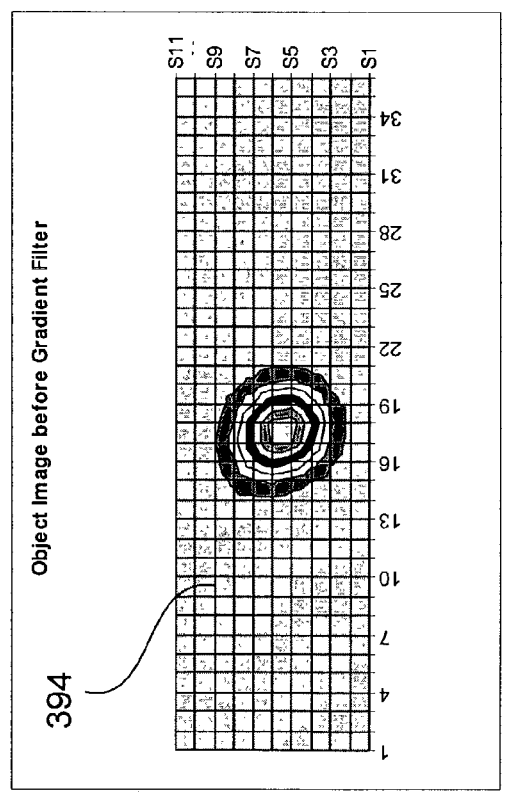
Figure 25A:
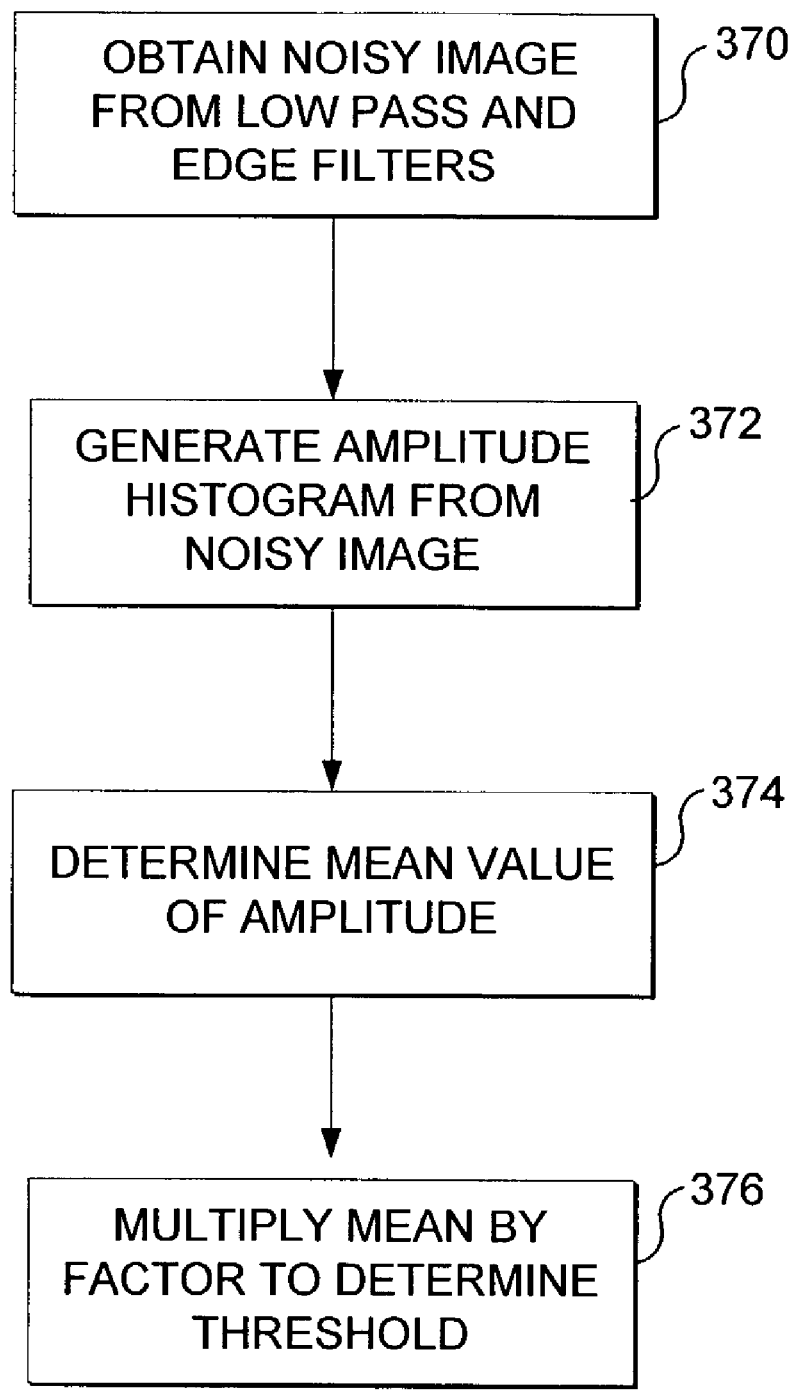
Figure 25B:
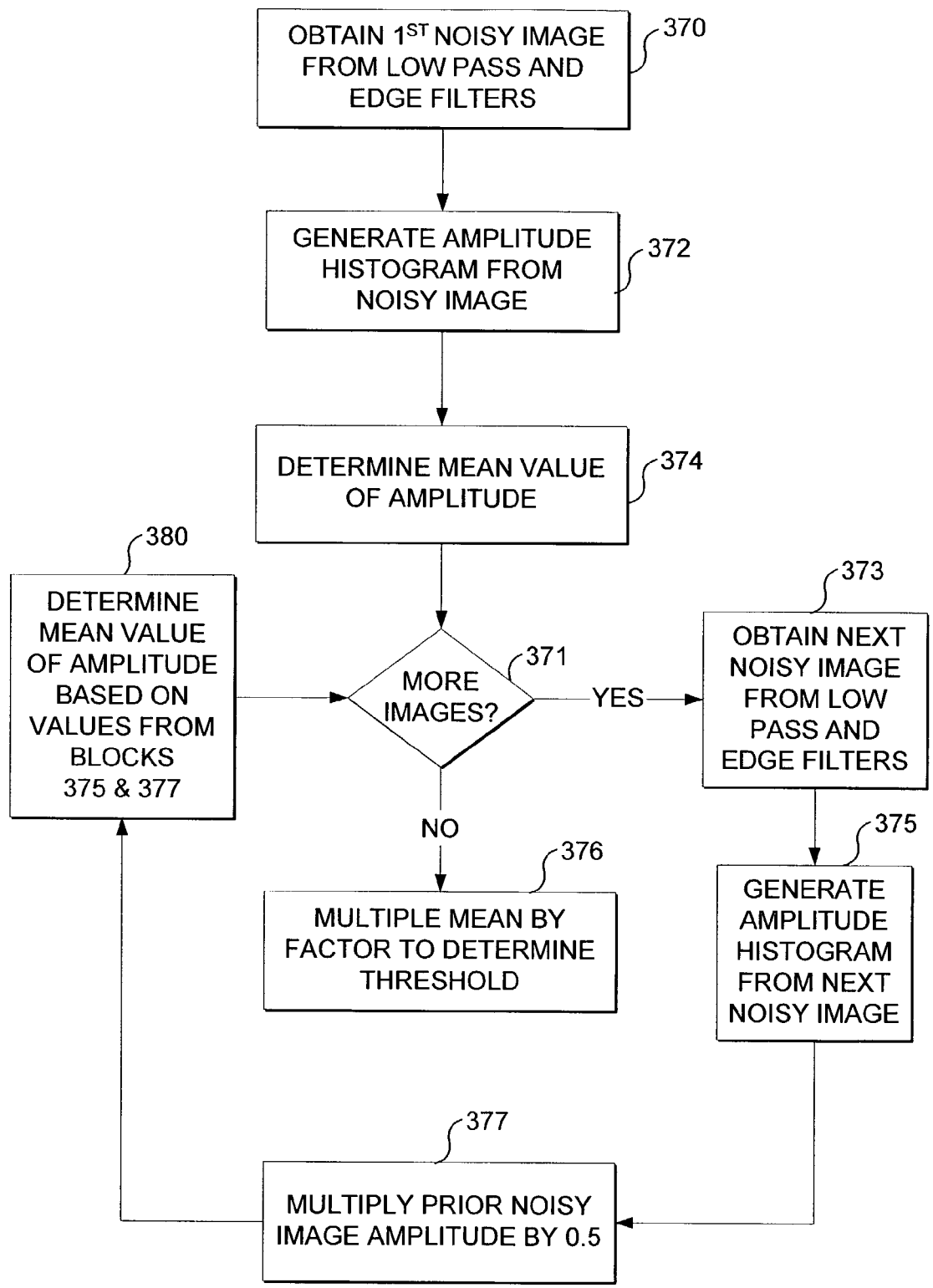
Figure 25C:
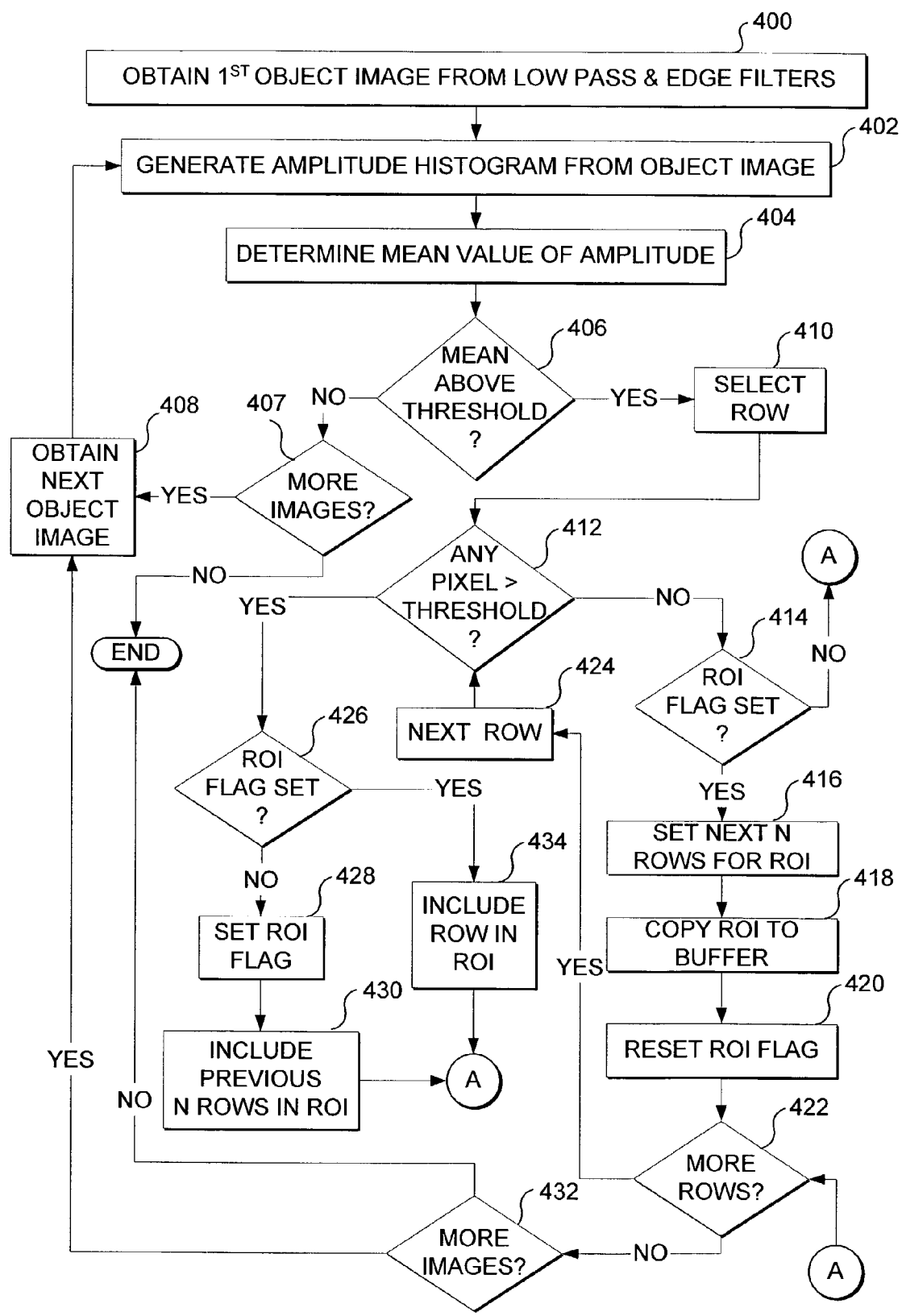
Figure 26:
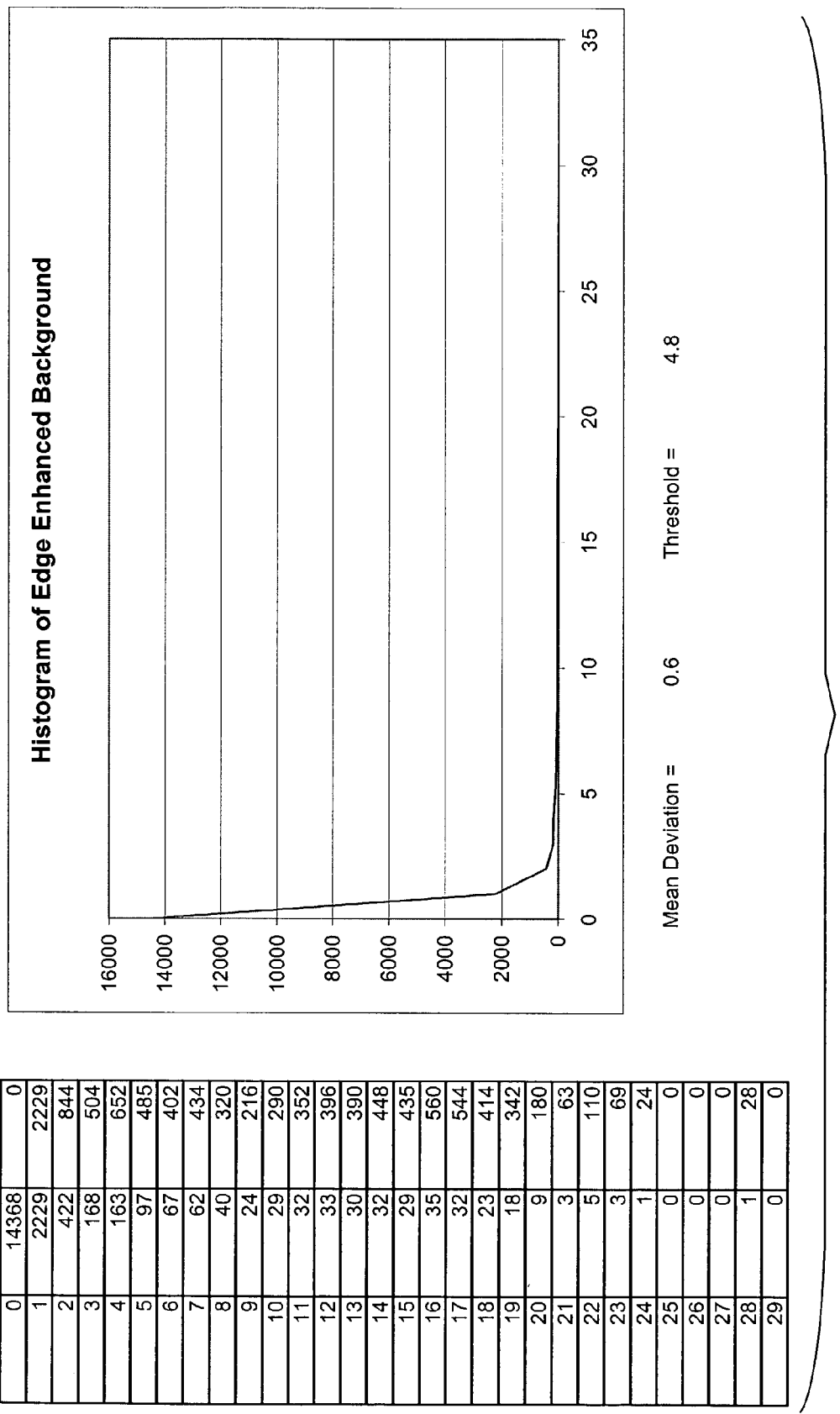
Figure 27:
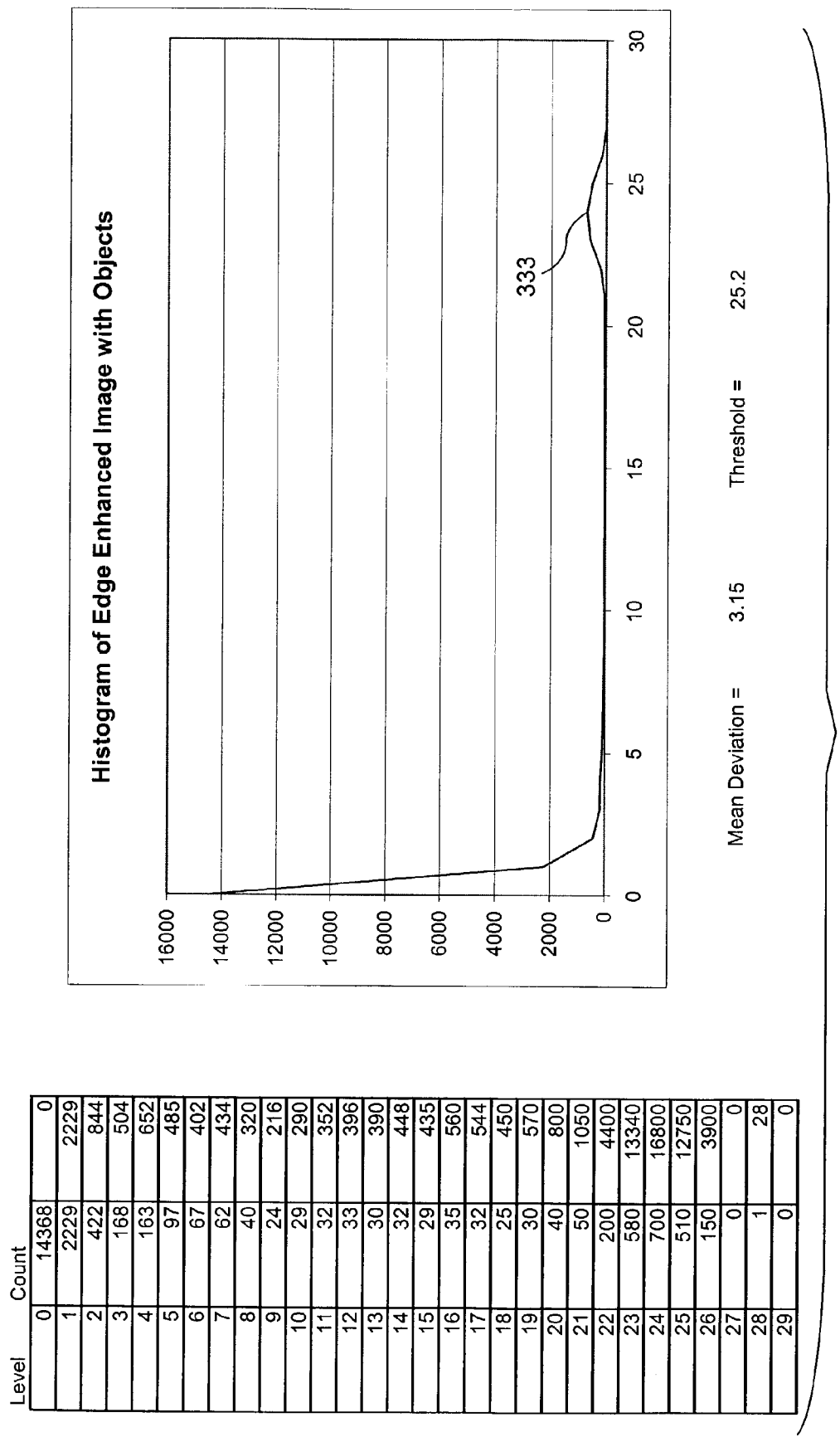
Figure 28:
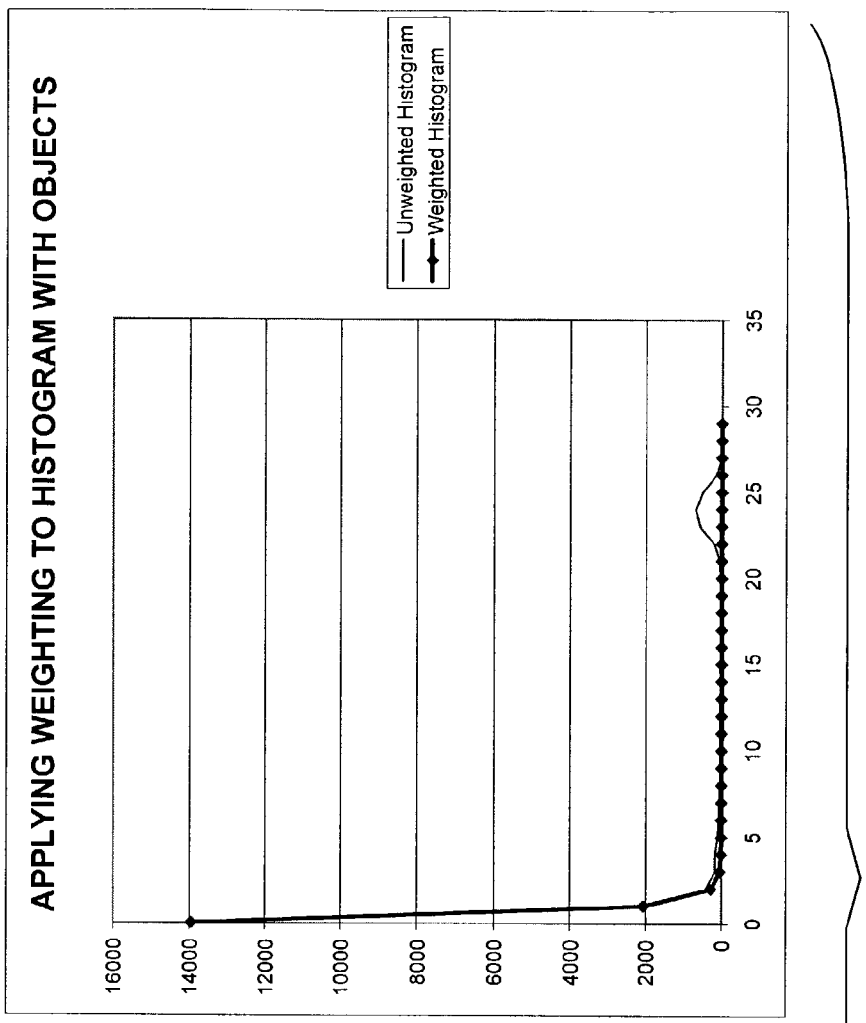
Figure 29A:
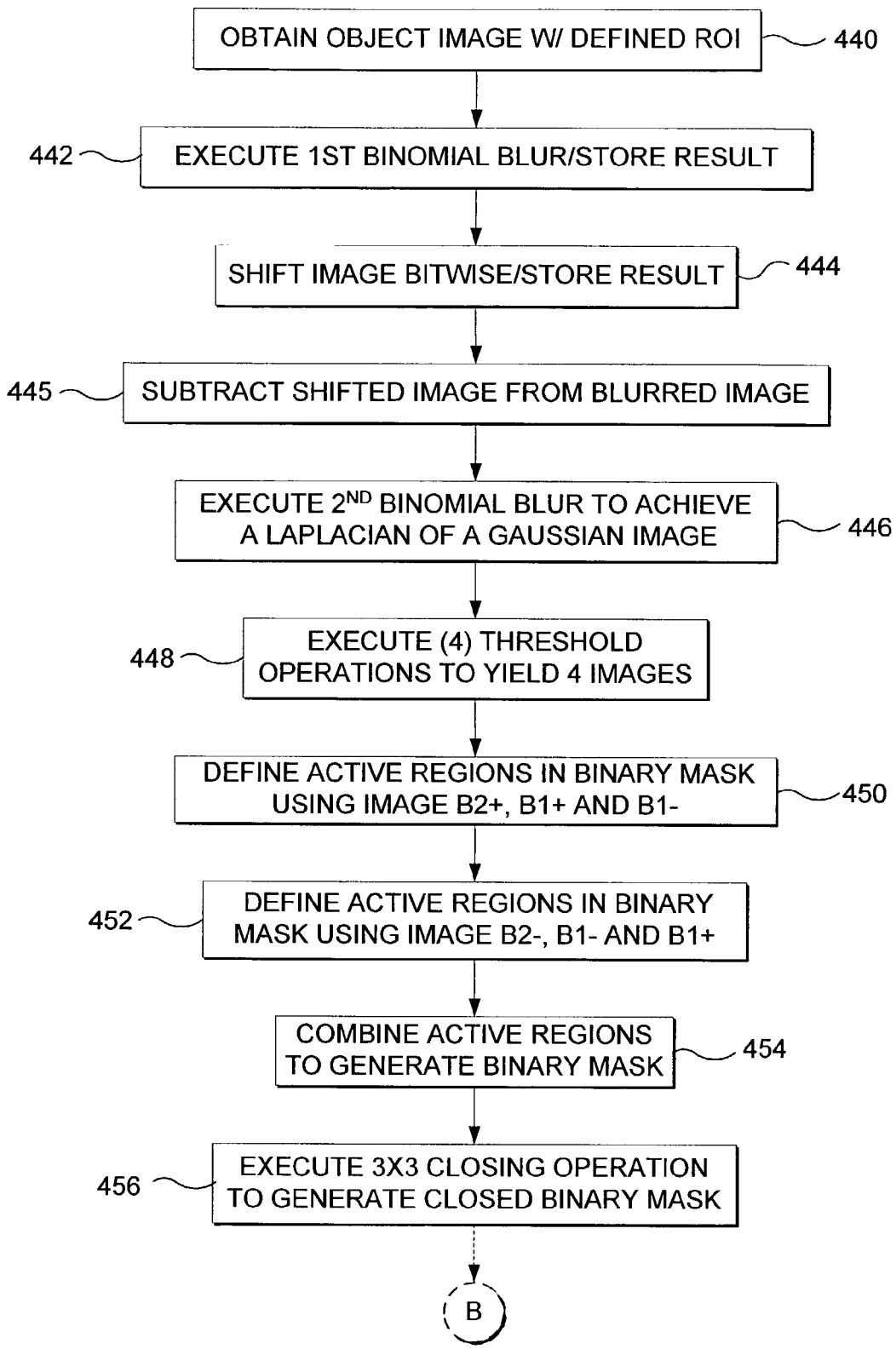
Figure 30:
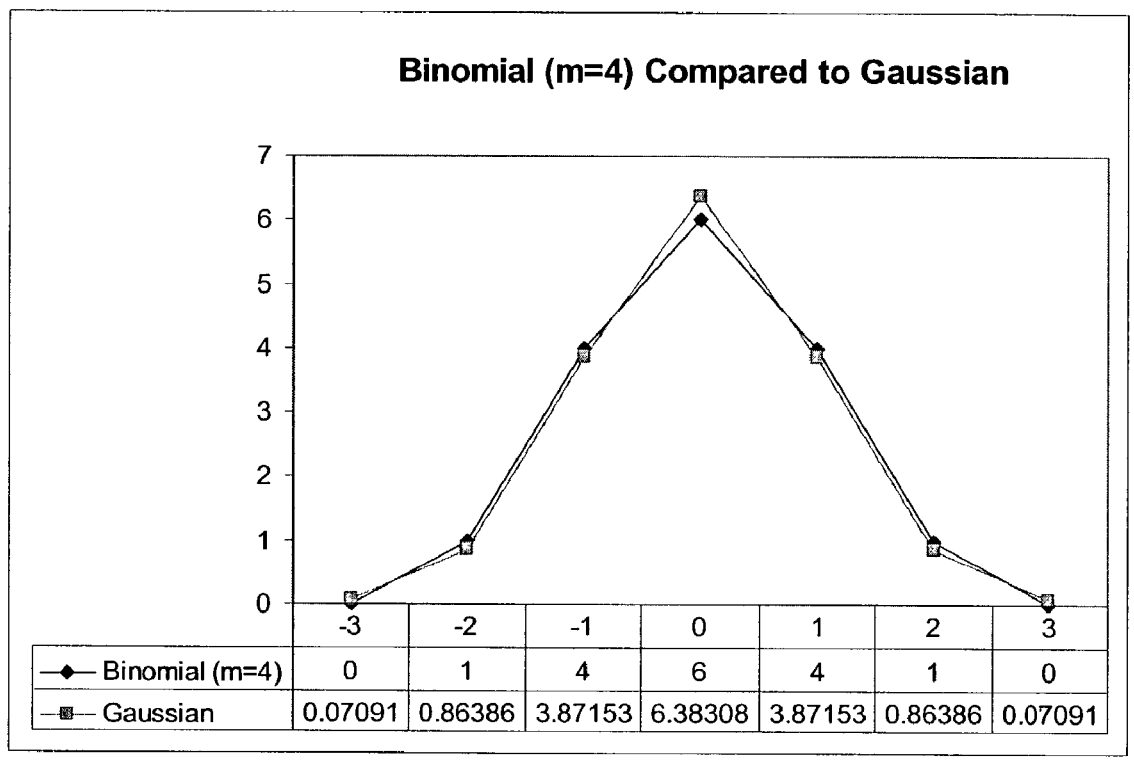
Figure 31:
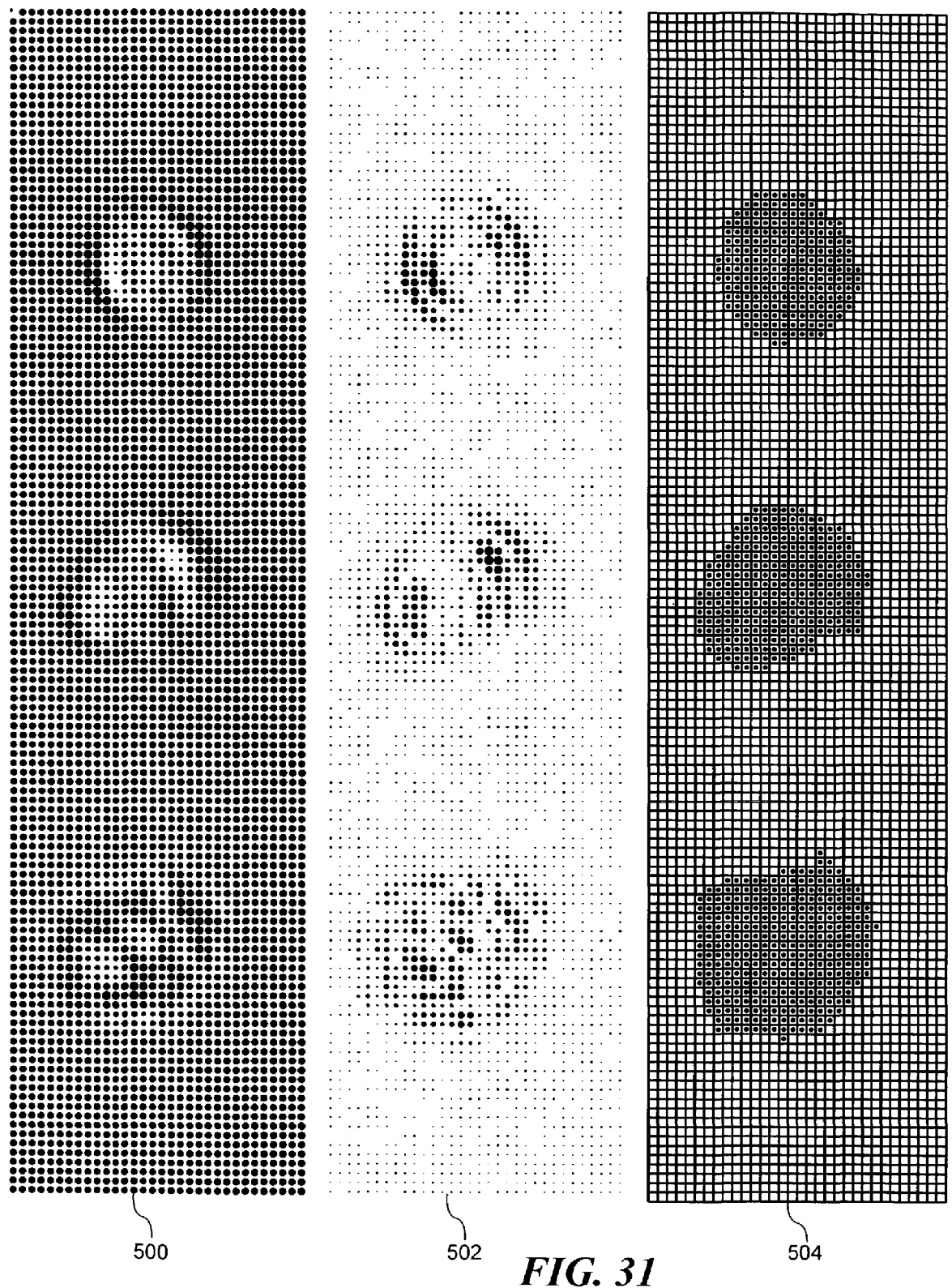
Figure 32:
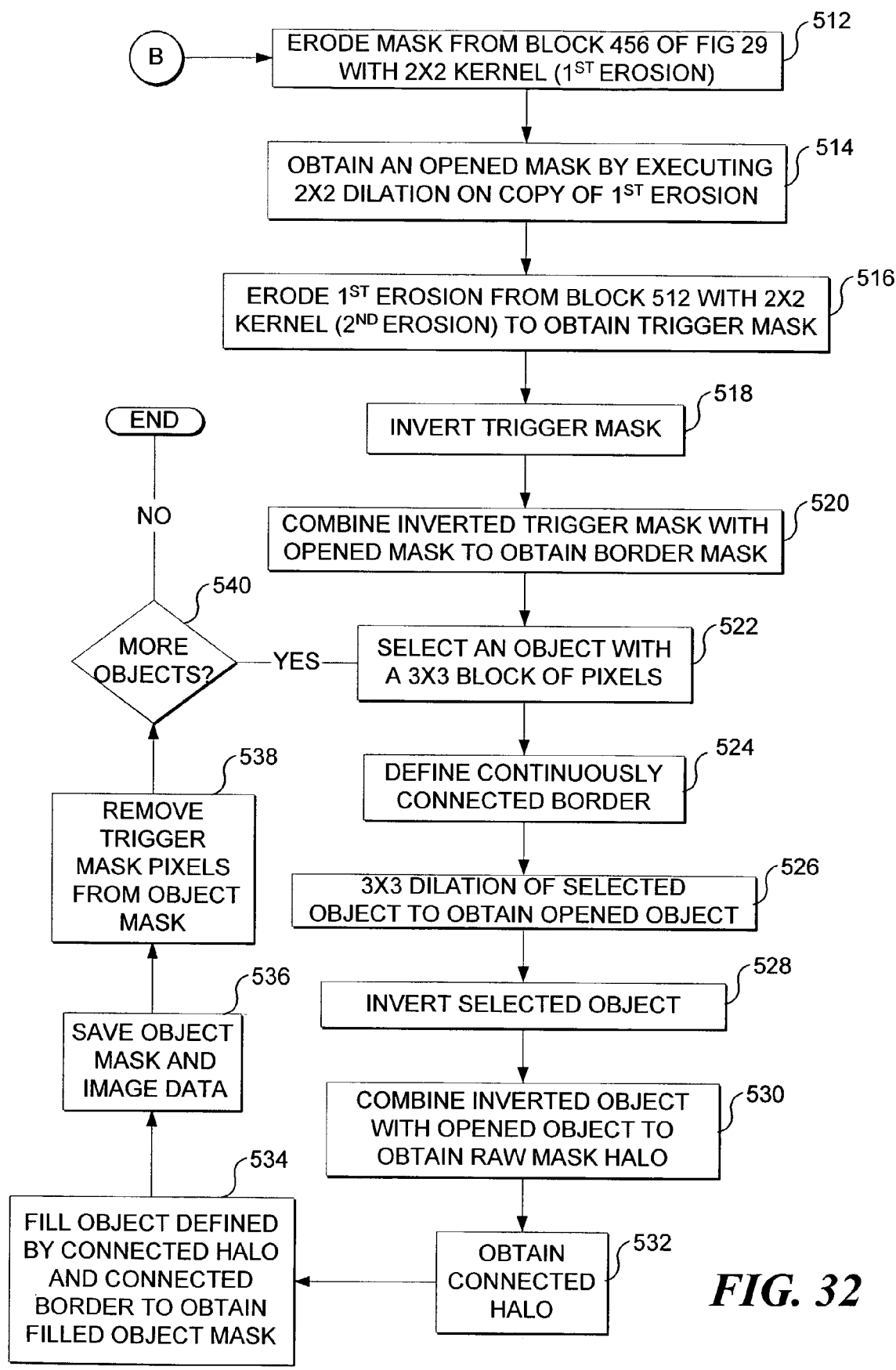
Figure 33:
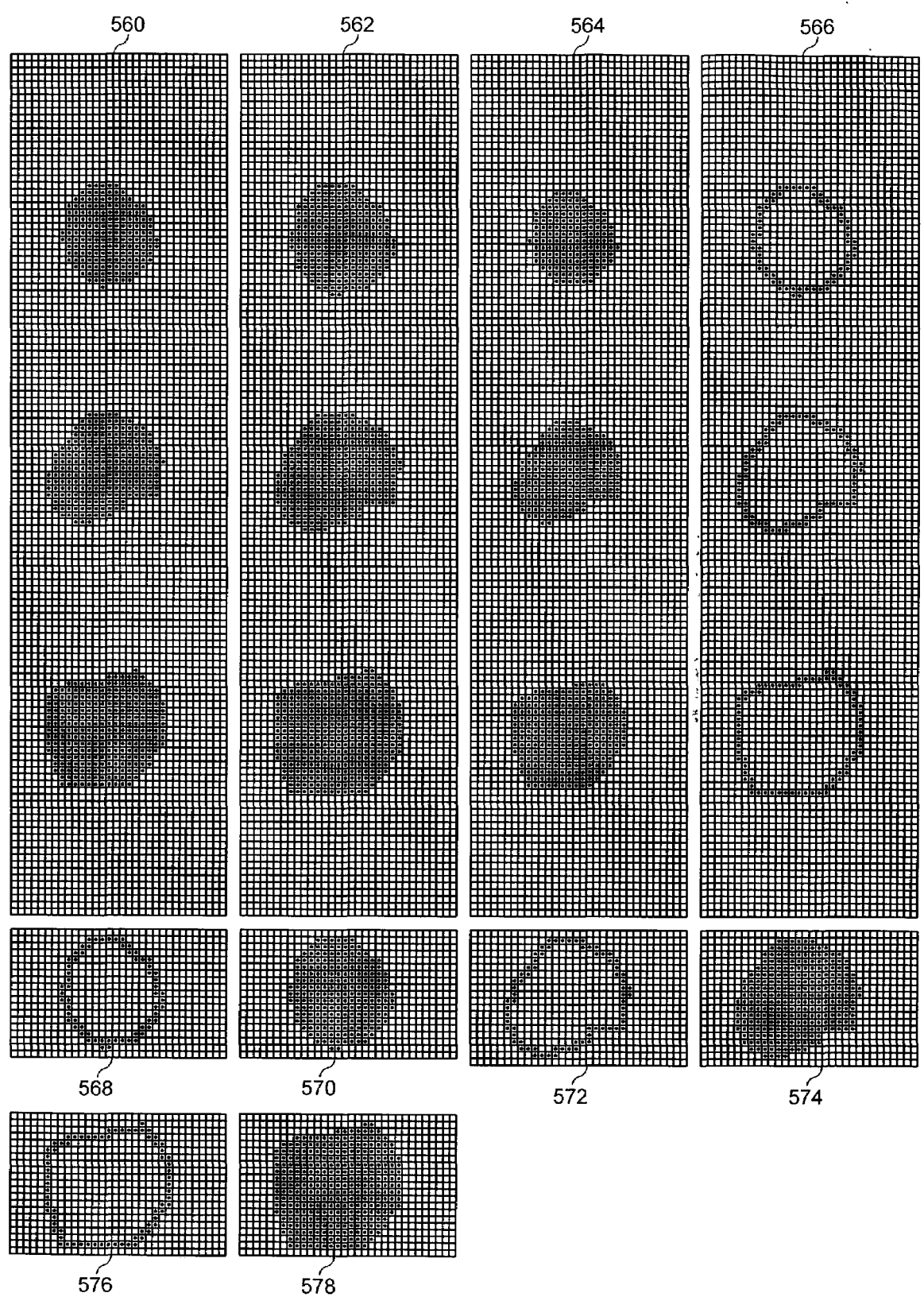

FIG. 7 schematically illustrates the concept of a recirculating row buffer;

FIG. 8 is a schematic diagram of the coordinate system of points and axes used in a gradient operator in accord with the present invention;

FIG. 9 schematically illustrates the gradient angles assigned to the coordinate system of points and axes as used in the gradient operator;

FIG. 10 schematically illustrates a hypothetical local gradient in one corner of the pixel locus for the gradient operator;

FIG. 11 schematically illustrates a hypothetical local gradient in one side of the pixel locus for the gradient operator;

FIG. 12 is a flow chart showing the steps employed to compute the value of a pixel using a gradient based edge enhancement filter;

FIG. 13 is a schematic diagram for operations of a grayscale transformation for noise rejection and channel-to-channel equalization;

FIG. 14 is a pictorial representation for modification of an image using two filter operations and a grayscale transformation in accord with the present invention;

FIG. 15 schematically illustrates the process of generating a plurality of low pass filtered and down sampled representations of a region of an image record;

FIG. 16 is a graphical representation of a surface plot of four filtered and down sampled representations of a region of an image record;

FIG. 17 is a flow chart showing the steps employed to locate the center of an object and to generate the boundaries of a region of interest (ROI) containing that object;

FIG. 18 is a graphical representation of a contour plot including four filtered and down sampled representations of the region of an image record as shown in FIG. 16;

FIG. 19 is a pictorial representation of the selection of ROIs in accord with the present invention, including the steps for selecting columns and correcting for channel-dependent vertical offsets;

FIG. 20 is a flow chart showing the steps used in a second embodiment of the segmentation process of the present invention;

FIG. 21 is a flow chart providing additional detail with respect to the object detection process of the second embodiment of FIG. 20;

FIG. 22 is a schematic diagram of the pixels used in the gradient filter, including the mathematical expression for the gradient filter;

FIG. 23 is a schematic diagram of the pixels used in the gradient filter, including nomenclature for addressing the pixels;

FIG. 24 is a pictorial representation of the transformation of an image of an isolated object to a gradient image of that object, by application of the gradient filter;

FIG. 25A is a flow chart of the steps used in a simplified process for setting a threshold for the object detector of the second embodiment;

FIG. 25B is a flow chart of the steps used in a somewhat more complex process for setting a threshold for the object detector of the second embodiment;

FIG. 25C is a flow chart of the steps used in the second embodiment of the invention, to analyze amplitude histograms of images to define ROIs;

FIG. 26 is a graphical representation of a histogram of pixel amplitudes for a locus of pixels selected from a gradient image and representing a region devoid of objects, including a table of corresponding histogram values;

FIG. 27 is a graphical representation of a histogram of pixel amplitudes for a locus of pixels selected from a gradient image containing at least one object, including a table of corresponding histogram values;

FIG. 28 is a graphical representation of a plot of the histogram of FIG. 27, modified by the application of weighting coefficients in accord with the present invention;

FIG. 29A is a flow chart of the steps used to extract object shapes from images and generate binary masks to indicate the pixels included in the objects, in accord with the first and second embodiments of the present invention;

FIG. 29B is a flow chart of the steps employed in manipulating two positive binary images and one negative binary image to generate a first portion of a binary mask;

FIG. 29C is a flow chart of the steps used in manipulating one positive and two negative binary images to generate a second portion of a binary mask;

FIG. 30 is a graphical representation showing how a binomial blur operation provides a reasonable approximation of a Gaussian distribution;

FIG. 31 is a pictorial representation of three images, a leftmost image representing original data delivered by the TDI camera, a middle image representing transformation of the original data by the LOG operation, and a rightmost image being a binary mask generated from the LOG-transformed image;

FIG. 32 is a flow chart of the steps used to find contiguous regions from the final mask and to create an object list for an image, with associated masks and other data; and FIG. 33 is a pictorial representation showing the effects of an application of the sequence of morphological operations of FIG. 32, to arrive at the final object-filled object masks.

DESCRIPTION OF THE PREFERRED EMBODIMENT

Overview of the Present Invention

An exemplary application of the present invention detects and delineates the boundaries of space occupied by objects of interest within a continuous stream of images provided by a flow imaging instrument. The present invention is preferably employed in conjunction with optical microscopes using the method of TDI to synchronize image formation with the traversal of particles or other objects (such as biological cells) through a measurement cavity. However, the present invention has more general application to images in which objects are presented in contrast to a background, independent of a specific physical mechanism used to create the image. It should thus be understood that application of the present invention to optical microscope-based flow imaging instruments employing TDI is intended to be exemplary, rather than limiting of the scope of application of the present invention. More generally, images may be obtained as a result of objects absorbing, reflecting, refracting, or scattering energy from a light source, and images may be constructed from energy radiated by objects through the mechanisms of fluorescence, phosphorescence, or radioactive decay. Furthermore, the present invention is not restricted to image-forming instruments that use visible light, but is also applicable to instruments that use other regions of the electromagnetic spectrum, acoustical waves, particle flux, and to measurements of other physical mechanisms, such as chemical reactivity, conductivity, size, shape, and mass.

Overview of a Preferred Imaging System

Figure 1:
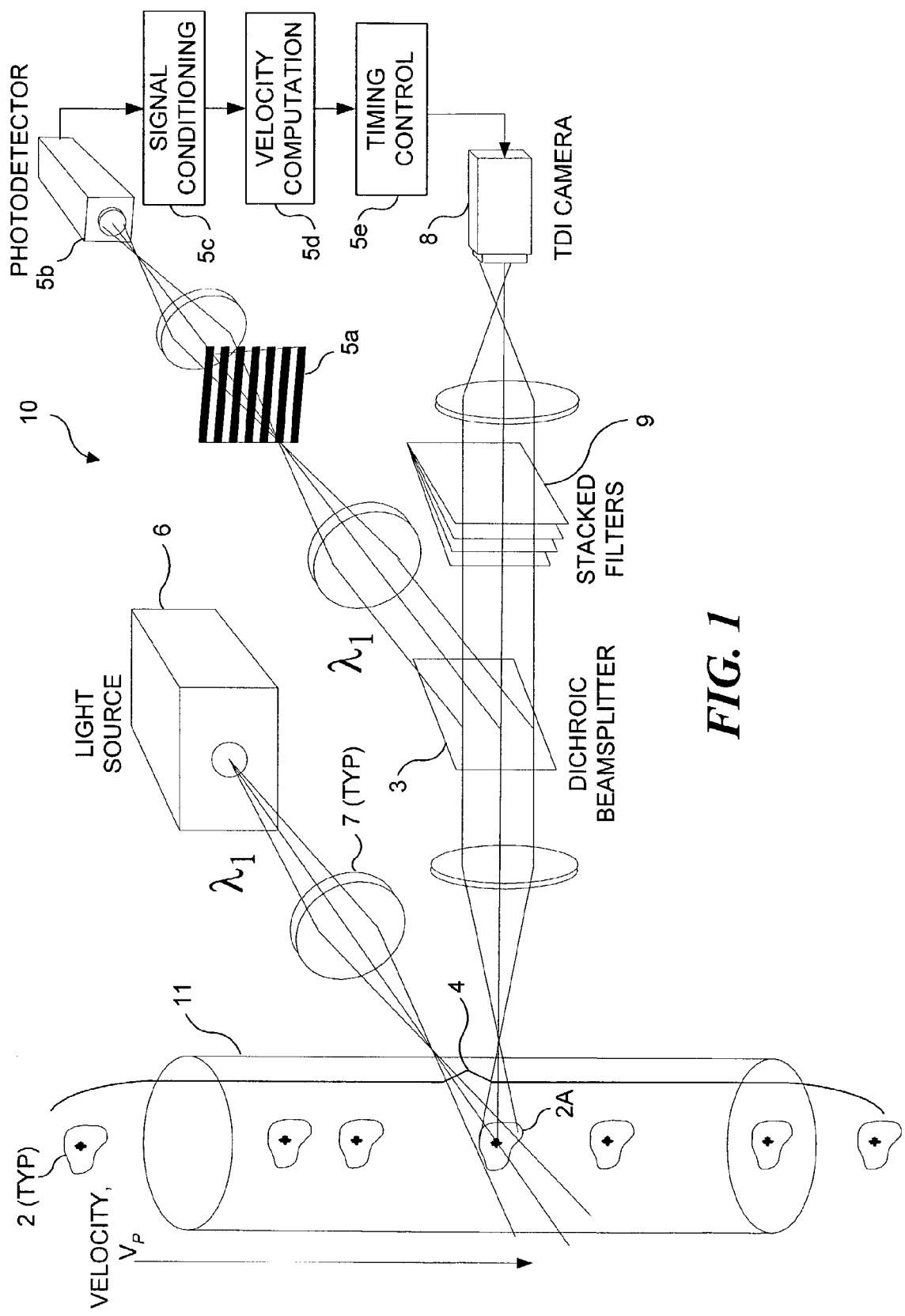
FIG. 1 is a schematic diagram of a flow imaging system incorporating a TDI detector, and a stacked filter assembly for separating the imaging channels by wavelength.

FIG. 1 is a schematic diagram of a preferred flow imaging system 10 that uses TDI when capturing images of objects 2 (such as biological cells), entrained in a fluid flow 4. System 10 includes a velocity detecting subsystem that is used to synchronize a TDI imaging detector 8 with the flow of fluid through the system.

Moving objects 2 are illuminated using a light source 6. The light source may be a laser, a light emitting diode, a filament lamp, or a gas discharge arc lamp, and the system may include optical conditioning elements such as lenses, apertures, and filters that are employed to deliver broadband or one or more desired wavelengths or wavebands of light to the object with an intensity required for detection of the velocity and one or more other characteristics of the object. Light from the object is split into two light paths by a beam splitter 3. Light traveling along one of the light paths is directed to the velocity detector subsystem, and light traveling along the other light path is directed to TDI imaging detector 8. A plurality of lenses 7 are used to direct light along the paths in a desired direction, and to focus the light. While not shown, a filter or a set of filters can be included to deliver to the velocity detection subsystem and/or TDI imaging detector 8, only a narrow band of wavelengths of the light corresponding to, for example, the wavelengths emitted by fluorescent or phosphorescent molecules in/on the object, or light having the wavelength(s) provided by the light source 6, so that light from non desired sources is substantially eliminated.

The velocity detector subsystem includes an optical grating 5a that modulates light from the object as a function of frequency, a light sensitive detector 5b (such as a photomultiplier tube or a solid-state photodetector), a signal conditioning unit 5c, a velocity computation unit 5d, and a timing control unit 5e that assures that TDI imaging detector 8 is synchronized to the flow of fluid 4 through the system. The optical grating preferably comprises a plurality of alternating transparent and opaque bars that modulate the light received from the object, producing modulated light having a frequency of modulation that corresponds to the velocity of the object from which the light was received. Preferably, the optical magnification and the ruling pitch of the optical grating are chosen such that the widths of the bars are approximately the size of the objects being illuminated. Thus, the light collected from cells or other objects is alternately blocked and transmitted through the ruling of the optical grating as the object traverses the interrogation region, i.e., the field of view. The modulated light is directed toward a light sensitive detector, producing a signal that can be analyzed by a processor to determine the velocity of the object. Thus, the velocity measurement subsystem is used to provide timing signals to TDI imaging detector 8.

Preferably, signal conditioning unit 5c comprises a programmable computing device, although an ASIC chip or a digital oscilloscope can also be used for this purpose. The frequency of the photodetector signal is measured, and the velocity of the object is computed as a function of that frequency. The velocity dependent signal is periodically delivered to a TDI detector timing control 5e to adjust the clock rate of TDI imaging detector 8. Those of ordinary skill in the art will recognize that the TDI detector clock rate is adjusted to match the velocity of the image of the object over the TDI detector to within a small tolerance selected to ensure that longitudinal image smearing in the output signal of the TDI detector is within acceptable limits. The velocity update rate must occur frequently enough to keep the clock frequency within the tolerance band as flow (object) velocity varies.

Beam splitter 3 has been employed to divert a portion of light from an object 2 to light sensitive detector 5b, and a portion of light from object 2a to TDI imaging detector 8. In the light path directed toward TDI imaging detector 8 there is a plurality of stacked dichroic filters 9, which separate light from object 2a into a plurality of wavelengths. Note that one of lenses 7 is used to form an image of object 2a on TDI imaging detector 8.

The theory of operation of a TDI detector, such as those employed in system 10, is as follows. As objects travel through a flow tube 11 (FIG. 1) and pass through the volume imaged by the TDI detector, light from the objects form images of the objects that travel across the face of the TDI detector. The TDI detector preferably comprises a charge coupled device (CCD) array, which is specially designed to allow charge to be transferred on each clock cycle in a row-by-row format, so that a given line of charge remains locked to or synchronized with a line in the image. The row of charge is clocked out of the array into a memory when it reaches the bottom of the array. The intensity of each line of the signal produced by the TDI detector corresponding to an image of an object is integrated over time as the image and corresponding resulting signal propagate over the CCD array. This technique greatly improves the signal-to-noise ratio of the TDI detector compared to non-integrating type detectors—a feature of great value when responding to images from low-level fluorescence emission of an object. Proper operation of the TDI detector requires that the charge signal be clocked across the CCD array in synchronization with the rate at which the image of the object moves across the CCD array. An accurate clock signal to facilitate this synchronization can be provided by determining the velocity of the object, and the present invention uses an accurate estimate of the object's velocity, and thus, of the velocity of the image as it moves over the CCD array of the TDI detector. A flow imaging system of this type is disclosed in commonly assigned U.S. Pat. No. 6,249,341, the complete disclosure, specification, and drawings of which are hereby specifically incorporated herein by reference.

Figure 2:
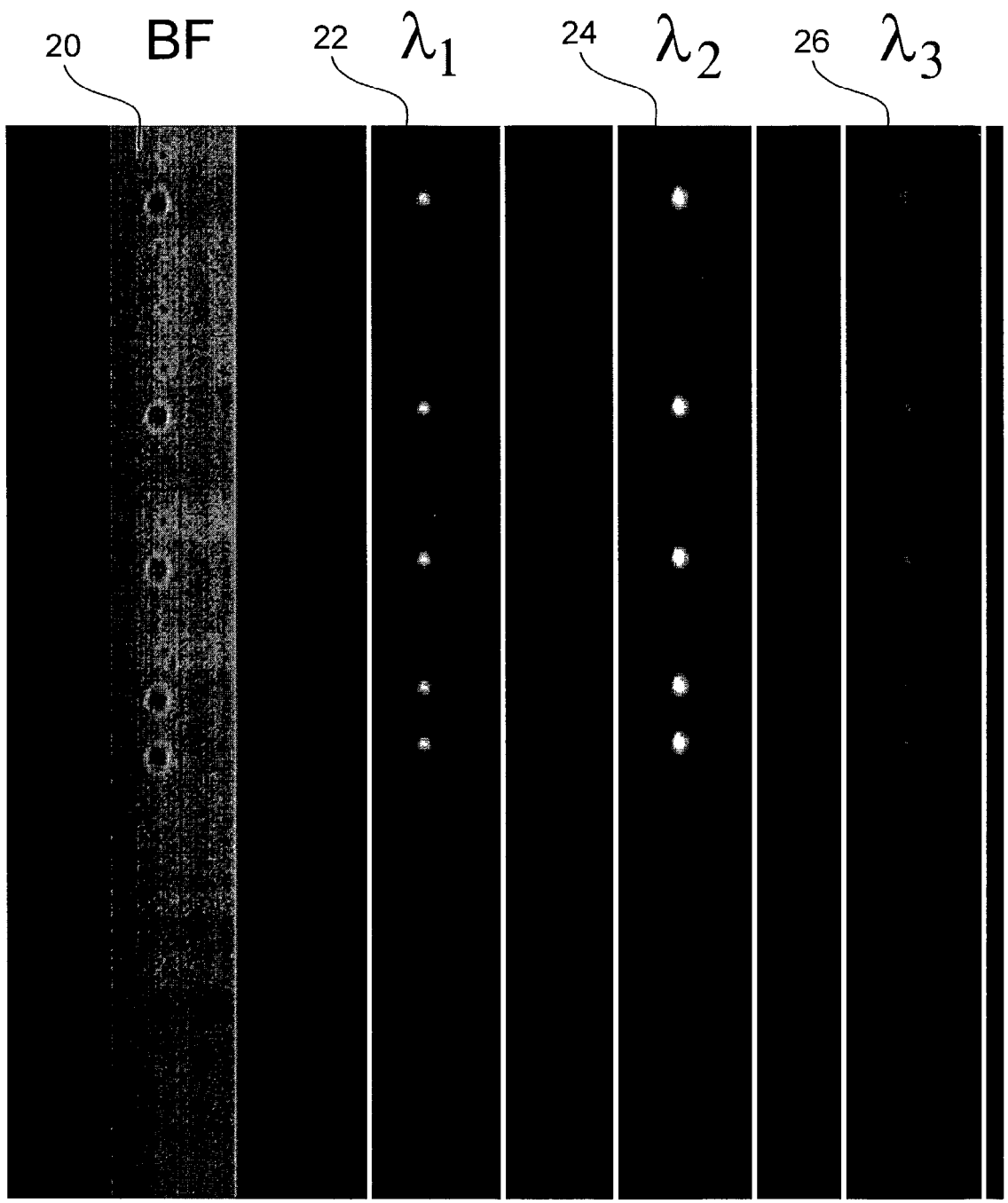
FIG. 2 is a pictorial representation of an image recorded by the flow imaging system of FIG. 1.

FIG. 2 is a pictorial representation of images produced by the flow imaging system of FIG. 1. A column 20, labeled "BF," includes images created by the absorption of light from light source 6 by spherical objects 2 entrained in fluid flow 4. The "BF" label refers to "brightfield," a term derived from a method for creating contrast in an image whereby light is passed through a region and the absorption of light by objects in the region produces dark areas in the image. The background field is thus bright, while the objects are dark. Thus, column 20 is the "brightfield channel." It should be understood that the inclusion of a brightfield image is exemplary, rather than limiting of the scope of the present invention. The remaining three columns 22, 24, and 26 shown in FIG. 2 are respectively labeled "$\lambda 1$," "$\lambda 2$," and "$\lambda 3$." These columns include images produced using light that has been emitted by an object entrained in the fluid flow. Preferably, such light is emitted through the process of fluorescence (as opposed to images produced using reflected light). As those of ordinary skill in the art will recognize, fluorescence is the emission of light (or other electromagnetic radiation) by a substance that has been stimulated by the absorption of incident radiation. Generally, fluorescence persists only for as long as the stimulating radiation persists. Many substances (particularly fluorescent dyes) can be identified based on the spectrum of the light that is produced when they fluoresce. Columns 22, 24, and 26 are thus referred to as "fluorescence channels."

Figure 3:
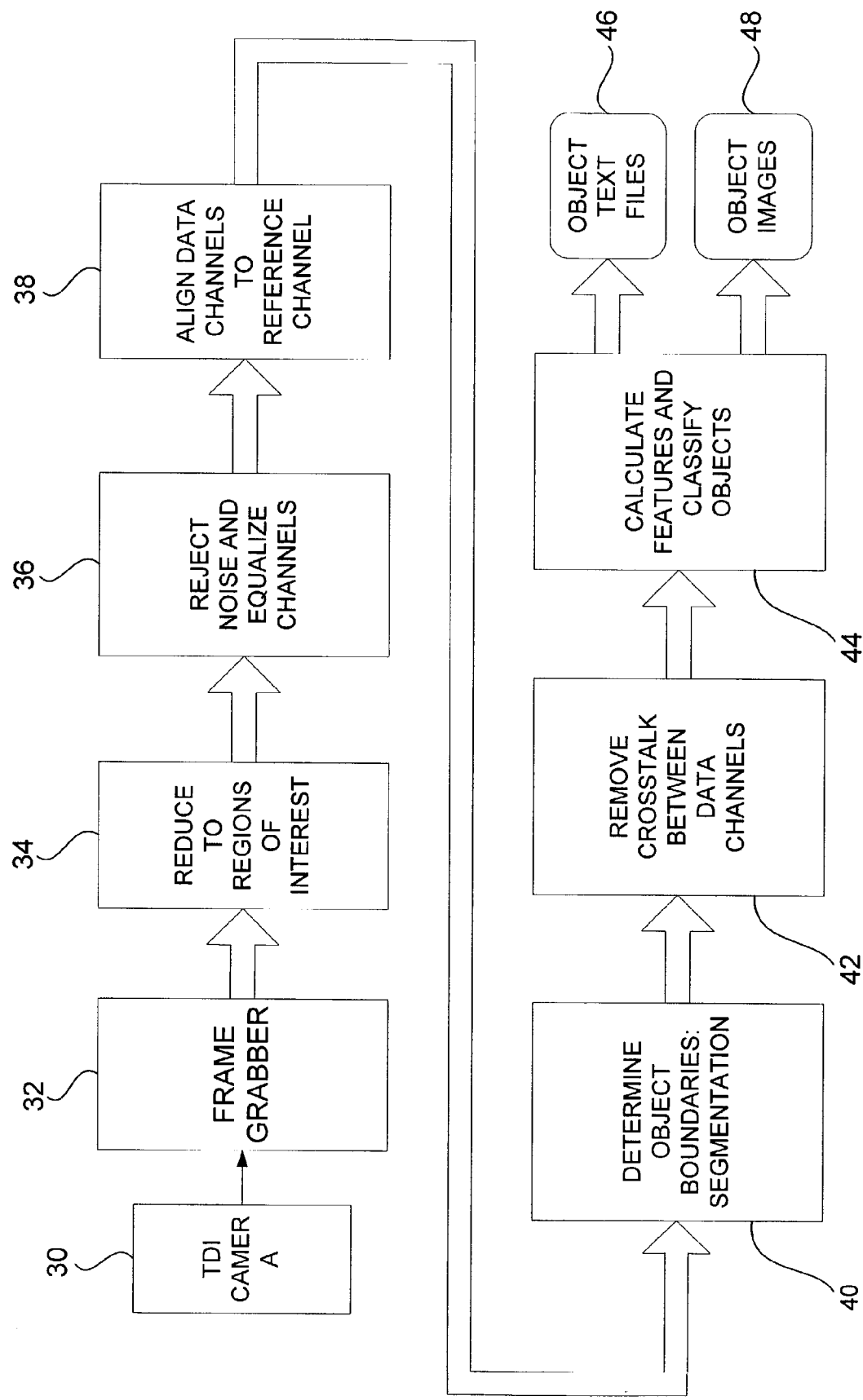
FIG. 3 is a flow chart showing the logical steps used in the segmentation process of the present invention.

The present invention preferably employs the brightfield channel to extract the outer boundaries of the objects of interest. The process of identifying the pixels falling inside the object boundaries is referred to as "object segmentation." The object segmentation of the present invention is particularly well adapted for use in the automated acquisition and computation-based analysis of images to extract information. FIG. 3 is a flow chart showing the basic steps of the segmentation process in the present invention, which is preferably employed in conjunction with an image acquisition system, such as that depicted in FIG. 1. Referring to FIG. 3, a first step indicated in a block 30 is the acquisition of an image from a TDI camera (such as TDI detector 8 of FIG. 1). Images from such a TDI camera are captured by an electronic frame grabber in a block 32. Preferably, such an electronic frame grabber includes electronic elements for receiving signals from a TDI camera and conveying those signals to an image processor that executes the steps described below.

In a block 34, the image processor manipulates the data signals from the frame grabber to reduce the signal to the ROI. Typically, the images of objects carried in a flow stream occupy a small fraction of the total space depicted in an image record. Computation time is reduced without loss of information about the objects by discarding the majority of the pixels in the image record that depict only the background space against which the objects are imaged. In block 34, the image processor is reducing the size of the image record to individual ROIs corresponding to object images. Each ROI is preferably sufficiently large to include the complete image of an object and a collection of surrounding background pixels. The number of surrounding pixels retained in an ROI of an object is chosen by evaluating the accuracy that can be expected in the estimates of the size and location of the object. More precise localization and size estimation allows reduction in the number of surrounding pixels carried in the ROI.

Figure 4A:
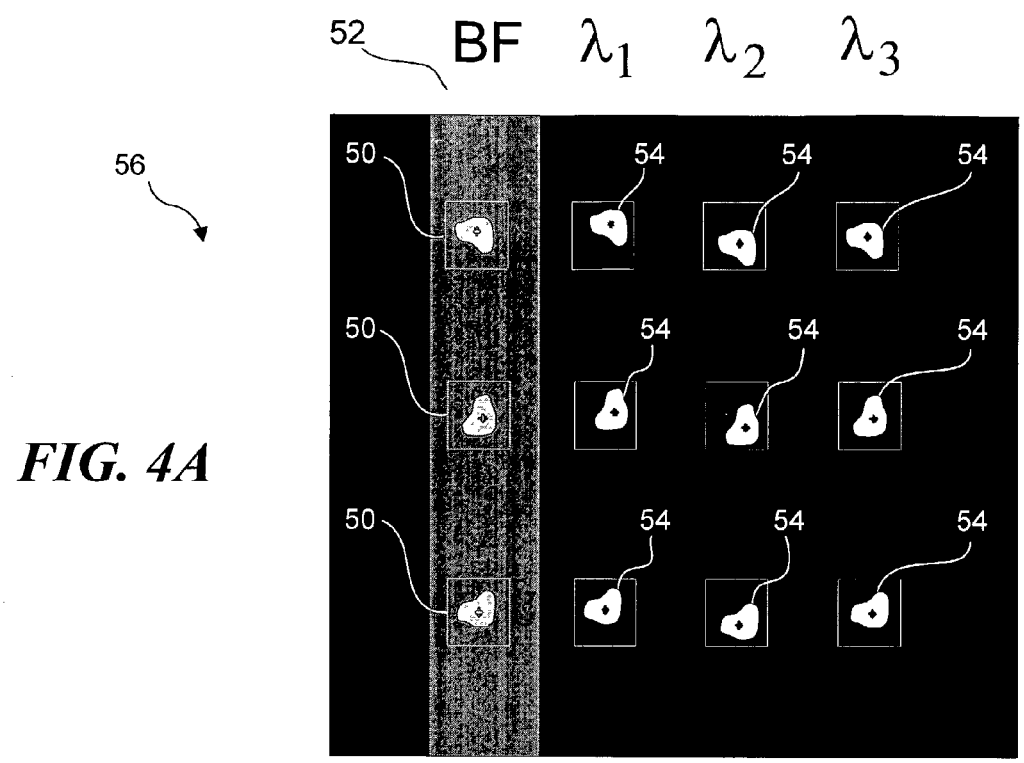
FIG. 4A is a pictorial representation of an image record being segmented into regions of interest associated with each object in the image record, to reduce an amount of background pixels associated with each object in the image record.
Figure 4B:
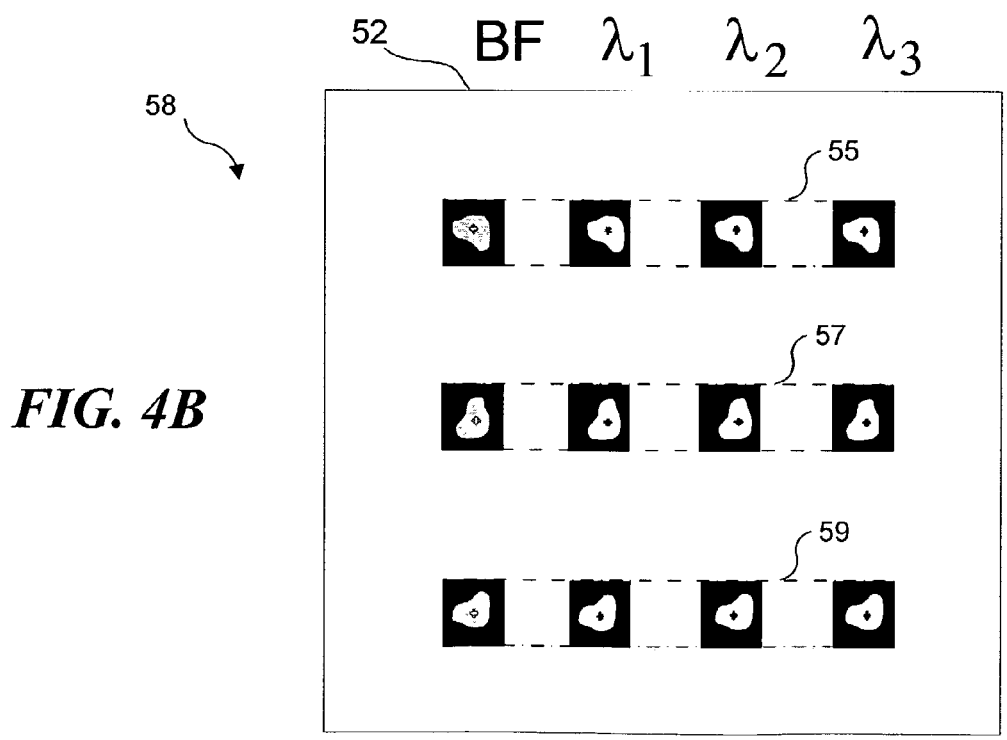
FIG. 4B is a pictorial representation of a processed image record containing a reduced amount of background pixels associated with each object in the image record.

FIG. 4A is a pictorial representation of the reduction of an image record 56 into ROIs that contain object images and a minimal amount of background pixels. FIG. 4B is a pictorial representation of an image record 58 that contains a minimal amount of background pixels (note the shaded regions). FIGS. 4A and 4B are similar to FIG. 2; in that each is a pictorial representation of an image recorded by a flow imaging system, and each includes a brightfield channel 52, and three fluorescent channels $\lambda_1$, $\lambda_2$, and $\lambda_3$.

FIG. 4A corresponds to block 34 of FIG. 3. A ROI 50 is defined using the brightfield image, and that ROI is applied to images 54 in each of the fluorescent channels. Image record 58 of FIG. 4B represents a segmentation mask developed from the analysis of the brightfield ROIs, used to define the images of objects 55, 57, and 59 in both the brightfield and fluorescent channels. Clearly, the amount of background pixels in image record 58 is significantly reduced. An astute observer may notice that additional steps, beyond reducing the image record to specific ROIs associated with each object, have been executed to obtain image record 58. For example, the objects in the channels have been equalized and aligned. Such additional steps correspond to blocks 36 and 38 of FIG. 3.

Referring once again to FIG. 3, note that the sensitivity, gain, and signal-to-noise ratio of each channel in the imaging instrument are determined in part by characteristics unique to that channel. Therefore, the step of equalizing the signals in the channels is performed in block 36. This equalization process preferably encodes the most useful information in each channel into a restricted number of bits of a digital word. The number of bits is restricted to reduce the amount of electronic memory needed to store the image information and to reduce the number of operations required in the image analysis computations. As part of the equalization process, bits carrying only noise are eliminated from the encoded information.

Although a preferred image acquisition instrument will maintain the alignment of the four imaging channels, some mis-registration of the images of an object can be expected. Therefore, in block 38, images of objects in the image record are aligned with one another, which ensures that the object boundaries (i.e. ROI 50 of FIG. 4A) defined by the segmentation of the brightfield image (block 34 of FIG. 3) can be accurately applied to the images from the fluorescence channels. Following the alignment operation in block 38, computational methods are applied in a block 40 to determine the outer boundary of each object (i.e., of objects 55, 57, and 59 of FIG. 4B). This operation is fundamental to the identification of characteristic features for such objects.

In a block 42, a crosstalk removal operation is performed. This operation is preferably performed in each channel by the application of a computational algorithm that removes information from the channel that should be only in an adjacent channel.

After the crosstalk correction, the results of feature calculation and object classification are combined in a block 44. Pattern recognition methods are used to identify features and objects. Such pattern recognition processes can be used to classify objects into types that are significant for solving specific problems, such as those commonly encountered in medical diagnosis and biomedical research.

The output of the feature calculation and object classification operations of block 44 include both text files, as indicated by a block 46, and image files, as indicated in a block 48. The text files preferably convey information extracted from the segmentation, feature calculation, and object classification operations, and the images files represent the objects, properly aligned, and with a minimal amount of background pixels associated with each object.

Important steps of the present invention are: (a) reducing the image space into ROIs; (b) reducing noise and equalizing the channels; and (c) segmenting the object images, as described above in conjunction with blocks 34, 36, and 40, respectively. The operations of image acquisition (block 30), frame grabbing (block 32), aligning data to a reference channel (block 38), removing crosstalk (block 42), and feature calculation and object classification (block 44) can be accomplished using a variety of different techniques. Many exemplary techniques are described in commonly assigned issued patents and pending patent applications.

First Preferred Embodiment

Figure 5:
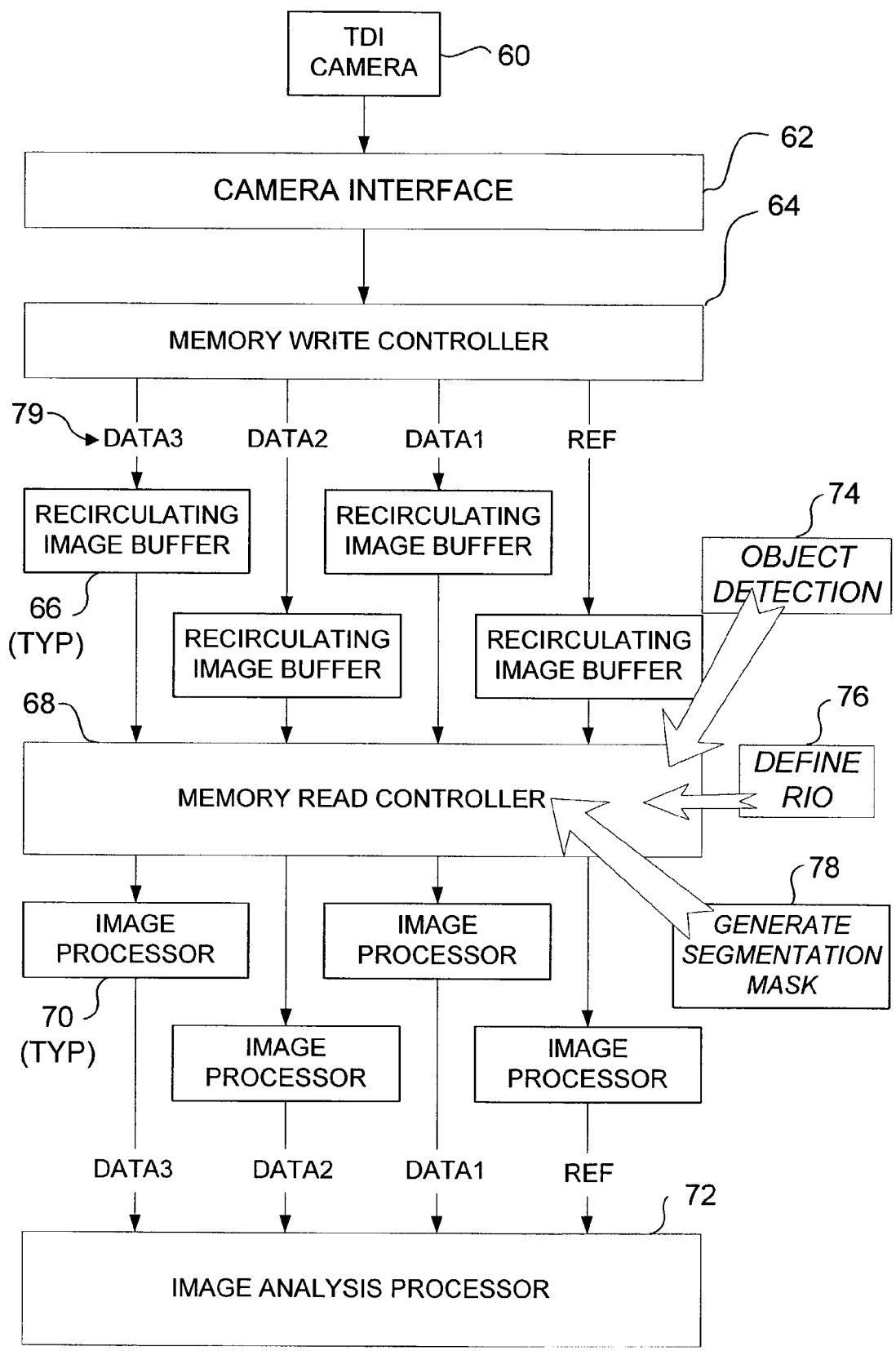
FIG. 5 is a functional block diagram illustrating how the steps used in a first embodiment of the segmentation process of the present invention relate to structural elements required to execute the steps of the first embodiment.

FIG. 5 is a functional block diagram illustrating the steps used in a first embodiment of the segmentation process of the present invention, relative to structural elements required to execute the steps, including the separation of the incoming image record into a plurality of data channels, temporarily storing the image record in recirculating image buffers, reducing the image content into smaller images of ROIs (preferably each of which contains a single object of interest), and generating segmentation masks that accurately identify the pixels belonging to the objects of interest. Note that blocks representing processes that are executed by a functional element are identified in italics.

A TDI camera 60 is used to capture images of an object (preferably, a plurality of objects entrained in a flow of fluid). While system 10 of FIG. 1 represents a preferred imaging system, it should be understood that other imaging systems that include a TDI camera can instead be employed.

A camera interface 62 preferably ensures that the signal from TDI camera 60 is in a format that can be processed by the logical processor employed to execute the method of the present invention. Such a processor is generally indicated as image processing in FIG. 5, which will be described in more detail below, and can be a personal computer, an oscilloscope, or an application specific integrated circuit. Camera interface 62 passes the signal from the TDI camera to a specialized memory write controller 64, which separates the signal from TDI camera 60 into a plurality of data channels. Note that FIGS. 2, 4A, and 4B illustrate image records for four different channels, including one brightfield channel and three fluorescent channels. FIG. 5 similarly includes four channels 79, three of which are data channels (DATA1, DATA2, and DATA3) and one of which is a reference channel (REF). Data in each of the four channels are temporarily stored in four recirculating image buffers 66, each of which preferably comprises individually addressable random access memory (RAM).

It should be noted that while TDI camera 60 and camera interface 62 are included in FIG. 5, previously obtained pixelated image data that has already been formatted to be compatible with the processor employed to execute the method of the present invention can be provided to memory write controller 64, without requiring the use of TDI camera 60 and camera interface 62.

Reduction of the image record into ROI images is accomplished using a specialized memory read controller 68. Controller 68, in conjunction with one or more processors generally indicated by processor 70 in FIG. 5, detects individual objects as indicated by block 74, defines the ROI for each object, as indicated by a block 76, and generates a segmentation mask, as indicated by a block 78. Each segmentation mask is a binary depiction of an object in a ROI. The mask is preferably created using specialized pattern analysis methods. Note that controller 68 ensures that data from the recirculating image buffers are provided to processors 70 in the proper order. While a plurality of image processors 70 are shown, it should be understood that a single processor capable of simultaneously processing a plurality of data channels can also be employed. Additional operations performed by each image processor 70 may include, for example, channel-to-channel alignment, crosstalk removal, and channel-to-channel contrast equalization. The processed image data from each data channel are then directed to an image analysis processor 72. The operations performed by each image analysis processor 72 may include feature calculations and object classifications. The segmentation mask generated by image processors 70 is used by image analysis processor 72. Note that the present invention is not specifically directed at the operations executed in image analysis processor 72, but it is anticipated that the segmentation mask generated by the present invention will be utilized in further processing steps employed to determine characteristics of the object in the ROI.

Preferably image information is delivered to the image processing elements as an uninterrupted sequence of images, or as an uninterrupted sequence of rows of pixels. The architecture of the image processing and analysis algorithms are optimized for execution in a pipeline-style processor of the type used for digital signal processing. To accommodate this approach to general purpose computation, recursive loops and storage of large blocks of samples are avoided. Instead, feed-forward computation, in which the outcome of a first operation executed by a first processing unit is fed to the input of a second processing unit for execution of a second operation. Typically, multiple processors are operated in parallel in order to accomplish the required operations with the speed required to keep pace with the arrival of incoming data.

Figure 6:
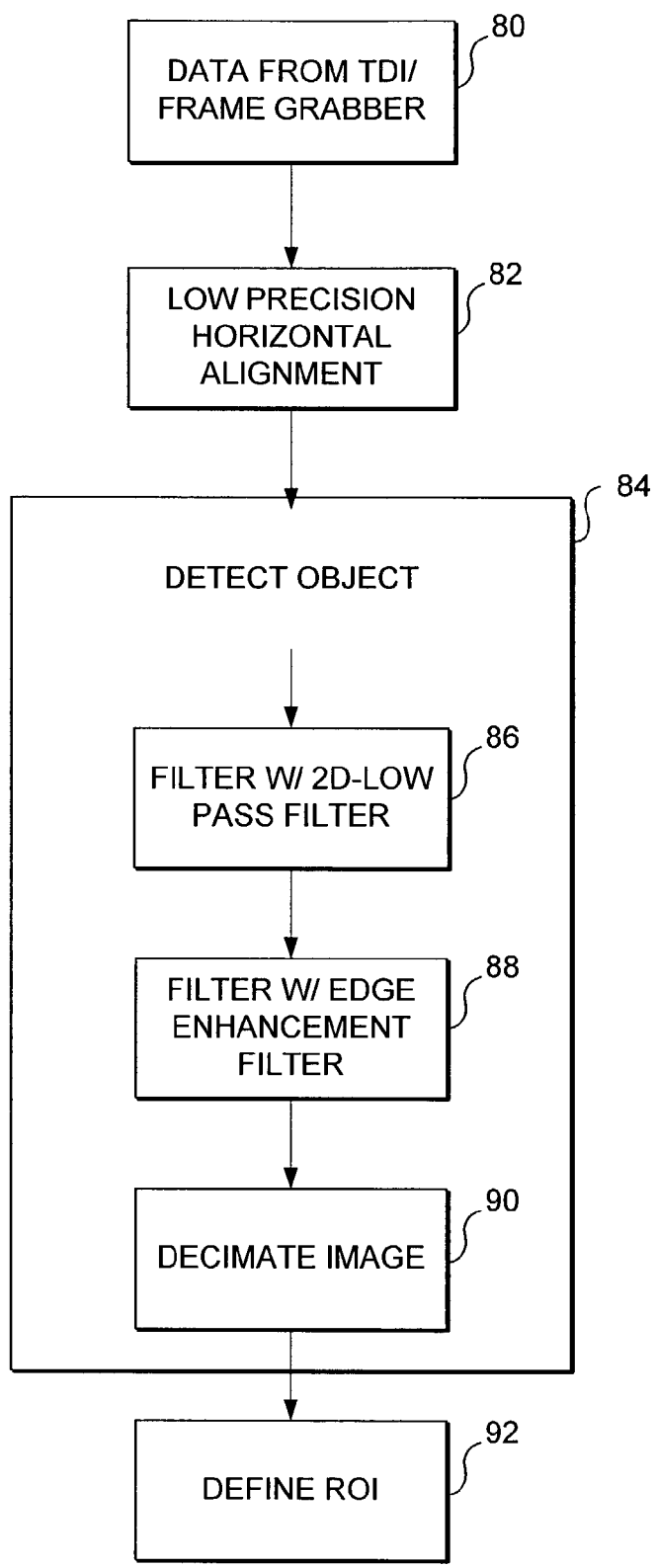
FIG. 6 is a flow chart providing additional detail with respect to the steps used in the primary segmentation process of the first embodiment of FIG. 5.

FIG. 6 is a flowchart providing additional information about the steps employed to reduce the incoming image record into ROIs corresponding to selected objects, in accord with the first embodiment of the present invention.

As described above in conjunction with FIG. 1, the present invention is preferably used in conjunction with a multichannel flow imaging system, wherein a first channel generates brightfield images of the structure of objects and the remaining channels generate images from the fluorescent emission of tagged molecules on the objects. A block 80 represents the generation of image record data by the TDI camera and frame grabber (blocks 30 and 32 of FIG. 3). It should be understood that data from the TDI camera and frame grabber are stored in the recirculating image buffer (FIG. 5), which replaces old image data with new image data as new image data is generated or provided to the memory write controller (FIG. 5).

To process the incoming image record into ROIs, the channels must be aligned. While much of the channel alignment occurs after defining ROIs (as is indicated by blocks 34 and 38 of FIG. 3), it should be noted that the channel alignment operation is preferably accomplished in two stages, including a low-precision stage and a high-precision stage. In the low-precision stage, alignment is accomplished to a precision of a single-pixel in the vertical and horizontal directions. The horizontal portion of the alignment preferably occurs prior to defining the ROI for each object in the image record. Thus, in a block 82, the horizontal portion of the alignment described above is performed by selecting the columns of the image record that are to be processed. As is illustrated in FIG. 2, some columns are typically devoid of information, and those columns are rejected in block 82. Those of ordinary skill in the art will recognize that the design of an imaging system dictates the approximate horizontal locations of the data channels. It is expected, however, that component tolerances and temperature-dependent drift will introduce uncertainty in the channel locations. Horizontal offsets, $O_x[\lambda]$, are used in block 82 to adjust the list of columns to be included in the fluorescence channels containing data ($\lambda 1$, $\lambda 2$, and $\lambda 3$ in FIGS. 2, 4A, and 4B, and DATA1, DATA2, and DATA3 in FIG. 5). Typically, each channel will have the same number of columns. Preferably, a point on an object captured by the imaging system will fall on the same column location in all channels to within a tolerance of +/−0.5 columns after application of the offset. The horizontal offsets $O_x[\lambda]$, can be obtained by carrying out a calibration. An exemplary calibration method is described in commonly assigned U.S. patent application Ser. No. 10/132,059, filed on Apr. 24, 2002.

The present invention, when integrated into an imaging system, enables the capturing of objects arriving randomly at a measurement field of the imaging system. The timing of the capture event is generated by an object detector that monitors a channel chosen for that purpose. A block 84 corresponds to such an object detection process, which preferably includes the steps of applying a two-dimensional (2D) low pass filter, as indicated by a block 86, and applying an edge enhancement filter as indicated by a block 88. The 2D low pass filter improves signal-to-noise ratio, while the edge enhancement filter rejects some background clutter and increases contrast at the boundaries of an object. A block 90 represents a decimating step, which is also part of the object detection process. Decimating the image is carried out with a decimating filter algorithm that facilitates detection of an object. In a block 92, the coordinates of the corners of the ROI for each detected object are determined, thereby defining the ROI. Note that the incoming rows of the image must be stored while the detection process is executed, and that data are stored in the recirculating row buffers illustrated in FIG. 5. In a recirculating row buffer, each arriving row of pixels of the image is stored in memory by overwriting the locations previously occupied by the oldest row of pixels. This approach eliminates the need to shift all of the contents of the memory as new data arrive.

Preferably the brightfield (or reference) channel is utilized for deriving ROI delineation and the generation of object boundaries, although it should be understood that any other channel, or any numerical or any logical combination of channels, may be selected for use in ROI delineation and boundary generation. It should be noted that in a preferred embodiment, the steps described in FIG. 6 are executed only on data from the brightfield channel, for reasons of computational economy. However, all channels, other single channel, or combinations of some of the channels can be beneficially employed as well.

FIG. 7 schematically illustrates of the concept of a recirculating row buffer designed to store eight rows of pixels. When the image record is reduced by cropping out all background information not located in the ROI surrounding each object (see FIGS. 4A and 4B), the order of the rows is reset/restored as the data are read out of the memory.

To detect an object imaged against a noisy background, the detector must rely on characteristics of the object not seen in the background. In a well designed imaging system, the background will be comprised of random noise, with an autocorrelation distance considerably shorter than the dimensions of the smallest object of interest. This condition can be met by using high bandwidth analog channels and a high digitization rate. The spatial frequencies representing the objects of interest will spread over a wide range. A feature of the present invention is that the object detector will act as a filter matched to the spatial frequencies most useful for detecting the objects of interest and capable of rejecting noise and unwanted objects. Another feature of the present invention is the reduction of the computational steps required for signal processing. The algorithms chosen for the steps in the object detection process are optimized for execution on a pipeline processor.

Referring once again to block 86 of FIG. 6, a 2D low pass filter is applied to improve the signal-to-noise ratio (i.e. to the selected channels as described above). The upper end of the spectrum of the random noise will typically approach the Nyquist limit established by the image digitization rate. The low pass filter is applied on the premise that the object detection can rely on the spatial frequencies that define the general size and shape of the object and that the highest frequencies in the object, such as those representing fine texture and sharp breaks in the object boundaries, can be removed. The expression for the filter operation is as follows:

$$G'[m_1, m_2] = \sum_{q=-N}^{N} \sum_{p=-N}^{N} G[m_1 + p, m_2 + q]h[p + N, q + N]$$

where:

W=width of the filter kernel (odd)

N=(W−1)/2.

The characteristics of the low pass filter are determined by the values of the filter kernel, h[$k_1$, $k_2$]. The number of points in the kernel and the shape of the kernel are chosen to accomplish the desired amount of noise reduction. In the preferred embodiment, the filter kernel width, W, is 3, and the values, h[$k_1$, $k_2$], are set to a constant. Those skilled in the art will recognize this configuration as a 3×3 boxcar filter. Boxcar filters of greater spatial extent, such as 5×5 or 7×7, for example, and filters with shapes other than square, such as triangular or Gaussian, are useful alternatives to the 3×3 boxcar filter.

The image background may also carry a bias, such as a direct current (DC) voltage level introduced by the signal processing electronics or, in the case of brightfield imaging, a generally uniform illumination field. A modulation slowly varying across the field of view may be superimposed on this bias, as in the case of an illumination source of non-uniform intensity. The bias and the low frequency modulation will be removed as unwanted components of the image by application of an edge enhancement filter, as indicated in block 88 of FIG. 6.

FIG. 8 is a schematic diagram of the coordinate system of points and axes used in the gradient operator (i.e., the edge enhancement filter) in accord with the present invention. As shown in FIG. 8, pixels 130 correspond to points in the coordinate system, and axes 132 define all possible connections between the pixels. Note that each of the four pixels 130 employed in the edge enhancement filter occupies a different one of the corners positions relative to a pixel 134 that is currently being processed.

The edge enhancement filter increases the value of pixel 134 if pixels 130 indicate that pixel 134 is adjacent to an amplitude gradient. If all four pixels 130 comprising the filter set are equal, then pixel 134 is assigned a zero value. The condition depicted in FIG. 10, however, is one in which pixel 154 is near a gradient 150 (i.e., an amplitude increasing in the direction of pixel 152 (or pixel C), one of the four pixels 130). The presence of gradient 150 causes the value of the pixel 154 to increase. Many other shapes of an amplitude contour defined by gradients can be imagined by considering the surface depicted in FIG. 10 to be a flexible sheet. Corners or edges may be elevated above or depressed below the nominal level plane of the sheet. However, the sheet will have some degree of smoothness and rigidity provided by the low pass filter applied in block 86 of FIG. 6, which removed some of the noise and fine structure from the image.

The computational steps in the application of the edge enhancement filter are shown in FIG. 12. In discussing FIG. 12, reference will be made to pixels 130, pixel 134, and axes 132 of FIG. 8. Gradients along any of the axes are identified by calculating differences in amplitude among the four pixels 130 in the filter. In a block 170, data from the reference channel portion of the image data record is obtained, and then in a block 172, for each pixel in the data, the absolute value of the differences between each pair of pixels defining an axis is computed. As indicated in FIG. 8, there are six axes and thus, there are six absolute values to compute. As noted above, data from channels other than the reference channel, or in addition to the reference channel, can be similarly processed.

Next, the axis of least inclination (i.e., the axis with the smallest absolute value for the difference in amplitude of the two pixels that define the axis) is selected in a block 174, for use as a pivot axis. The gradient along the pivot axis will be considered to be zero, and the pivot axis pixels will not be used in the computation of the value of central pixel 134.

Note that the pivot axis is defined by two of four pixels 130. The absolute difference computed in block 172 for the axis defined by the other two pixels 130 is selected in a block 176, to be used with additional information to compute a new value for central pixel 134. In a block 178, the projection of the two differences (i.e., the difference corresponding to the axis of least inclination determined in block 174, and the difference from block 176) is computed for the x and y axes. In a block 180, the x and y projections from block 178 are used to compute a magnitude of a gradient vector.

A line joining central pixel 134 to any one of pixel 130 has a predefined angle. FIG. 9 defines an arbitrary polar coordinate system for designating these angles. The case shown in FIG. 10 serves as an example of how the new central pixel value is computed. In FIG. 10, axis 2 is defined by two pixels 130 (marked as A and D). Axis 2 is taken as the pivot axis, and as described above, the other two pixels 130 (marked as pixels B and C) are used in the gradient calculation, as follows:

$$\vec{D}_1 = |C - X| \angle \pi/4 = M_1 \angle \pi/4$$

$$\vec{D}_2 = |B - X| \angle -3\pi/4 = M_2 \angle -3\pi/4$$

$$M_1 \angle \pi/4 = M_1[\cos(\pi/4) + j\sin(\pi/4)]$$

$$M_2 \angle -3\pi/4 = M_2[\cos(-3\pi/4) + j\sin(-3\pi/4)]$$
$$= M_2[-\cos(\pi/4) - j\sin(\pi/4)]$$

$$Mag(\vec{D}_1 + \vec{D}_2) = \sqrt{(M_1 - M_2)^2[\cos^2(\pi/4) + \sin^2(\pi/4)]}$$
$$= M_1 - M_2.$$

The above calculation reduces to a simple difference of the magnitudes of the opposing vector directions, $M_1$ and $M_2$. In a second example, shown in FIG. 11, axis 160 is similarly defined by two pixels 130 (marked as pixels A and B). Axis 160 is taken as the pivot axis and the other two pixels 130 (marked as pixels C and D) are used in the gradient calculation, as follows:

$$\vec{D}_1 = |C - X| \angle \pi/4 = M_1 \angle \pi/4$$

$$\vec{D}_2 = |D - X| \angle -3\pi/4 = M_2 \angle 3\pi/4$$

$$M_1 \angle \pi/4 = M_1[\cos(\pi/4) + j\sin(\pi/4)]$$

$$M_2 \angle 3\pi/4 = M_2[\cos(-3\pi/4) + j\sin(-3\pi/4)]$$
$$= M_2[-\cos(\pi/4) + j\sin(\pi/4)]$$

$$Mag(\vec{D}_1 + \vec{D}_2) = \sqrt{(M_1 - M_2)^2\cos^2(\pi/4) + (M_1 + M_2)^2\sin^2(\pi/4)}$$
$$= \frac{\sqrt{2}}{2}\sqrt{(M_1 - M_2)^2 + (M_1 + M_2)^2}.$$

The two examples provided above cover all possible cases. Opposing vectors use the simple magnitude difference, while vectors spaced 90 degrees apart use the more complex quadrature sum formula. In a preferred embodiment, the quadrature summation operation is accomplished by using a look up table, to reduce computation save time.

The distribution of amplitudes in images manipulated by the combination of the low pass filter and the edge enhancement filter is highly dependent on the image content. The performance of the next stage of the object detection process (i.e., the decimation step in block 90 of FIG. 6) is optimized by remapping the output of the edge enhancement filter to reject noise and accomplish the desired contrast. A grayscale transformation process for noise rejection and channel-to-channel equalization is schematically diagrammed in FIG. 13. A window 184 in an original amplitude grayscale 182 is selected so as to include the most useful information. Window 184 is then mapped into a new output grayscale 190. Low levels containing noise are rejected by applying an offset 186. The contrast is optimized by applying gain 188 to the data after applying the offset.

FIG. 14 is a pictorial representation of the modification of an image record in accord with the present invention. In a block 192, a brightfield image 198 is transformed into a high-contrast darkfield image 200 by applying the 2D low pass filtering described above. Next, the edge enhancement filtering described above is performed in a block 194, and then, the grayscale transformation discussed above with respect to FIG. 13 is executed in a block 196, to achieve darkfield image 200.

The next step in the process of reducing the image record into ROIs is the detection of objects in the high-contrast transformed image and the identification of the approximate centers of those objects. Objects such as biological cells carried in a flowing stream of liquid will pass through the sensitive volume of the image capture system at random times. Therefore, the object detector must continuously monitor the incoming image record. The operation of finding the center of an object is initiated when the object has been detected. Furthermore, the object detector acts as a filter matched to the approximate size and contrast characterizing the objects to be retained in ROIs for further analysis.

The low pass filtering and edge enhancement filtering operations described above are performed before the step of object detecting with the object detector, and thus, collectively act as a band-pass filter. Preferably, the object detector comprises a multiple channel, 2D low pass filter with image down-sampling. FIG. 15 schematically illustrates the process of generating a plurality of low pass filtered and down sampled representations of a region of an image record, thus providing an example of the operation of the object detector. An incoming image 202 has a pixelated format corresponding to the pixel density of the camera employed to capture the image. A block 220 schematically illustrates a down-sampling operation, which results in an image containing fewer pixels. Preferably, the down-sampling operation averages the pixel values in 2×2 regions of the original image to generate values for pixels in a new image. The new image includes one quarter of the number of pixels in the original image, and each pixel in the new image represents an area of 2×2 photodetector samples.

Thus, incoming image 202 (16×16 pixels) undergoes a down-sampling operation as indicated by an arrow 204 to generate a new image 206 (8×8 pixels). Image 206 then undergoes a down-sampling operation as indicated by an arrow 208 to generate a new image 210 (4×4 pixels). Similarly, image 210 undergoes a down-sampling operation as indicated by an arrow 212 to generate a new image 214 (2×2 pixels). Finally, image 214 undergoes yet another down-sampling operation as indicated by an arrow 216 to achieve a new image 218 (1 pixel). In each successive down sampled image, the pixels represent a correspondingly larger area of the photodetector samples, such that the single pixel in image 218 includes data from the original 16×16 pixels image provided by the photodetector (i.e., image 202). Each step in the cascade of filtered down-sampling operations reduces the frequency content in the image by a factor of two. Thus, image 218 is a single value or pixel equal to the average amplitude of the area of image 202.

FIG. 16 is a graphical representation of a surface plot of four filtered and down sampled representations of a region of an image record. A leftmost image 222 carries the highest frequency content and includes peaks 232 and 230 (each peak corresponding to an object). Preferably the peaks correspond to discrete objects, rather than separate features on a single object. The number of decimations (i.e. down samplings) is preferably selected so that only a single peak will remain after the last decimation. Each of the pixels in this image represents a 4×4 region of photodetector samples. Image 222 has a high noise level and retains much of the fine structure of the two objects captured in the image. An image 224 represents the results of a first down-sampling process, an image 226 represents the results of a second down-sampling process, while an image 228 represents the results of a third down-sampling process. Each of these down sampled images (i.e. images 224, 226, and 228) includes progressively less high-frequency content and delivers progressively smoother images of the two peaks. The "density" (with respect to the original photodetector data) of a single pixel in each of images 222, 224, 226, and 228 are indicated in FIG. 16, and respectively are 4×4, 8×8, 16×16, and 32×32. As described with respect to FIG. 16, each down-sampling process increases the amount the photodetector samples contained in a each pixel of the resulting image, such that a single pixel in image 222 corresponds to a 4×4 sample from the photodetector, while a single pixel in image 228 corresponds to a 32×32 sample from the photodetector.

The images delivered by the down-sampling multiple-channel filter (i.e., by the object detector) described above in regard to FIGS. 15 and 16 are processed according to an object detector algorithm. FIG. 17 is a flow chart showing the steps employed by the object detector algorithm to locate the center of an object and to generate the boundaries of a ROI containing that object. The object detecting process is based on using a heavily-filtered image from deep within the cascade of the multiple-channel filter for the initial detection of an object. The particular image chosen for the detection will not include objects too small to be of interest, because those objects will be filtered out of the image. The low-frequency channel will be monitored continuously using an amplitude threshold. The detection event can be conditioned on a single pixel in the image exceeding a predetermined amplitude threshold, on a group of contiguous or closely-spaced pixels exceeding the threshold, or on other rules that are based on the image content. A more detailed description of the steps indicated in FIG. 17, which includes the down-sampling steps described in conjunction with FIGS. 15 and 16, is provided below.

The object detection process beings with the storage of a full spectrum image in a buffer in a block 240. The down-sampling process described above (i.e. filtered decimation) is executed first in a block 242, yielding a filtered image with fewer pixels as is indicated by a block 244. The down-sampling process is executed a second time in a block 246, to yield yet another image with fewer pixels, as is indicated by a block 248. In a block 250 the down-sampling process is executed for a third time to yield a filtered image with still fewer pixels (as is indicated by a block 252). The down-sampling process is executed a fourth time in a block 254, to produce a final image with still fewer pixels, as indicated by a block 256. Preferably sufficient down sampling operations are performed so that all the image data is reduced to single high density pixel.

While a heavily-filtered image is desirable for the initial detection of the object, the loss of structural detail caused by the filtered down-sampling operations reduces the precision and accuracy of any attempt to locate the object center using that image. The less filtered renderings of the image space containing the detected object, however, are retained in the filtering process. The location at which the amplitude of the heavily-filtered image indicated by block 256 exceeded the detection threshold can be extrapolated to the locations of the object in the other images, as illustrated in FIG. 18, which is a contour map of the images displayed in FIG. 16. Two objects were captured in the image. A first object 288 (corresponding to object 230 in FIG. 16) is large and shows high contrast with respect to the background. A second object 290 (corresponding to object 232 in FIG. 16) is smaller and has less contrast. By way of example, object 288 will be defined as an object of interest to be retained in a ROI. Object 290 will be defined as an object too small and dim to be of interest, and will be rejected. In a block 258 (FIG. 17), a size of any objects in the heavily filtered image is checked to see if any objects in the image are greater in size than a predetermined threshold. If no objects are greater than the threshold size, then the logic proceeds to a decision block 259 and it is determined if more full size images are to be processed. If so, the next full size image is loaded into the buffer in a block 261, and the logic proceeds to block 242 and the first decimation is executed as described above. If in decision block 259, it is determined that no more full size images are to be processed, then the object detection algorithm terminates in a block 263. Note that in decision block 258, an image may contain more than one or more objects, some of which may exceed the threshold and some of which may not, as described above in conjunction with FIG. 18. Smaller sized objects will preferably be deleted from the image. FIG. 18 illustrates this elimination, in that a first filtered image 280 includes peaks 288 and 290, a second filtered image 282 includes peaks 288 and 290, and a third filtered image 284 includes peaks 288 and 290, while a fourth filtered image (i.e., the most heavily filtered image) includes only peak 288, peak 290 having been eliminated as being smaller in size than the threshold.

The location of peak 288 in image 286 of FIG. 18 (and of peaks in any heavily filtered image) can be extrapolated to determine a more accurate location of the same peak in the less filtered images, by multiplying the vertical and horizontal coordinates of the peak in the most filtered image (i.e., peak 288 in image 286) by a factor of two to find the same peak (i.e., the same object) location in image 284. A more accurate location of the peaks in image 282 can then be similarly determined, by multiplying the vertical and horizontal coordinates of the extrapolated position of the peak in image 284 by a factor of two, and so forth. This extrapolation process is initiated in a block 260 in the flowchart of FIG. 17, in which the peak of the fourth filtered imaged is determined based on its vertical and horizontal coordinates. Of course, if the image includes more than one peak, the locations of all the peaks are found (although as noted above preferably enough down sampling operations are performed to reduce the image data to a single high density pixel with a single peak representing a single object).

Note that it is preferred to extrapolate back from the highest level of down sampling (i.e. decimation) to the next lowest level, and so on, back to the undecimated image data, rather than simply determining the peak location of the first filtered image based on the location of the peak in the most heavily decimated image using the multiplier separating orders of decimation (i.e. a factor of 8 in the present example). This is due to the fact that processing a single extrapolation based on a factor of two is very fast, while processing for a factor of 8 is much more computationally intensive. So a plurality of very fast computations can be achieved more rapidly than a single complex computation. Then in a block 262 the extrapolated address of the peak in the third image is determined by multiplying the vertical and horizontal coordinates of the peak in the most filtered image (i.e., peak 288 in image 286) by a factor representing the density difference between the pixels in the third image and the pixels in the most filtered image (i.e., a factor of two). Next, in a block 264, the extrapolated address of the peak in the third image is used to determine the extrapolated address of the peak in the second image, by multiplying the extrapolated address of the peak in the third image by a factor representing the density difference between the pixels in the third image and the pixels in the second image (i.e., a factor of four). In a block 266 the extrapolated address of the peak in the first image is determined by multiplying the extrapolated address of the peak in the second image by a factor representing the density difference between the pixels in the first image and the pixels in the second image (i.e., a factor of two). In the present example (i.e. peaks 288 and 290 of FIG. 18), the location of the smaller object, peak 290, is not examined because the smaller object was below the threshold (see block 258 of FIG. 17).

With knowledge of the frequency content of the objects of interest, an image is selected for finding the center of the object. The center can be found by simply locating the pixel of maximum amplitude, or by computing the centroid of the pixels in a region around the location estimated by extrapolation. This step is executed in a block 268, as illustrated in FIG. 17. Once the center of the ROI for an image has been detected, the logic returns to decision block 259 to determine if more full resolution images are to be processed.

Although the matched filter and down sampling approach described above is able to eliminate objects smaller than the minimum size of interest, objects larger than the maximum size of interest must be rejected by another method. With the center of the object located in a high-resolution image, a pattern analysis algorithm can be applied to the region around the location of the center to find the approximate area of the object in the image. However, in a preferred embodiment, a second stage of object segmentation using a boundary-tracking algorithm is executed on the ROIs. Objects larger than the maximum size of interest are rejected in this stage.

Once the center of an accepted object has been located, the boundaries of the ROI containing that object are computed. If the location of the center is found in an image down sampled from the full resolution image, the center location is extrapolated to its position in the full resolution image. The size and shape of the ROI is known a priori from the definitions for the objects of interest. The dimensions of the ROI will be chosen to easily accommodate the largest object of interest and a margin of background pixels in the space surrounding that object. The ROI boundaries are applied when pixels are accessed by memory read controller 68 for image processing operations 70 as described in connection with FIG. 5.

As described in connection with FIG. 6, in block 82, the horizontal portion of the alignment described above is implemented with respect to blocks 36 and 38 of FIG. 3, before the objection detection algorithm determines the center of the ROI. After the center of the ROI has been determined as described above, the vertical portion of the alignment is performed by selecting the columns of the image record that are to be processed. As noted above, the extent of the vertical offsets are preferably determined by a calibration method. FIG. 19 illustrates the application of the ROI boundaries with vertical offset correction. Note that the center of the ROI is offset in the vertical position according to predetermined offsets. An image 310 of an object displayed in a $\lambda_1$ channel 302, for example, is offset upwardly with respect to an image 308 of that object displayed in a brightfield channel 300. A ROI 309 applied to that object in $\lambda_1$ channel 302 is offset upwardly to properly bind the image. Similarly, ROIs 311 and 313 applied to images 312 and 314 in a $\lambda_2$ channel 304 and a $\lambda_3$ channel 306, respectively, are offset to match the vertical misregistrations of those channels with respect to brightfield channel 300.

Second Preferred Embodiment

FIG. 20 is a functional block diagram illustrating how the steps employed in a second embodiment of the segmentation process of the present invention relate to structural elements required to execute the steps of the second embodiment. The second embodiment also provides for separating the incoming image record into a plurality of data channels, temporarily storing the image record in recirculating image buffers, reducing the image content into smaller images of ROIs (preferably each of which contains a single object of interest), and generating segmentation masks that accurately identify the pixels belonging to the objects of interest. The functional block diagram of FIG. 20 (i.e., the second embodiment) differs from the functional block diagram of FIG. 5 (i.e., the first embodiment) only in blocks 74 (FIG. 5) and 74a (FIG. 20), which refer to the specific type of object detector employed in each embodiment.

FIG. 21 is a flow chart of the operations comprising the object detection process of the second embodiment of the present invention. The flowchart of FIG. 6 for the first embodiment differs from the flowchart of FIG. 21 for the second embodiment in blocks 84 (FIG. 6) and 84a (FIG. 21), which refer to the step of object detection, and blocks 88 (FIG. 6) and 88a (FIG. 21), which refer to the step of applying an edge enhancement filter. Thus, the step of generating an image record data with a TDI camera and frame grabber (blocks 30 and 32 of FIG. 3) in block 80 and the step of performing a horizontal alignment in block 82 are commonly shared in the first and second embodiments. Different object detection techniques are employed in each embodiment. While block 84a in FIG. 21 represents object detection, and block 84 in FIG. 6 also represents object detection, it should be understood that the steps executed in each object detection process are different.

Preferably the object detection process of each of the two embodiments utilize the same 2D low pass filter, as indicated by block 86 of both FIGS. 6 and 21. In block 88a, a different edge enhancement filter is applied in the second embodiment. Note that the purpose of applying the edge enhancement filter in the second embodiment remains the same, i.e., to remove any bias and the low frequency modulation and to accentuate object boundaries. The specific steps employed in block 88a to remove any bias and the low frequency modulation and to accentuate object boundaries in the second embodiment are described in more detail below, with respect to FIGS. 22–25. Next, in a block 90a of FIG. 21, histograms are generated for each image that has been filtered using the 2D low pass filter and different edge enhancement filter. In the first embodiment, a decimation process was employed in block 90 to determine a center of the ROI, thereby enabling the ROI to be defined in block 92a. In the second embodiment, a row by row analysis of the histograms prepared in block 90a enables the ROI to be defined in a block 90a. FIGS. 25–28B, which are described in detail below, illustrate the use and manipulation of histograms in the second embodiment.

FIG. 22 is a schematic diagram of the five pixels used in the edge enhancement filter, and includes an equation 360 that defines a center pixel G in terms of the other identified pixels (i.e., pixels A–D). The edge enhancement filter increases central pixel values in regions where the slope of the intensity is large in both the vertical and the horizontal directions. The linear expression for this operator is as follows:

$$G = \frac{\partial}{\partial y}\frac{\partial I}{\partial x}.$$

The preferred implementation of the gradient operator in sampled image space is defined as follows:

$$G_{i,j} = |(I_{i+1,j+1} - I_{i-1,j+1}) - (I_{i+1,j-1} - I_{i-1,j-1})|.$$

The relationship between the preferred implementation and equation 360 in FIG. 22, and the nomenclature for addressing the pixels 354 defined in FIG. 22, which are diagrammed in FIG. 23, should be noted. FIG. 24 is a pictorial representation of the transformation of an image of an isolated object to a gradient image of that object by application of the gradient filter of the second embodiment. An image 394 of a single object in a noisy background is transformed by the gradient filter into an image 398 having a collection of four sharper peaks at the periphery of the object. The background noise is rejected after the generation of the histograms in block 90a of FIG. 21, as described in more detail below.

Details relating to the histograms generated and manipulated in second preferred embodiment are provided in FIGS. 25A–28B. Before histograms corresponding to sample data (i.e., images of objects) collected by an imaging system are processed and the ROI is defined, a threshold value is determined. The threshold value is employed to reject images that do not correspond to images with objects in a ROI.

A flowchart of a simple process for determining such a threshold value is shown in FIG. 25A. In a block 370, an image preferably depicting only a noisy background is obtained, and its signal is filtered with the 2D low pass and edge enhancement filters of the second embodiment as described above. This noisy image is preferred for setting a threshold that is used to analyze images containing objects of interest. In a block 372, an amplitude histogram of the noisy image is generated. FIG. 27 graphically illustrates a histogram of pixel amplitudes for a locus of pixels selected from such a noisy image (i.e., pixels representing a region devoid of objects) and includes a table of corresponding histogram values. In FIG. 25A, a mean amplitude of the noisy image is calculated in a block 374 from the histogram using the following relationship:

$$E[A] = \frac{\sum_{i=0}^{N} n(i) * i}{\sum_{i=0}^{N} n(i)},$$

where:

E[A]=mean value of the amplitude
N=number of amplitude levels in histogram
n(i)=number of pixels having value i.

The mean value of the background is multiplied by a scale factor in a block 376 to determine a threshold value. The scale factor preferably has been empirically shown to remove the background noise while retaining the desired image information. In the example illustrated in FIG. 26, the scale factor is 8.0, yielding a threshold of 4.8, for a mean amplitude value of 0.6.

Noting that a preferred imaging system (such as system 10 of FIG. 1) is intended to image a flow of objects entrained in a fluid, it is likely that when a noisy image is obtained to generate a threshold for use in analyzing sample images including objects, a plurality of noisy images will be provided by the detector of the imaging system. Furthermore, it should be understood that even when an imaging system is processing samples that include a plurality of objects, most of the data obtained by imaging systems will be noisy images, rather than object images. This is particularly true of an imaging system that collects images of objects entrained in a flow of fluid. In general, the imaging system continually images the fluid flow, and many of the images generated will be of the fluid with no object. Such images correspond to the object free noise filled image used to generate the threshold value in FIG. 25A. It is anticipated that it would be highly desirable to provide a technique for generating a threshold value concurrently with obtaining sample data that includes images of objects. To achieve this, the object images and the noisy images must be separated, so that only noisy images are used to determine the threshold value. This is because using an image containing an object (or objects) to generate the threshold value will undesirably increase the threshold value.

If one or more objects are captured in an image provided by the detector of the imaging system that is employed, the simple histogram of FIG. 26 is replaced by a more complex histogram, such as the one illustrated in FIG. 27. Although relatively few in number, pixels 333 with values in the region centered about an amplitude along the x-axis having a value of 24 greatly modify the value of the mean, and, therefore, also modify the value of the threshold. If such an image (rather than the noise only image that is preferred) is employed to generate the threshold value, the resulting higher threshold (as compared to the threshold obtained from a noise only image) may prevent some of the important image information from being analyzed.

An improvement in the threshold computation process described in conjunction with FIG. 25A, which enables a plurality of images, some noisy images and some object images, to be employed to determine the threshold value, is to apply a low pass filter to the threshold value, making it robust in avoid inclusion of the occasional object in an image used to generate the threshold. FIG. 25B is a flowchart for such a robust process for determining a threshold value. As is the simplified method described in conjunction with FIG. 25A, in block 370, an image (preferably depicting only a noisy background) is obtained and its corresponding signal is used after filtering with the 2D low pass and edge enhancement filters of the second embodiment, as described above. Note that with respect to a flow imaging system, such as system 10 of FIG. 1, it is unlikely that the first image obtained by the system will be an image of an object. This can be controlled by passing a small volume of object free fluid through the imaging system before passing fluid containing objects through the imaging system. In a block 372, an amplitude histogram of the noisy image is generated. A mean amplitude of the noisy image is calculated in a block 374, as described above. In a decision block 371, it is determined whether any other noisy images are being received from the imaging system. If not, then the mean value determined in block 374 is multiplied with the factor described above in block 376 to obtain the threshold value. If in decision block 371, it is determined that other noisy images are being received from the imaging system, then in a block 373, the next noisy image is obtained (and its signal is filtered with the 2D low pass and edge enhancement filters of the second embodiment, as described above), and in a block 375, an amplitude histogram of the next noisy image is generated. Then, in a block 377, the previous noisy image histogram counts are reduced by a factor of two. In a block 380, a new mean value for the amplitude is determined using data from blocks 375 and 377. The new mean value includes amplitude data from both the present and prior noisy images. This process acts as a low pass filter to the threshold value, minimizing the effect of occasionally including an object in one of the noisy images used to generate the threshold. From block 380, the logic returns to decision block 371.

A second improvement that is preferably incorporated into the method for determining the threshold described in conjunction with FIG. 25B is the application of a set of weighting coefficients to the histogram corresponding to the next image (i.e. in block 375 of FIG. 25B) as it is generated. The coefficients give the grayscale levels well above the noise floor much less weighting than the levels near the noise floor. The weighting coefficients are computed from the previous histogram, as follows:

$$w_n[i] = 0.5 * \left(1 - \frac{x[i] * |x[i]|}{x[i]^2}\right)$$

where:

$$x[i] = \frac{i}{E_{n-1}[A]}$$

n=index of the current image
$w_n[i]$=weighting coefficient
i=gray level.

The subsequent histogram is computed using the following relation:

$$E_n[A] = \frac{\sum_{i=0}^{N} w_n(i) * n(i) * i}{\sum_{i=0}^{N} w_n(i) * n(i)},$$

where:

$E_n[A]$=mean value of the amplitude
N=number of amplitude levels in histogram
n(i)=number of pixels having value i
$w_n(i)$=weighting coefficient for value i.

FIG. 28 is a plot of the histogram of FIG. 27, modified by the application of the weighting coefficients described above. Note that the portion of the pixel counts for the background pixels, at gray levels of five and below (along the x-axis), are modified very little, while the pixel counts for objects in the region of gray levels 20 through 30 are suppressed to zero. The use of the histogram weighting operation further stabilizes the value of the amplitude threshold against the influence of objects arriving in the field of view.

Once the threshold has been defined, sample image data (i.e., from samples containing objects, as opposed to the relatively object free images used to generate the threshold) from an imaging system, such as imaging system 10 of FIG. 1, are obtained. Histograms are generated and analyzed, as generally indicated by block 90a in FIG. 21, enabling the ROI to be defined in block 92a (also FIG. 21). Further details of the processes involved in blocks 90a and 92a are provided in FIG. 25C. Note the process described in the flowchart of FIG. 25C occurs after the sample image data have been filtered using the 2D low pass and edge enhancement filters of the second embodiment, and after a threshold has been defined as described in connection with either FIG. 25A or 25B.

In a block 400, the signal from an image (preferably an image containing objects) that has been filtered with the 2D low pass and edge enhancement filters of the second embodiment as described above, is used to generate an amplitude histogram of the signal for the image 402 that preferably contains an object. A mean amplitude of the signal for such images is calculated in block 404, as described above. In a decision block 406, it is determined whether or not the mean amplitude of the object image is greater than the threshold determined as described above. If the mean amplitude of the object image is not greater than the threshold, then in a block 407 it is determined if there are more images being provided by the imaging system (i.e. images that have been filtered as described above). If no more images are present, then the ROI definition process of FIG. 26C is over. If more images are present then a next object image is obtained in a block 408 (after filtering with the 2D low pass and edge enhancement filters of the second embodiment as described above). A histogram of that next image is then prepared in block 402. If in decision block 406 it is determined that the mean amplitude of the object image is greater than the threshold, then in a block 410 a first row of the image selected. In a decision block 412 it is determined whether any pixel in that row is greater than the threshold. If not, then in a decision block 414 it is determined whether or not an ROI flag has been set. If so, then the next N rows are included in the ROI in a block 416, while in a block 418 the ROI is copied into an output buffer used by image processors 70 (FIG. 5). In a block 420, the ROI flag is reset, and in a decision block 422 it is determined whether the present image includes more rows. If so, then the next row is selected in a block 424. The next row is then analyzed in the same manner, starting in decision block 412, determining if any pixels in the next row are greater in value than the threshold. If in decision block 422 it is determined that the present image has no more rows, then in a decision block 432 it is determined if there are more images being provided by the imaging system (i.e. images that have been filtered as described above). If no more images are present, then the ROI definition process of FIG. 26C is over. If more images are present then a next object image is obtained in block 408 as described above, and a histogram and mean amplitude for that next image are prepared (blocks 402 and 404) as described above.

Returning now to decision block 414, if the ROI flag is not set, then the logic moves immediately to decision block 422, bypassing blocks 416–420. In decision block 422, as described above, the present image is reviewed to determine if additional rows are to be analyzed.

Returning now to decision block 412, if no pixels in the present row has a value greater than the threshold value, then the logic proceeds to a decision block 426 to determine if the ROI flag is set. If the ROI flag is set, then in a block 434, the present row is included in the ROI. Then, the logic moves to block 422 to determine if more rows are to be analyzed, as described above. If, in decision block 426, it is determined that the ROI flag is not set, then in a block 428, the ROI flag is set, and in a block 430, the N previous rows are included in the ROI. Once again, the logic moves to block 422 to determine if more rows are to be analyzed.

With respect to the above row analysis, each pixel is preferably set to either "zero" or "one," zero indicating that the value of the edge enhanced image at that pixel fell below or equaled the threshold, one indicating that the value exceeded the threshold. The process described in the flowchart of FIG. 25C is summarized as follows.

The image data are accessed one row at a time. Each row is tested for the presence of at least one pixel above threshold. If that condition is met and if a ROI is not under construction, a flag is set indicating that a ROI is under construction, and the present row and a predetermined number of previous rows are marked for inclusion in the ROI. As more rows containing ones are accessed, those rows are also marked for inclusion. When a row containing all zeroes is detected, a sequence is executed to complete and close out the current ROI. The sequence includes the steps of acquiring and marking a predetermined number of rows following the detection of the first empty row at the trailing edge of the ROI. The complete list of ROI rows is then copied to an output buffer, and the ROI flag is reset. The row addresses are used by the memory read controller for accessing image data stored for the recirculating image shown in FIG. 20. The astute reader will note that the result of the above process will be a ROI containing fewer rows than the original image, but the same number of columns. It should be understood that substantially the same steps can be applied to the ROI containing fewer rows than the original image to reduce the number of columns in the ROI as well.

Object Segmentation Common to Both Embodiments

After the initial division of the image stream into ROIs, in accord with either of the embodiments described above, such regions must be further processed to extract more fine-grained information about the size and shape of objects contained within each ROI. FIG. 29A is a flowchart of the processing steps representing a preferred method for extracting object shapes from the image data within a ROI. This preferred method can be employed in either of the embodiments described above. Note that one intended function of this method for extracting object shapes from a ROI is to develop a binary mask image used when identifying objects of interest, as explained below. It should be understood that the image having a defined ROI obtained in block 440 can be provided by an imaging system such as system 10 that is processed in accord with the first and second embodiments described above.

In a block 442 the image having a defined ROI from block 440 is processed to achieve a small binomial blur. A binomial blur operation is employed for obtaining the approximate effect of convolving the signal with a Gaussian filter, without performing any multiplications, and, if the image data are in integer form, with only integer additions. If a row or a column of image data is denoted by x, and there are N data elements in such a row or column, then a single iteration of the binomial blur operation can be represented by the following assignments:

$x_i \leftarrow x_i + x_{i+1}, 1 \leq i < N$ $x_N \leftarrow x_N + x_N$ $x_i \leftarrow x_{i-1} + x_i, 1 < i \leq N$ $x_1 \leftarrow x_1 + x_1$.

The following mathematical exercise demonstrates that m/2 iterations of the binomial blur operation are equivalent to convolving with the binomial kernel:

$$k_i = \frac{m!}{i!(m-i)!}, 0 \leq i \leq m.$$

Applying Stirling's approximation to the factorials in the above equation provides:

$$\ln k_i \approx m \ln m + \frac{1}{2}\ln(2\pi m) - i \ln i - \frac{1}{2}\ln(2\pi i) - (m-i)\ln(m-i) - \frac{1}{2}\ln(2\pi(m-i))$$

For $i \equiv 1/2 m + \epsilon$, the preceding equation expands to the quadratic form, as shown below:

$$\ln k_i \approx \left(m + \frac{1}{2}\right)\ln 2 - \frac{1}{2}\ln(\pi m) - 2\varepsilon^2/m,$$

to leading order in $\epsilon/m$

The above equations demonstrate the Gaussian limit of the binomial kernel. The implied standard deviation is $\sqrt{m/2}$ (i.e. the square root of m divided by 2), so that for only two iterations of the binomial blur operation, the total kernel width of 5 is already sufficiently large, compared to the standard deviation of one, that the Gaussian approximation is not unreasonable, as is graphically shown in FIG. 30. Note that the binomial blur operation of block 442 can be repeatedly applied, in both axes of an image, to achieve an approximation to a 2D Gaussian blur.

The Laplacian of a function crosses zero wherever the gradient of the function is at a maximum with respect to changes in position parallel to the gradient. Those of ordinary skill in the art may recognize that having achieved a Gaussian-filtered image after the operation in block 442, additional steps can be executed to approximately achieve the Laplacian of a Gaussian-blurred version of the original image. Thus, the zero crossings of the Laplacian of a Gaussian-blurred version of the original image can be expected to provide an indication regarding the locations of edges in the original image.

The steps to achieve the Laplacian of a Gaussian-blurred version of the original image are described in blocks 444–446. In a block 444, the Gaussian-blurred version of the original image achieved in block 442 is shifted bitwise to the left, preferably by four bits. Note that it is important that the shift be to the left, rather than to the right. A bitwise shift to the left corresponds to a multiplication by a factor of 2 per bit, while a bitwise shift to the right corresponds to a division by a factor of 2 per bit. Thus a bitwise shift left of four bits is equivalent to multiplication by 16.

In a block 445, the image that has been shifted by four bits (the image produced in block 444) is subtracted from the Gaussian-blurred image (the image produced in block 442), thereby achieving an intermediated image. Then in block 446 a $2^{nd}$ binomial blur is applied to the intermediate image obtained in block 445 to a achieve an approximation of a Laplacian of a Gaussian-filtered image. This second binomial blur operation (applied in block 446) preferably includes more than one blurring step in each axis, and thus is referred to as a "large" binomial blur. The intent of the large binomial blurring operation is to decrease noise.

2Support for the assertion that image achieved in block 446, when well approximated by the Gaussian formula described above, is substantially equivalent to applying a Laplacian to the Gaussian-filtered image, is provided below.

If one ignores boundary effects, the Laplacian differential operator $\nabla^2 \equiv \partial_x^2 + \partial_y^2$, when applied to the 2D convolution of two continuous functions $f*g$, gives a result equal to the convolution of either function with the Laplacian of the other:

$\nabla^2(f*g) = (\nabla^2 f)*g = f*(\nabla^2 g)$.

Therefore, the Laplacian of a Gaussian-filtered image is simply the convolution of the image with the Laplacian of a Gaussian. Consider the normalized 2D Gaussian G with scale factor $\alpha$:

$G(x) = \alpha \exp[-\alpha(x^2+y^2)]$.

The Laplacian of this function is:

$\nabla^2 G = 4\alpha^2(\alpha(x^2+y^2)-1)\exp[-\alpha(x^2+y^2)]$.

But the derivative with respect to $\alpha$ is given by:

$$\partial_\alpha G = (1 - \alpha(x^2+y^2))\exp[-\alpha(x^2+y^2)] = \frac{-1}{4\alpha^2}\nabla^2 G.$$

So the Laplacian of a normalized Gaussian can be calculated by taking the derivative with respect to the scale factor. The discrete corollary of this statement for the 2D binomial blurring kernel $K_m$ is that:

$\nabla^2 K_m \propto K_{m+1} - 16 K_{m-1}$.

But if the binomial blurring step is performed once for each column, and once again for each row of the image (this step is defined as $\beta$), the result is:

$K_{m+1} = \beta K_{m-1}$, as noted above, so that:

$\nabla^2 K_m \propto (\beta - 16) K_{m-1} = K_{m-1}(\beta - 16)$.

If the binomial blur applied in block 442 is defined as $\beta$, and the bitwise shift left of step 444 is by four bits (shifting by four bits is employed, because the result is equivalent to multiplication by 16), then it will be apparent that the large binomial blur achieved by subtracting the image achieved in block 444 from the image achieved in block 442 approximates the Laplacian of a Gaussian-blurred version of the original image. Preferably, the binomial blur applied in block 442 is single blurring operation in each axis, and thus is referred to as a "small" binomial blur.

As indicated above, the zero crossings of the Laplacian of a Gaussian-blurred version of the original image can be expected to provide an indication as to the locations of edges in the original image. However, simply finding zero crossings of the image achieved in block 446 is not sufficient to guarantee that the edge found is not produced by random background noise variations. Additional steps shown in FIG. 29A and described in detail below are intended to select only those contiguous regions having edges strong enough to distinguish such regions from noise.

In order to distinguish regions that are merely part of the background from genuine objects of interest, in a block 448, four threshold operations are applied to the LOG result achieved in block 446, resulting in the generation of four binary images (one image per threshold operation). There are two threshold values T1 and T2, and they satisfy the relationship 0<T1<T2. These thresholds may be set from previously-measured characteristics of the image data, or there an adaptive computation may be employed that adjusts them in response to the image data in real time. The four binary images represent whether the LOG (i.e., the result from block 446) exceeds the positive values T2, T1, or falls below the negative values −T2, −T1. The binary images are referred to as B1+, B2+, B1−, and B2−, respectively based on T1, T2, −T1, and −T2.

The value for T2 is selected so that the LOG value is exceedingly unlikely (i.e., the probability $p \leq 10^{-6}$) to pass beyond the range (−T2, T2) by chance in a background region, but very likely to be exceeded in the neighborhood of genuine objects of interest. The signal-to-noise ratio and geometry of the imagery will determine both the degree of blurring required in the LOG process of block 446, and the appropriate value of T2 required to achieve the desired criteria noted above. The value T1 is a less stringent threshold, occasionally (probability $p \leq 0.01$) exceeded in background regions, which is optimized to give a faithful indication of the shape of visible objects.

A block 450 collectively includes steps represented by blocks 450a, 450b, 450c, 450d, and 450e; which are described below in detail in conjunction with FIG. 29B. The operations described in such blocks manipulate images B2+, B1+, and B1− to define active regions in an image mask. A block 452 similarly collectively includes steps represented by blocks 452a, 452b, 452c, 452d, and 452e, which are described below in detail, in connection with FIG. 29C. Those operations manipulate images B2−, B1−, and B1+ to define active regions in a binary image mask. In a block 454, the image mask portions generated in blocks 450 and 452 are combined and then undergo a 3×3 closing operation in a block 456.

Referring now to FIG. 29B, blocks 450a, 450b, 450c, 450d, and 450e, which collectively describe the operations performed in block 450 of FIG. 29A, will be described in detail. These operations are executed repeatedly, once for each contiguous region in which the LOG>T1 that contains at least one pixel for which the LOG>T2. At the end of each cycle of these repetitive steps, each such contiguous region has either been identified as forming a part or whole of some object of interest, or has been determined to be just outside the boundary of such an object of interest. Preferably, all the contiguous regions determined to form a part or whole of an object of interest are "turned on," by applying a logical OR operation using the binary mask image determined as explained above.

In block 450a, the contiguous region from B2+ to B1+ is filled, starting from an initial pixel located at (i, j) for which the binary image B2+ is "on." This operation may be described by the following pseudo-code:

```
Push(Stack, (i,j));
While (not_empty(Stack)) Do
    Let (i,j) = Pop(Stack);
    If B1+(i,j) Then
        Begin
            Set(B1+, (i,j), False);
            Set(Dest, (i,j), True);
            If in_column_bounds(j+1) Then
                Push(Stack, (i,j+1));
            If in_column_bounds(j−1) Then
                Push(Stack, (i,j−1));
            If in_row_bounds (i+1) Then
                Push(Stack, (i+1,j));
            If in_row_bounds (i−1) Then
                Push(Stack, (i−1,j));
        End
Done;
Let B2+ = B2+ And (Not (Dest)).
```

In the above pseudo-code, Dest is a binary image buffer that records the presence of each pixel of the contiguous region, and Stack is a last-in-first-out data structure for pixel locations, supporting the Push and Pop operations. The setting of the Dest pixel may be combined with some steps for keeping track of the first and last rows and columns set in the Dest buffer on this iteration, so that only a rectangular region immediately surrounding the contiguous ROI is used in the subsequent steps (450b–450d). Finally, any other pixels in B2+, falling within the contiguous ROI in Dest, may be cleared, since starting a new filling step (i.e., the operation executed in block 450a) at those pixels would be superfluous.

As noted in block 450 of FIG. 29A, binary images B2+, B1+, and B1− are used to activate portions of a binary mask image. Block 450a describes filling the contiguous region from binary images B2+ and B1+. In block 450b, a 3×3 dilation is performed on the binary image B1−, obtained by applying the smaller negative threshold −T1. The dilated binary image is used to determine whether the complementary objects are within objects of interest, since regions where the LOG falls outside the range of −T1 surround objects of interest. Those of ordinary skill in the art will recognize that a 3×3 dilation has the effect of producing a binary image in which pixels are turned on if corresponding pixels in the original binary image and in a 3×3 neighborhood with one or more on pixels in the original binary image are turned on.

In block 450c the outer boundary of the contiguous region filled in block 450a is determined. Preferably this step is achieved by first dilating the binary image corresponding to the region filled in block 450a with a 3×3 kernel, and then computing the logical AND of that dilated image with the inverse of the binary image corresponding to the region filled in block 450a. This step has the effect of producing a final binary image in which pixels are turned on if corresponding pixels in the original binary image and in a 3×3 neighborhood with one or more on pixels in the original binary image are turned off. This final binary image is defined as the outer boundary of the binary image corresponding to the region filled in block 450a. The number of "on" pixels in the outer boundary is determined, and stored a value "B."

In block 450d, the outer boundary of the contiguous region filled in block 450a is combined with the dilation of the complementary binary image B1– via a logical AND operation, thereby selecting some pixels of the outer boundary that represent the edges of objects. The number of "on" pixels in the binary image resulting from the logical AND operation is determined, and stored a value "A."

In block 450e, the fraction of "on pixels" (B) in the outer boundary and also in the complementary dilated binary image B1– (A) is compared to a predetermined threshold C (in one preferred embodiment, C=⅔), to determine if the edges of the contiguous region are sufficiently well-defined to allow inclusion of this contiguous region as a part or whole of an object of interest. If so, the pixels in the contiguous region are also turned on in the binary mask image being produced.

Referring now to FIG. 29C, blocks 452a, 452b, 452c, 452d, and 452e, collectively describe the operations performed in block 452 of FIG. 29A. As with the operations described above with respect to FIG. 29B, the operations of FIG. 29C are executed repeatedly, once for each contiguous region in which the LOG<–T1 and there is at least one pixel where the LOG<–T2. The steps of FIG. 29C for the negative thresholds are completely isomorphic to the steps of FIG. 29B performed for the positive thresholds, and the result is the same: each such contiguous region is determined to be a part or whole of an object of interest, or just outside such an object, and those which are parts of or whole objects may be turned on in the binary mask image being produced.

In block 452a, the contiguous region from B2– to B1– is filled, starting from an initial pixel located at (i, j) for which the binary image B2– is on. The pseudo-code described above (with the appropriate replacements of B2– for B2+) is similarly employed in block 452a.

Block 452b generally corresponds to block 450b, except that the 3×3 dilation is performed on the binary image B1+, rather than on binary image B1–. Of course, the smaller positive threshold T1 is applied. Again, the dilated binary image will be used to determine whether the complementary objects are within objects of interest, since regions where the LOG falls outside the range of T1 surround objects of interest.

The operations in blocks 452c, 452d, and 452e also correspond to the operations executed in blocks 450c, 450d, and 450e, as described above, with the appropriate inversions of the binary images being manipulated (i.e., where image B2+ is manipulated in blocks 450a–450e, image B2– is manipulated in blocks 452a–452e).

After iterating through all of the contiguous regions in the isomorphic operations described in FIGS. 29B and 29C, the active regions determined in blocks 450a–450e and block 452a–452e are combined to generate the binary mask image in block 454, which then undergoes a 3×3 closing operation in block 456. The closing operation adds pixels to the combined binary mask for which there is no 3×3 box containing the pixels, and containing only pixels which are off in the combined binary mask. A closing can be decomposed into a dilation, followed by an erosion with the same kernel.

FIG. 31 pictorially represents a leftmost image 500 producing original data delivered by the TDI camera, a middle image 502 representing transformation of the original data by the LOG operation, and a rightmost image 504 of a binary mask generated from the LOG-transformed image.

Images 500 and 502 represent grayscale values within images using the size of dark circles, one for each pixel, where the area of a circle is proportional to a constant minus the grayscale value; binary image 504 represents on pixels using dark circles, and off pixels by their absence, within a grid of squares. Image 500 produces original image data, preferably obtained with a CCD camera operated in TDI mode, imaging cells through a microscope objective. This image corresponds to the source of an example of the initial image data obtained in block 440 of FIG. 29A. After the LOG processing steps of blocks 442, 444, and 446 (FIG. 29A), the absolute value of the LOG image result is represented by image 502, where larger dark circles represent larger absolute values.

After the completion of the region-finding algorithm described above (i.e., blocks 450 and 452 in FIG. 29A, blocks 450a–450e of FIG. 29B, and blocks 452a–452e of FIG. 29C), the final object mask obtained following the closing step of block 456 in FIG. 29A is represented by image 504 of FIG. 31.

Once the steps described above have provided a final mask image, such as mask image 504, it will often be desirable to find contiguous regions from the final mask, and to create an object list, with associated masks and other data. FIG. 32 presents the data flow diagram of an algorithm for performing these tasks. It should be understood that such tasks are performed after the execution of the 3×3 closing operation in block 456 of FIG. 29A.

In FIG. 32, the final mask image produced is first eroded with a 2×2 kernel in a block 512, and then dilated with a matching 2×2 kernel in a block 514. The net effect of these two operations, referred to as "an opening," is to remove from the mask any pixels not belonging to a 2×2 contiguous block. This step is done in order to remove any single-pixel-wide extensions or connections from the mask. Note that this process is executed on a copy of the first erosion of block 512, such that the first erosion data are still available for further processing in a block 516, as described below.

In block 516, the eroded mask (i.e., the first erosion) is eroded a second time, again with a 2×2 kernel. The net effect of these two erosions (blocks 512 and 516) is to erode the mask by a 3×3 kernel, to remove any objects from the mask not containing at least one 3×3 contiguous block of pixels. The result of this operation is referred to as a "trigger mask," because it is used to trigger the finding and filling of an object in the mask.

The trigger mask is inverted in a block 518 and combined with the opened mask by a logical AND operator in a block 520. The effect of this set of operations is to create an inner boundary or border mask, since only interior pixels that are adjacent (in a 3×3 sense) to exterior pixels will remain after applying the logical AND operator.

Once the border mask has been obtained, the balance of the steps is repeated for each contiguous object containing a 3×3 block of pixels. Thus, in a block 522, a first contiguous object containing a 3×3 block of pixels is selected.

The first on pixel of the object in the trigger mask obtained in block 516 sets off a following pixel of the adjacent border, in a block 524. Basically, the border of the trigger mask is followed to connect the border. The pseudo-code for this following operation is the same as for the fill operation described in block 460 above, except for the substitution of the border mask for the binary image B1+, the substitution of the trigger mask for the binary image B2+, and in that the starting row and column for the pseudo-code are not "on" in the trigger mask, but instead, are adjacent to the first on pixel of the trigger mask. The result of this operation is a continuously connected border, along with the rectangular region containing it. The remaining operations (i.e., blocks 526–538) are preferably restricted to operate only on the rectangular region around the connected border.

Having created the connected border for the selected object, it is only necessary to fill the border to obtain an object mask. In a block 526, a 3×3 dilation is performed on the selected object to obtain an "opened object." Then, in a block 528, the object is inverted, and in a block 530, the opened object and the inversion of the object are combined to produce a halo mask, which is an outer boundary of the connected border. This raw halo mask can be subjected to an operation functionally identical to that executed in block 524, except that the starting point for the operation executed in a block 532 is found by beginning outside the object at the column of the initial trigger pixel for the object and proceeding toward the trigger pixel, until reaching the first raw halo pixel. The result of this operation is referred to as the connected halo.

Given the connected halo and connected border binary images, in a block 534, the interior of the object defined by the connected halo and connected border binary images is filled, according to the following pseudo-code:

```
For each row Do
    Let inside = False;
    For each column Do
        If inside Then
            Begin
                set(border, (row, column), True);
                let              inside           =
Not(halo(row,column+1))
            End
        Else
            let inside =
                halo(row,column)           AND
border (row, column+1):
    Done;
Done.
```

The result at the end of this operation is the filled object mask. In a block 536, the filled object mask and the corresponding image data are saved. Then, in a block 538, any pixels from the trigger mask that are contained within this filled object mask are removed, since triggering on other pixels within the same object would be a superfluous operation. In a decision block 540, it is determined if any more contiguous objects containing 3×3 blocks of pixels exist, and if so, the operations of blocks 522–538 are repeated for the next object. If in decision block 540 no other contiguous objects containing 3×3 blocks of pixels exist, the process is terminated.

Note that it is logically possible, although unlikely, for object masks obtained by the procedure described above, to be wholly contained within other object masks that are triggered on, after the object masks that are contained therein. An optional additional step would be to check for such a condition, perhaps by comparing masks before terminating the process.

FIG. 33 pictorially represents the effects of the application of the sequence of morphological operations described in conjunction with FIG. 32 to arrive at the final object filled object masks. The algorithm described in FIG. 32 is applied to object mask 504 of FIG. 31. After the initial erosion in block 512 (FIG. 32), mask 504 is transformed into image 560 of FIG. 33. The matching dilation in block 514 (FIG. 32) produces an opened mask image 562 (FIG. 33), and the second erosion operation of block 516 (FIG. 32) yields a trigger mask 564 (FIG. 33). The inversion of the trigger mask and combination with the opened mask by the logical AND operator (blocks 518 and 520 of FIG. 32) produces a border mask 566 (FIG. 33).

Starting from border pixels adjacent to the initial trigger pixels, and following the borders (i.e. blocks 522–532 of FIG. 32 performed for each of the three objects in image 566) generates connected border images 568, 572, and 576. Each connected border image is filled (i.e., blocks 534–538 of FIG. 32) to generate the filled object masks 570, 574, and 578.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for detecting an object in a pixelated image and segmenting the pixelated image to separate the object from a background, comprising the steps of:
    (a) providing pixelated image data for a plurality of pixelated images, where a pixelated image in the plurality of pixelated images may include an object;
    (b) detecting the presence of an object included within any of the pixelated images by filtering the pixelated image data, producing filtered image data in which an object is detected in a pixelated image based upon relative amplitude values of pixels corresponding to the filtered image data for said pixelated image;
    (c) segmenting the image in which the object was detected by defining a region of interest from the filtered image data for the pixelated image in which the object was detected, so that the region of interest comprises less than all of the filtered image data for said pixelated image, but includes the object that was detected in said pixelated image; and
    (d) determining object boundaries for the object using the filtered image data within the region of interest, wherein the step of determining object boundaries comprises the steps of:
        (i) applying a first binomial blur operation to the filtered image data within the regions of interest, thereby approximating convolving the filtered image data in the region of interest with a Gaussian filter, producing a Gaussian blurred image data;
        (ii) executing a bitwise shift operation on the filtered image data to produce shifted image data;
        (iii) determining a difference between the Gaussian blurred image data and the shifted image data to produce difference image data; and
        (iv) applying a second binomial blur operation to the difference image data, thereby approximating a Laplacian of the Gaussian (LOG) blurred version of the filtered image data for the region of interest and producing LOG image data.

2. The method of claim 1, wherein the step of determining object boundaries further comprises the steps of:
    (a) executing a threshold operation on the LOG image data to achieve multiple binary images; and
    (b) defining a binary mask based on the multiple binary images.

3. The method of claim 2, wherein the step of executing a threshold operation comprises the steps of:
 (a) selecting a first threshold value greater than zero and a second threshold value greater than zero, the first threshold value being larger than the second threshold value, and using the first and second threshold values to define a first pair of binary images; and
 (b) creating a negative first threshold value having an absolute value equal to that of the first threshold value and a negative second threshold value having an absolute value equal to that of the second threshold value, and using the negative first threshold value and the negative second threshold value to define a second pair of binary images.

4. The method of claim 3, wherein the first threshold value is selected to be sufficiently large so that it is statistically substantially unlikely for the LOG image data to fall outside a range defined between the first negative threshold value and the first threshold value.

5. The method of claim 3, wherein the first threshold value is selected to be sufficiently large so that there is less than one chance in a million that the LOG image data fall outside a range defined between the first negative threshold value and the first threshold value.

6. The method of claim 1, wherein the step of defining a region of interest comprises the step of defining a region of interest that encompasses only a single object.

7. The method of claim 1, wherein the step of detecting the presence of an object within the filtered image data comprises the step of normalizing grey scale values comprising the filtered image data.

8. The method of claim 1, wherein the pixelated image data represent a plurality of channels, further comprising the step of aligning the pixelated image data with a first axis that extends across the channels before detecting objects in the pixelated image data.

9. The method of claim 1, wherein the step of filtering the pixelated image data comprises the step of applying a two dimensional low pass filter to the pixelated image data to produce low pass filtered image data.

10. The method of claim 9, wherein the step of filtering the pixelated image data further comprises the step of applying a two dimensional high pass filter to the low pass filtered image data to produce the filtered image data.

11. The method of claim 10, wherein the high pass filter comprises a gradient operator.

12. The method of claim 9, wherein the step of filtering the pixelated image data further comprises the step of applying a non linear edge detection filter to the low pass filtered image data to produce the filtered image data.

13. The method of claim 1, wherein the step of filtering the pixelated image data comprises the steps of:
 (a) applying a two dimensional low pass filter to the pixelated image data to produce low pass filtered image data; and
 (b) applying a two dimensional edge enhancement filter to the low pass filtered image data to produce the filtered image data.

14. The method of claim 13, wherein the step of applying the two dimensional low pass filter to the pixelated image data comprises the step of applying a boxcar filter to the pixelated image data.

15. The method of claim 14, wherein the step of applying the boxcar filter comprises the step of applying a 3×3 boxcar filter to the pixelated image data.

16. The method of claim 13, wherein the step of applying the two dimensional edge enhancement filter to the low pass filtered image data comprises the step of increasing a magnitude of each pixel in the low pass filtered image data if the pixel is adjacent to another pixel that is disposed on an amplitude gradient.

17. The method of claim 16, further comprising the step of determining if a specific pixel is adjacent to the other pixel disposed on the amplitude gradient by calculating differences in amplitude among four adjacent pixels around the specific pixel.

18. The method of claim 17, wherein the step of calculating the differences in amplitude among four adjacent pixels comprises the steps of:
 (a) computing the differences between the four adjacent pixels along six different axes to determine an axis of least inclination;
 (b) computing an absolute difference between two of the four adjacent pixels that do not define the axis of least inclination;
 (c) computing a projection of the axis of least inclination and the absolute difference between said two of the four adjacent pixels that do not define the axis of least inclination; and
 (d) using the projection to determine a magnitude with which the specific pixel is increased.

19. The method of claim 1, wherein the step of determining a magnitude uses a quadratic summation and a lookup table.

20. The method of claim 13, wherein the step of defining a region of interest comprises the steps of:
 (a) locating a center of the object; and
 (b) generating boundaries for the region of interest.

21. The method of claim 20, wherein the step of locating the center of the object comprises the steps of:
 (a) decimating the filtered image data with the two dimensional low pass filter and the two dimensional edge enhancement filter a plurality of times, producing a succession of ordered decimated image data, based upon the number of times that the step of decimating was done;
 (b) determining if the highest order decimated image data exceeds a threshold value;
 (c) if the threshold value has been exceeded, determining a peak of the highest order decimated image data; and
 (d) extrapolating peaks for each of the other orders of decimated image data and the filtered image data, and generating boundaries for the region of interest, a peak of the filtered image data within the region of interest corresponding to a center of the object included within the region of interest.

22. The method of claim 21, wherein the filtered image data are decimated until the highest order corresponds to a single pixel.

23. The method of claim 20, wherein the step of generating the boundaries for the region of interest comprises the steps of:
 (a) applying a pattern analysis algorithm referenced to the center of the object to determine boundaries of the object; and
 (b) establishing the boundaries for the region of interest such that the region of interest encompasses the boundaries of the object.

24. The method of claim 20, wherein the step of generating the boundaries for the region of interest comprises the steps of:
 (a) applying a pattern analysis algorithm referenced to the center of the object to determine boundaries of the object;

(b) rejecting any object that is larger than a predetermined size; and (c) establishing the boundaries for the region of interest such that the region of interest encompasses the boundaries of the object.

25. The method of claim 13, wherein the step of applying the two dimensional edge enhancement filter to the low pass filtered image data comprises the step of increasing a magnitude of each pixel in the low pass image data whenever that pixel is in a region characterized as having a substantial amplitude gradient along two orthogonal axes.

26. The method of claim 25, further comprising the step of determining if a specific pixel is in a region characterized as having a substantial amplitude gradient along two orthogonal axes by implementing a gradient operator defined by the specific pixel and four adjacent pixels, the gradient operator determining a magnitude by which the specific pixel is to be increased.

27. A method for detecting an object in a pixelated image and segmenting the pixelated image to separate the object from a background, comprising the steps of:

(a) providing pixelated image data for a plurality of pixelated images, where a pixelated image in the plurality of pixelated images may include an object;

(b) detecting the presence of an object included within any of the pixelated images by filtering the pixelated image data, producing filtered image data in which an object is detected in a pixelated image based upon relative amplitude values of pixels corresponding to the filtered image data for said pixelated image, wherein the step of filtering the pixelated image data comprises the steps of:

(i) applying a two dimensional low pass filter to the pixelated image data to produce low pass filtered image data; and (ii) applying a two dimensional edge enhancement filter to the low pass filtered image data to produce the filtered image data;

(c) segmenting the image in which the object was detected by defining a region of interest from the filtered image data for the pixelated image in which the object was detected, so that the region of interest comprises less than all of the filtered image data for said pixelated image, but includes the object that was detected in said pixelated image, wherein the step of defining a region of interest comprises the steps of:

(i) using the filtered image data to generate an amplitude histogram; and (ii) comparing the mean of the amplitude histogram to a threshold value, and if the mean of the amplitude histogram exceeds the threshold value, then analyzing each pixel represented by the filtered image data to determine if the pixel is above the threshold, and if so, then including at least the pixel in the region of interest; and (d) determining object boundaries for the object using the filtered image data within the region of interest.

28. The method of claim 27, wherein if any specific pixel in at least one of a row and a column of the pixelated image exceeds the threshold value, further comprising the steps of:

(a) selecting one of said at least one of the row and the column in which the specific pixel is disposed; and (b) including the one of the row and the column that was selected within the region of interest without analyzing any more pixels in said one of the row and the column that was selected.

29. The method of claim 27, wherein if any specific pixel in a row exceeds the threshold value, further comprising the step of including the row in the region of interest without analyzing any more pixels in the row, thereby defining a region of interest that comprises fewer rows, but the same number of columns, as in the pixelated image.

30. The method of claim 29, further comprising the step of including within the region of interest a predefined number of rows that do not contain any pixels exceeding the threshold, thereby defining a region of interest that is larger than the object disposed within the region of interest.

31. The method of claim 29, further comprising the step of analyzing each pixel in the region of interest that comprises fewer rows than did the pixelated image to determine if the pixel is above the threshold, and if so, then including a column in which the pixel is disposed, in the region of interest, without analyzing any more pixels in that column, thereby defining a region of interest that comprises fewer rows and fewer columns than did the pixelated image.

32. The method of claim 27, wherein if any specific pixel in a column exceeds the threshold value, further comprising the step of including the column in the region of interest without analyzing any more pixels in the column, thereby defining a region of interest that comprises fewer columns, but the same number of rows, as in the pixelated image.

33. The method of claim 32, further comprising the step of analyzing each pixel in the region of interest that comprises fewer columns than did the pixelated image to determine if the pixel is above the threshold, and if so, then including a row in which the pixel is disposed, in the region of interest without analyzing any more pixels in the row, thereby defining a region of interest that comprises fewer rows and fewer columns than in the pixelated image.

34. The method of claim 27, wherein the threshold is determined based on a noisy image substantially free of objects.

35. The method of claim 27, further comprising the step of determining the threshold using a noise-filled image.

36. The method of claim 35, wherein the step of determining the threshold using a noise-filled image comprises the steps of:

(a) filtering pixelated image data from a noisy image with the low pass filter and the edge enhancement filter, producing filtered noisy image data;

(b) generating an amplitude histogram from the filtered noisy image data;

(c) determining a mean value of the amplitude histogram; and (e) scaling the mean value by a predetermined scale factor to determine the threshold.

37. The method of claim 36, further comprising the steps of empirically determining a value for the predetermined scale factor, where said value has been shown to remove background noise, while retaining desired image information.

38. The method of claim 36, further comprising the steps of repeating the steps of claim 36 using a plurality of different noisy images to obtain a plurality of different amplitude histograms, and using the plurality of different amplitude histograms to generate a threshold value that is robust against an object being included within the plurality of different noisy images, where inclusion of said object would undesirably increase the threshold value.

39. The method of claim 38, further comprising the step of using weighting coefficients to obtain the amplitude histograms, so that grey scale levels above the noise floor for pixels included in the filtered image data are given less weight than levels near a noise floor.

40. An image signal processing system for detecting an object in an image and segmenting the pixelated image to separate the object from a background, comprising:
 (a) a memory in which a plurality of machine instructions defining a signal processing function are stored; and
 (b) a processor that is coupled to the memory to access the machine instructions, said processor executing said machine instructions and thereby implementing a plurality of functions, including:
  (i) detecting the presence of an object included within an pixelated image corresponding to pixelated image data by filtering the pixelated image data, producing filtered image data in which an object is detected in a pixelated image based upon relative amplitude values of pixels corresponding to the filtered image data for said pixelated image;
  (ii) segmenting the pixelated image in which the object was detected by defining a region of interest from the filtered image data for the pixelated image in which the object was detected, so that the region of interest comprises less than all of the filtered image data for said pixelated image, but includes the object that was detected in said pixelated image; and
  (iii) determining object boundaries for the object using the filtered image data within the region of interest, wherein the function of determining object boundaries is implemented by:
   (A) applying a first binomial blur operation to the filtered image data within the regions of interest, thereby approximating convolving the filtered image data in the region of interest with a Gaussian filter, producing a Gaussian blurred image data;
   (B) executing a bitwise shift operation on the filtered image data to produce shifted image data;
   (C) determining a difference between the Gaussian blurred image data and the shifted image data to produce difference image data; and
   (D) applying a second binomial blur operation to the difference image data, thereby approximating a Laplacian of the Gaussian (LOG) blurred version of the filtered image data for the region of interest and producing LOG image data.

41. An image signal processing system for detecting an object in a pixelated image and segmenting the pixelated image to separate the object from a background, comprising a processor for processing pixilated image data by:
 (a) detecting an object within a pixelated image to which the pixelated image data corresponds, by filtering the pixelated image data, producing filtered image data in which an object is detected in a pixelated image based upon relative amplitude values of pixels corresponding to the filtered image data for said pixelated image, wherein filtering the pixelated image data is implemented by:
  (i) applying a two dimensional low pass filter to the pixelated image data to produce low pass filtered image data; and
  (ii) applying a two dimensional edge enhancement filter to the low pass filtered image data to produce the filtered image data;
 (b) segmenting the pixelated image in which the object was detected by defining a region of interest from the filtered image data for the pixelated image in which the object was detected, so that the region of interest comprises less than all of the filtered image data for said pixelated image, but includes the object that was detected in said pixelated image, wherein defining the region of interest is implemented by:
  (i) using the filtered image data to generate an amplitude histogram; and
  (ii) comparing the mean of the amplitude histogram to a threshold value, and if the mean of the amplitude histogram exceeds the threshold value, then analyzing each pixel represented by the filtered image data to determine if the pixel is above the threshold, and if so, then including at least the pixel in the region of interest; and
 (c) determining object boundaries for the object using the filtered image data within the region of interest.

42. The system of claim 41, wherein the processor is included in a programmed computer adapted execute the processing of the pixelated image data.

43. The system of claim 41, wherein the processor is an application specific intedrated circuit adapted, to execute the processing of the pixelated image data.

44. An article of manufacture adapted for use with a computer, comprising:
 (a) a memory medium; and
 (b) a plurality of machine instructions, which are stored on the memory medium, said plurality of machine instructions when executed by a computer, causing the computer to:
  (i) detect an object of interest within a pixelated image by filtering an image data signal;
  (ii) define a region of interest for the pixelated image, such that the region of interest comprises less than the pixelated image and encompasses the object of interest; and
  (iii) determine boundaries for objects within the region of interest, wherein the object boundaries are determined by:
   (A) applying a first binomial blur operation to the filtered image data within the region of interest, thereby approximating convolving the filtered image data in the region of interest with a Gaussian filter, producing a Gaussian blurred image data;
   (B) executing a bitwise shift operation on the filtered image data to produce shifted image data;
   (C) determining a difference between the Gaussian blurred image data and the shifted image data to produce difference image data; and
   (D) applying a second binomial blur operation to the difference image data, thereby approximating a Laplacian of the Gaussian (LOG) blurred version of the filtered image data for the region of interest and producing LOG image data.

45. An article of manufacture adapted for use with a processor, comprising:
 (a) a memory medium; and
 (b) a plurality of machine instructions, which are stored on the memory medium, said plurality of machine instructions when executed by a processor, causing the processor to:
  (i) detect the presence of an object within a pixelated image corresponding to pixelated image data by filtering the pixelated image data, producing filtered image data in which an object is detected in a pixelated image based upon relative amplitude values of pixels corresponding to the filtered image data for said pixelated image;

(ii) segment the pixelated image in which the object was detected by defining a region of interest from the filtered image data for the pixelated image in which the object was detected, so that the region of interest comprises less than all of the filtered image data for said pixelated image, but includes the object that was detected in said pixelated image; and (iii) determine object boundaries for the object using the filtered image data within the region of interest, wherein the object boundaries are determined by:

(A) approximating convolving the filtered image data in the region of interest with a Gaussian filter, by applying a binomial blur operation to the filtered image data within the region of interest, thereby producing Gaussian blurred image data;

(B) approximating a Laplacian of the Gaussian (LOG) blurred version of the filtered image data for the region of interest and producing LOG image data;

(C) using the LOG image data to generate a plurality of binary images;

(D) manipulating the plurality of binary images to define a binary mask, by dilating at least one of the plurality of binary images, such that at least one of the plurality of binary images remains undilated, and comparing the at least one binary image that was dilated to the at least one binary image that was not dilated to determine a contiguous region associated with the object; and (L) using the binary mask to determine object boundaries.

46. A method for detecting an object in a pixelated image and segmenting the pixelated image to separate the object from a background, comprising the steps of:

(a) providing pixelated image data for a plurality of pixelated images, where a pixelated image in the plurality of pixelated images may include an object;

(b) detecting the presence of an object included within any of the pixelated images by filtering the pixelated image data, producing filtered image data in which an object is detected in a pixelated image based upon relative amplitude values of pixels corresponding to the filtered image data for said pixelated image;

(c) segmenting the image in which the object was detected by defining a region of interest from the filtered image data for the pixelated image in which the object was detected, so that the region of interest comprises less than all of the filtered image data for said pixelated image, but includes the object that was detected in said pixelated image; and (d) determining object boundaries for the object using the filtered image data within the region of interest, wherein the step of determining object boundaries comprises the steps of:

(i) approximating convolving the filtered image data in the region of interest with a Gaussian filter, by applying a binomial blur operation to the filtered image data within the region of interest, thereby producing Gaussian blurred image data;

(ii) approximating a Laplacian of the Gaussian (LOG) blurred version of the filtered image data for the region of interest and producing corresponding LOG image data;

(iii) using the LOG image data to generate a plurality of binary images;

(iv) manipulating the plurality of binary images to define a binary mask, by dilating at least one of the plurality of binary images, such that at least one of the plurality of binary images remains undilated, and comparing the at least one binary image that was dilated to the at least one binary image that was not dilated to determine a contiguous region associated with the object; and (v) using the binary mask to determine object boundaries.

47. An article of manufacture adapted for use with a processor, comprising a memory medium on which are stored a plurality of machine instructions, that when executed by a processor, cause the processor to:

(a) detect the presence of an object within a pixelated image corresponding to pixelated image data by filtering the pixelated image data, producing filtered image data in which an object is detected in a pixelated image based upon relative amplitude values of pixels corresponding to the filtered image data for said pixelated image, wherein filtering the pixelated image data is implemented by:

(i) applying a two dimensional low pass filter to the pixelated image data to produce low pass filtered image data; and (ii) applying a two dimensional edge enhancement filter to the low pass filtered image data to produce the filtered image data;

(b) segment the pixelated image in which the object was detected by defining a region of interest from the filtered image data for the pixelated image in which the object was detected, so that the region of interest comprises less than all of the filtered image data for said pixelated image, but includes the object that was detected in said pixelated image, wherein defining the region of interest is implemented by:

(i) using the filtered image data to generate an amplitude histogram; and (ii) comparing the mean of the amplitude histogram to a threshold value, and if the mean of the amplitude histogram exceeds the threshold value, then analyzing each pixel represented by the filtered image data to determine if the pixel is above the threshold, and if so, then including at least the pixel in the region of interest; and (c) determine object boundaries for the object using the filtered image data within the region of interest.

48. An image signal processing system for detecting an object in an image and segmenting the pixelated image to separate the object from a background, comprising:

(a) a memory in which a plurality of machine instructions defining a signal processing function are stored; and (b) a processor that is coupled to the memory to access the machine instructions, said processor executing said machine instructions and thereby implementing a plurality of functions, including:

(i) detecting the presence of an object included within an pixelated image corresponding to pixelated image data by filtering the pixelated image data, producing filtered image data in which an object is detected in a pixelated image based upon relative amplitude values of pixels corresponding to the filtered image data for said pixelated image;

(ii) segmenting the pixelated image in which the object was detected by defining a region of interest from the filtered image data for the pixelated image in which the object was detected, so that the region of interest comprises less than all of the filtered image data for said pixelated image, but includes the object that was detected in said pixelated image; and (iii) determining object boundaries for the object using the filtered image data within the region of interest, wherein the object boundaries are determined by:
  (A) approximating convolving the filtered image data in the region of interest with a Gaussian filter, by applying a binomial blur operation to the filtered image data within the region of interest, thereby producing Gaussian blurred image data;
  (B) approximating a Laplacian of the Gaussian (LOG) blurred version of the filtered image data for the region of interest and producing LOG image data;
  (C) using the LOG image data to generate a plurality of binary images;
  (D) manipulating the plurality of binary images to define a binary mask, by dilating at least one of the plurality of binary images, such that at least one of the plurality of binary images remains undilated, and comparing the at least one binary image that was dilated to the at least one binary image that was not dilated to determine a contiguous region associated with the object; and
  (E) using the binary mask to determine object boundaries.

49. A method for detecting an object in a pixelated image and segmenting the pixelated image to separate the object from a background, comprising the steps of:
  (a) providing pixelated image data for a plurality of pixelated images, where a pixelated image in the plurality of pixelated images may include an object;
  (b) detecting the presence of an object included within any of the pixelated images by filtering the pixelated image data, producing filtered image data in which an object is detected in a pixelated image based upon relative amplitude values of pixels corresponding to the filtered image data for said pixelated image, wherein the step of filtering the pixelated image data comprises the steps of:
    (i) applying a two dimensional low pass filter to the pixelated image data to produce low pass filtered image data;
    (ii) applying a two dimensional edge enhancement filter to the low pass filtered image data to produce enhanced image data; and
    (iii) applying a grayscale manipulation to the enhanced image data, to produce the filtered image data, the filtered image data comprising at least one element selected from the group consisting essentially of a grayscale image and an amplitude histogram; and
  (c) segmenting the image in which the object was detected by defining a region of interest from the filtered image data for the pixelated image in which the object was detected, so that the region of interest comprises less than all of the filtered image data for said pixelated image, but includes the object that was detected in said pixelated image.

* * * * *

UNITED STATES PATENT AND TRADEMARK OFFICE
CERTIFICATE OF CORRECTION

PATENT NO.        : 7,190,832 B2
APPLICATION NO. : 10/200018
DATED             : March 13, 2007
INVENTOR(S)      : Keith L. Frost and James K. Riley It is certified that error appears in the above-identified patent and that said Letters Patent is hereby corrected as shown below:

| | |
|---|---|
| Column 1, line 23 | "images" should read --image-- |
| Column 1, line 50 | after "and" insert therefor --a-- |
| Column 2, line 22 | "Then" should read --The-- |
| Column 2, line 41 | after "of" insert therefor --the-- |
| Column 2, line 44 | after "of" insert therefor --the-- |
| Column 9, line 44 | "images" should read --image-- |
| Column 12, line 30 | "channel" should read --channels-- |
| Column 13, line 39 | "corners" should read --corner-- |
| Column 14, line 21 | "pixel" should read --pixels-- |
| Column 14, line 55 | " $\vec{D}_2 = |D - X| \angle -3\pi/4 = M_2 \angle 3\pi/4$ " should read -- $\vec{D}_2 = |D - X| \angle 3\pi/4 = M_2 \angle 3\pi/4$ -- |
| Column 14, line 57 | " $M_2 \angle 3\pi/4 = M_2[\cos(-3\pi/4) + j\sin(-3\pi/4)]$ " should read -- $M_2 \angle 3\pi/4 = M_2[\cos(3\pi/4) + j\sin(3\pi/4)]$ -- |
| Column 16, line 35 | after "in" delete "a" |
| Column 16, line 60 | "beings" should read --begins-- |
| Column 17, line 6 | after "to" insert therefor --a-- |
| Column 17, line 46 | after "image" (1st occurrence) insert therefor --286-- |

UNITED STATES PATENT AND TRADEMARK OFFICE
CERTIFICATE OF CORRECTION

PATENT NO. : 7,190,832 B2
APPLICATION NO. : 10/200018
DATED : March 13, 2007
INVENTOR(S) : Keith L. Frost and James K. Riley It is certified that error appears in the above-identified patent and that said Letters Patent is hereby corrected as shown below:

| | |
|---|---|
| Column 20, line 3 | after "and" insert therefor --the-- |
| Column 20, line 46 | after "in" (1st occurrence) insert therefor --a-- |
| Column 21, line 62 | "in" (1st occurrence) should read --to-- |
| Column 21, line 65 | "is" should read --in-- |
| Column 23, line 49 | after "image" insert therefor --is-- |
| Column 26, line 11 | "intermediated" should read --intermediate-- |
| Column 26, line 13 | after "to" delete "a" |
| Column 26, line 19 | before "support" delete "2" |
| Column 26, line 19 | after "that" insert therefor --the-- |
| Column 28, line 67 | "a" should read --as-- |
| Column 29, line 7 | "a" should read --as-- |
| Column 29, line 51 | "block" should read --blocks-- |
| Column 31, line 46 | "if-any" should read --if any-- |
| Column 34, line 2 (Claim 19, line 1) | "Claim 1" should read --Claim 21-- |
| Column 37, line 13 (Claim 40, line 11) | "an" should read --a-- |
| Column 38, line 17 (Claim 42, line 2) | after "adapted" insert therefor --to-- |
| Column 38, line 20 (Claim 43, line 2) | "intedrated" should read --integrated-- |
| Column 38, line 20 (Claim 43, line 2) | after "adapted" delete "," |

UNITED STATES PATENT AND TRADEMARK OFFICE
CERTIFICATE OF CORRECTION

PATENT NO. : 7,190,832 B2
APPLICATION NO. : 10/200018
DATED : March 13, 2007
INVENTOR(S) : Keith L. Frost and James K. Riley It is certified that error appears in the above-identified patent and that said Letters Patent is hereby corrected as shown below:

Column 39, line 29          "(L)" should read --(E)--
   (Claim 45, line 44)

Column 40, line 55          "an" should read --a--
   (Claim 48, line 11)

Signed and Sealed this

Fifteenth Day of May, 2007

JON W. DUDAS
*Director of the United States Patent and Trademark Office*